US007208581B1

(12) United States Patent
Zapata et al.

(10) Patent No.: US 7,208,581 B1
(45) Date of Patent: Apr. 24, 2007

(54) TRAF FAMILY PROTEINS

(75) Inventors: Juan M. Zapata, San Diego, CA (US); John C. Reed, Rancho Santa Fe, CA (US)

(73) Assignee: The Burnham Institute, La Jolla, CA (US)

( * ) Notice: Subject to any disclaimer, the term of this patent is extended or adjusted under 35 U.S.C. 154(b) by 870 days.

(21) Appl. No.: 09/706,325

(22) Filed: Nov. 3, 2000

Related U.S. Application Data

(63) Continuation of application No. 09/434,784, filed on Nov. 5, 1999, now abandoned.

(60) Provisional application No. 60/287,568, filed on Nov. 5, 1999.

(51) Int. Cl.
C07K 16/00 (2006.01)
C12P 21/08 (2006.01)
C12N 5/06 (2006.01)

(52) U.S. Cl. .............................. 530/387.1; 530/388.1; 530/389.1; 435/326; 435/346

(58) Field of Classification Search ............... 530/300, 530/350, 387.1, 387.5, 388.1, 389.1; 435/326, 435/346
See application file for complete search history.

(56) References Cited

U.S. PATENT DOCUMENTS 6,441,140 B1 * 8/2002 Comb et al. ............. 530/387.1
2002/0044941 A1 * 4/2002 Rosen et al.

FOREIGN PATENT DOCUMENTS

WO WO96/20723 7/1996

OTHER PUBLICATIONS

Abstract of Inoue, WO 97/38099, Oct. 16, 1997.*
MacLachlan et al, Journal of Cellular Biochemistry, 1998, vol. 71, pp. 467-478.*
Seaver (Genetic Engineering News 1994 vol. 14, No. 14: pp. 10 and 21).*
Everett et al (The EMBO Journal, 1997, vol. 16, pp. 1519-1530).*
Brodeur et al (Journal of Biological Chemistry, 1997, vol. 272, pp. 19777-19784).*
Campbell (Monoclonal Antibody Technology, 1985, pp. 1-32).*
Paul (Fundamental Immunology, 1993, text, pp. 460-461).*
EMBL: Accession No. AJ000644.
GenBank: Accession No. AB020705.
Arch et al., "Tumor necrosis factor receptor-associated factors (TRAFs)-a family of adapter proteins that regulates life and death" *Genes Devel*, 12: 2821-2830 (1998).
Borden K., "Ring fingers and B-boxes: zinc-binding protein-protein interaction domains," *Biochem. Cell. Biol.* 76:351-358 (1998).
Boucher et al., "Binding sites of cytoplasmic effectors TRAF1, 2, and 3 on CD30 and other members of the TNF receptor superfamily" *Biochem. Biophys. Res. Comm.*, 233: 592-600 (1997).

Crowe et al., "A metalloprotease inhibitor blocks shedding of the 80D TNF receptor and TNF processing in T lymphocytes" *J. Exp. Med.*, 181: 1205-1210 (1995).
Mosialos et al., "The Epstein-Barr Virus transforming protein LMP1 engages signaling proteins for the tumor necrosis factor receptor family" *Cell*, 80:389-399 (1995).
Nagai et al., "Identification of a novel nuclear speckle-type protein, SPOP" *FEB Lett.*, 418:23-26 (1997). (Also see GenBank Accession No. NM_003563).
Nagase et al., "Prediction of the coding sequences of unidentified human genes, XII. the complete sequences of 100 new cDNA clones from brain which code for large proteins in vitro" *DNA Res.*, 5:355-364 (1998).
Nakano et al., "TRAF5, an activator of NF-κB and putative signal transducer for the lymphotoxin-β receptor" *J. Biol. Chem.*, 271:14661-14664 (1996).
Park et al., "Structural basis for self-association and receptor recognition of human TRAF2" *Nature*, 398:533-538 (1999).
Pullen et al., "CD40-tumor necrosis factor receptor-associated factor (TRAF) interactions: regulation of CD40 signaling through multiple TRAF binding sites and TRAF hetero-oligomerization" *Biochemistry.*, 37:11836-11845 (1998).
Rabizadeh et al., "Expression of the low-affinity nerve growth factor receptor enhances β-amyloid peptide toxicity" *Proc. Natl. Acad. Sci. USA*, 91:10703-10706 (1994).
Rothe et al., "A novel family of putative signal transducers associated with the cytoplasmic domain of the 75 kDa tumor necrosis factor receptor" *Cell*, 78:681-692 (1994).
Rothe et al., "TRAF2-mediated activation of NF-κB by TNF receptor 2 and CD40" *Science*, 269:1424-1427 (1995).
Rothe et al., "I-TRAF is a novel TRAF-interacting protein that regulates TRAF-mediated signal transduction" *Proc. Natl. Acad. Sci. USA*, 93:8241-8246 (1996).
Sato et al., "FAP-1: A protein tyrosine phosphatase that associates with Fas" *Science*, 268:411-415 (1995).
Sato et al., "A novel member of the TRAF family of putative signal transducing proteins binds to the cytocolic domain of CD40" *FEBS Lett.*, 358:113-118 (1995).
Song and Donner, "Association of a RING finger protein with the cytoplasmic domain of the human type-2 tumour necrosis factor receptor" *Biochem. J.*, 309:825-829 (1995).

(Continued)

*Primary Examiner*—Karen A. Canella
(74) *Attorney, Agent, or Firm*—McDermott Will & Emery LLP

(57) ABSTRACT

In accordance with the present invention, there are provided novel TRAF-Protein-Binding-Domain polypeptides (TPBDs). The invention also provides nucleic acid molecules encoding TPBDs, vectors containing these nucleic acid molecules and host cells containing the vectors. The invention also provides antibodies that can specifically bind to invention TPBDs. Such TPBDs and/or anti-TPBD antibodies are useful for discovery of drugs that suppress autoimmunity, inflammation, allergy, allograph rejection, sepsis, and other diseases.

25 Claims, 13 Drawing Sheets

OTHER PUBLICATIONS

Takayama et al., "Cloning and functional analysis of BAG-1: A novel Bcl-2-binding protein with anti-cell death activity" *Cell*, 80:279-284 (1995).

Tatusova and madden et al., "BLAST 2 sequences, a new tool for comparing protein and nucleotide sequences" *FEMS Microbiol Lett.*, 174:247-250 (1999).

Wajant et al., "Identification of a TRAF (TNF receptor-associated factor) gene in *Caenorhabditis elegans*" *J. Mol. Evol.*, 47:656-662 (1998).

Wajant et al., "TNF receptor associated factors in cytokine signaling" *Cytokine Growth Factor Rev.*, 10:15-26 (1999).

Ye et al., "The structural basis for the recognition of diverse receptor sequences by TRAF2" *Mol. Cell.* 4:321-330 (1999).

Dadgostar and Cheng, "An intact zinc ring finger is required for tumor necrosis factor receptor-associated factor-mediated nuclear factor-κB activation but is dispensable for c-Jun N-terminal kinase signaling" *J. Biol. Chem.*, 273:24775-24780 (1998).

Darnay et al., "Activation of NF-κB by RANK requires tumor necrosis factor receptor-associated factor (TRAF) 6 and NF-κB-inducing kinase" *J. Biol. Chem.*, 274:7724-7731 (1999).

Everett et al., "A novel ubiquitin-specific protease is dynamically associated with the PML nuclear domain and binds to a herpesvirus regulatory protein" *EMBO J.*, 16:566-577 (1997). (Also see GenBank Accession No. Z72499).

Force et al., "Dominant negative mutants of TRAF3 reveal an important role for the coiled coil domains in cell death signaling by the lymphotoxin-β receptor" *J. Biol. Chem.*, 272:30835-30840 (1997).

Gedrich et al., "CD30 contains two binding sites with different specificities for members of the tumor necrosis factor receptor-associated factor family of signal transducing proteins" *J. Biol. Chem.*, 271:12852-12858 (1996).

Gene/protein characteristic table for KIAA0898, http://zearth.kazusa.or.jp/huge/gfpage/KIAA0898, as of Oct. 5, 1999 (Also see GenBank Accession No. AB020705).

Hanada et al., "Structure-function analysis of Bcl-2 protein" *J. Biol. Chem.* 270:11962-11969 (1995).

Hostager and Bishop, "Cutting Edge: Contrasting roles of TNF receptor-associated factor 2 (TRAF2) and TRAF3 in CD40-activated B lymphocyte differentiation" *J. Immunol.*, 162:6307-6311 (1999).

Ishida et al., "Identification of TRAF6, a novel tumor necrosis factor receptor-associated factor protein that mediates signaling from an amino-terminal domain of the CD40 cytoplasmic region" *J. Biol. Chem.*, 271:28745-28748 (1996).

Krajewska et al., "TRAF-4 expression in epithelial progenitor cells" *Am. J. Pathol.*, 152:1549-1561 (1998).

Krajewski et al., "Detection of multiple antigens on western blots" *Anal. Biochem.*, 236:221-228 (1996).

Kwon et al., "Identification of a novel activation-inducible protein of the tumor necrosis factor receptor superfamily and its ligand" *J. Biol. Chem.*, 274:6056-6061 (1999).

Leo et al., "Differential requirements for tumor necrosis factor receptor-associated factor family proteins in CD40-mediated induction of NF-κB and Jun N-terminal kinase activation" *J. Biol. Chem.*, 274:22414-22422 (1999).

Lin and Stavnezer, "Activation of NF-κB/Rel by CD40 engagement induces the mouse germ line immunoglobulin Cγ1 promoter" *Mol. Cell. Biol.*, 16:4591-4603 (1996).

Liu et al., "A *Drosophila* TNF-receptor-associated factor (TRAF) binds the Ste20 kinase Misshapen and activates Jun kinase" *Curr. Biol.* 9:101-104 (1999).

MacFarlane et al., "Identification and molecular cloning of two novel receptors for the cytotoxic ligand TRAIL" *J. Biol. Chem.*, 272:25417-25420 (1997).

Miyashita and Reed, "Tumor suppressor p53 is a direct transcriptional activator of the human bax gene". *Cell* 80:293-299 (1995).

* cited by examiner

FIGURE 2

```
                                    RING FINGER DOMAIN
  1  MDEQSVESIAEVFRCFICMEKLRDARLCPHCSKLCCFSCIRRWLTEQRAQCPHCRAPLQL
                                                     ZF-B BOX
 61  RELVNCRWAEEVTQQLDTLQLCSLTKHENEKDKCENHHEKLSVFCWTCKKCICHQCALW
                                        COILED COIL
121  GGMHGGHTFKFLAEIYEQHVTKVNEEVAKLRRRLMELISLVQEVERNVEAVRNAKDERVR
                                 COILED COIL
181  EIRNAVEMMIARLDQLKNKLITEMGQKTSLTQETELLESLLQEVEHQLRSCSKSELISK
                                         TRAF DOMAIN
241  SSEILMMFQQVHRKPMASFVTTPVPPDFTSELVPSYDSATFVLENFSTLRQRADPVYSPP
301  QVSGLCWRLKVYPDGNGVVRGYYLSVFLELSAGLPETSKYEYRVEMVHQSCNDPTKNII
361  REFASDFEVGECWGYNRFFRLDLLANEGYLNPQNDTVILRFQVRSPTFFQKSRDQHWYIT
                  COILED COIL
421  QLEAAQTSYIQQINNLKERLTIELSRTQKSRDLSPPDNHLSPQNDDALETRAKKSAQSDM
                                      POLY-ACIDIC REGION
481  LLEGGPTTASVREAKEDEEEKIQNEDYHHELSDGDLDLDLVYEDEVNQLDGSSSSASS
541  TATSNTEENDIDEETMSGENDVEYNMELEEGELMEDAAAAGPAGSSHGYVGSSSRISRR
601  THLCSAATSSLLDIDPLILIHLLDKRSSIENLWGLQPRPPASLLQPTASYSRKDKDQR
661  KQQAMWRVPSDLKMLKRLKTQMAEVRCMKTDVKNTLSEIKSSSAASGDMQTSLFSADQAA
721  LAACGTENSGRLQDLGMELLAKSSVANCYIRNSTNKKSNSPKPARSSVAGSLSLRRAVDP
781  GENSRSKGDCQTLSEGSPGSSQSGSRHSSPRALIHGSIGDILPKTEDRQCKALDSDAVV
                                           POLY-ACIDIC REGION
841  AVFSGLPAVEKRRKMVTLGANAKGHLEGLQMTDLENNSETGELQPVLPEGASAAPEEGM
901  SSDSDIECDTENEEQEEHTSVGGFHDSFMVMTQPPDEDTHSSFPDGEQIGPEDLSFNTDE
961  NSGF
```

FIGURE 3

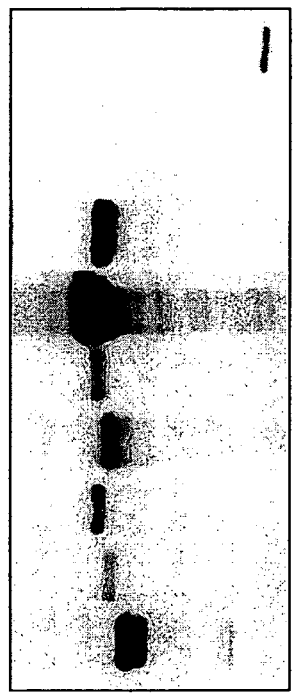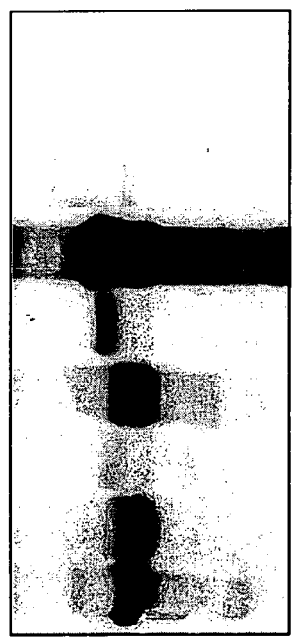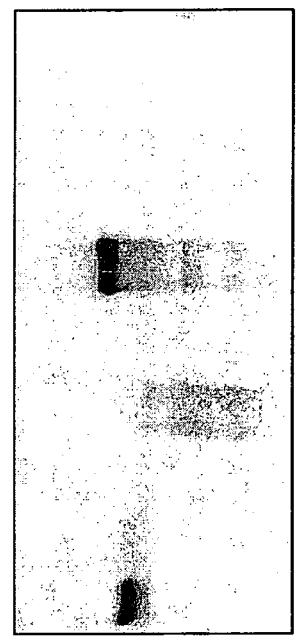
FIGURE 6

TRAF FAMILY PROTEINS

This application claims the benefit of U.S. Provisional Application No. 60/287,568, filed Nov. 5, 1999, which was converted from U.S. Ser. No. 09/434,784, filed Nov. 5, 1999, now abandoned, and is incorporated herein by reference.

This invention was made with government support under grant number CA69381 awarded by the National Institute of Health. The United States Government has certain rights in this invention.

BACKGROUND OF THE INVENTION

Field of the Invention

This invention relates generally to the fields of molecular biology and molecular medicine and more specifically to proteins involved in the regulation of immunological response and cell death.

Tumor Necrosis Factor (TNF) family cytokines play an important role in a wide variety of immunological, allergic, and inflammatory responses. Several members of the TNF family have been identified, including TNFα, Lymphotoxin-α, Lymphotoxin-β, LIGHT, CD27 Ligand (CD27L), CD30L, CD40L, Fas-L, Trail, and others. These molecules are generally produced as Type-II integral membrane proteins on the surface of cells, undergoing subsequent release into the excellular milieu as a result of proteolytic cleavage. Many of the TNF-family cytokines however remain anchored in the plasma membrane, relying on interactions with receptor-bearing cells through cell—cell contact.

The receptors for TNF-family cytokines are equally diverse. All members of the family have a conserved arrangement of cysteines in their extracellular domains, which is one of the criteria for membership in this family. The intracellular cytosolic domain of TNF-family receptors are diverse in their amino acid sequences, but can be broadly classified into two types:

(a) those that contain a protein-interaction module known as a Death-Domain (TNFR1, Fas, DR3, DR4, DR5) and those that do not (TNFR2, CD27, CD30, CD40, LTβR, 4B1 and others).

Death Domains are responsible for interactions of a subgroup of the TNF-Receptor (TNFR) family with adapter proteins which bind in turn to caspase-family intracellular proteases involved in inducing apoptosis (programmed cell death). However, the Death Domains can also mediate binding to other types of adaptor molecules which bind kinases or other types of signaling molecules rather than proteases.

Those TNFR family members that do not contain a Death Domain in their cytosolic tail rely on a family of intracellular adapter proteins for transducing signals. This family of adaptor proteins is known as the "TNF Receptor Associated Factors" (TRAFs). TRAF-family proteins contain a protein interaction domain known as the TRAF-domain that mediates their binding to the cytosolic domains of TNF-family receptors. The TRAF domain also allows for interactions among TRAF-family members, creating opportunities for homo- and hetero-oligomerization that can have important functional consequences. In humans and mice, six members of the TRAF family have been described, including TRAF1, TRAF2, TRAF3, TRAF4, TRAF5, and TRAF6. The crystal structure of the TRAF domain of TRAF2 has been solved, revealing a trimeric assembly with 3-fold symmetry and demonstrating the presence of a surface pocket on each monomer that accounts for binding to discrete peptidyl motifs found within the cytosolic domains of many members of the TNF-family receptors.

Some TRAF family proteins physically associate with protein kinases and control the activation of these kinases. TRAF2, TRAF5, and TRAF6 for example have been reported to be capable of inducing the activation of kinases involved in activation of: (a) several members of the stress-kinase family, such as the Jun N-terminal kinase (JNK), and (b) phosphorylation of IκB, an inhibitor of the transcription factor NF-κB. In contrast, TRAF1, TRAF3, and TRAF4 do not activate these kinase, and in some contexts, may interfere with kinase activation by other TRAFs. All kinase-activating members of the TRAF family contain additional protein domains (besides the TRAF-domain) which are important for their function as kinase-activators, including a RING domain and sometimes zinc-finger domains.

Gene knock-out studies in mice have demonstrated critical roles for several of the TRAF-family proteins in signal transduction pathways stimulated by TNF-family receptors. Moreover, mutational analyses of the TRAF-binding sites within the cytosolic domains of TNF-family receptors have also provided evidence that interactions of TRAFs with these receptors are critical for many of the biochemical signal-transduction and cellular biological responses induced via TNF-family receptors.

In addition to their involvement in signaling by TNF-family receptors, at least one of the known TRAFs can also participate in signaling mediated by the Interleukin-1 Receptor/Toll family of receptors. TRAF 6 interacts with a Death Domain-containing adapter protein (MyD88) and a Death Domain-containing protein kinase (IRAK) which are critical for NF-κB induction by IL-1 receptors. Thus, TRAFs may in some instances participate in signal transduction by other cytokine receptors beside those of the TNFR family. In addition, some TRAFs bind to viral proteins, suggesting that such protein interactions may play a role the mechanisms employed by viruses to either evade immune surveillance mechanisms or in virus-mediated malignant transformation.

A need exists, therefore, to identify novel TRAF family proteins or TRAF protein binding domains. The present invention satisfies this need and provides additional advantages as well.

SUMMARY OF THE INVENTION

In accordance with the present invention, there are provided novel TRAF-Protein-Binding-Domain polypeptides (TPBDs). The invention also provides nucleic acid molecules encoding TPBDs, vectors containing these nucleic acid molecules and host cells containing the vectors. The invention also provides antibodies that can specifically bind to invention TPBDs. Such TPBDs and/or anti-TPBD antibodies are useful for discovery of drugs that suppress autoimmunity, inflammation, allergy, allograph rejection, sepsis, and other diseases.

The present invention also provides a screening assay useful for identifying agents that can effectively alter the association of an invention TPBD with itself or with other proteins. By altering the self-association of TPBD or by altering their interactions with other proteins, an effective agent may increase or decrease the activation of kinases, or modulate cellular pathways that effect apoptosis, cell proliferation, cell adhesion, cell stress responses, B cell immunoglobulin class switching, and the like.

The invention also provides methods of altering the activity of TPBD in a cell, wherein such increased or decreased activity of TPBD can modulate the level of kinase activity or cellular pathways that effect apoptosis, cell proliferation, cell adhesion, cell stress responses, B cell immunoglobulin class switching, and the like. For example, the activity of TPBD in a cell can be increased by introducing into the cell and expressing a nucleic acid sequence encoding this polypeptide or proteins comprising such TPBD. In addition, the activity of TPBD or TPBD-comprising proteins in a cell can be decreased by introducing into the cell and expressing an antisense nucleotide sequence that is complementary to a portion of a nucleic acid molecule encoding the TPBD or TPBD-comprising proteins.

The invention also provides methods for using an agent that can specifically bind TPBD or a nucleotide sequence that can bind to a nucleic acid molecule encoding TPBD to diagnose a pathology that is characterized by an altered level of apoptosis, cell proliferation, cell adhesion, cell stress responses and B cell immunoglobulin class switching due to an increased or decreased level of TPBD in a cell.

BRIEF DESCRIPTION OF THE FIGURES

Figure 2:
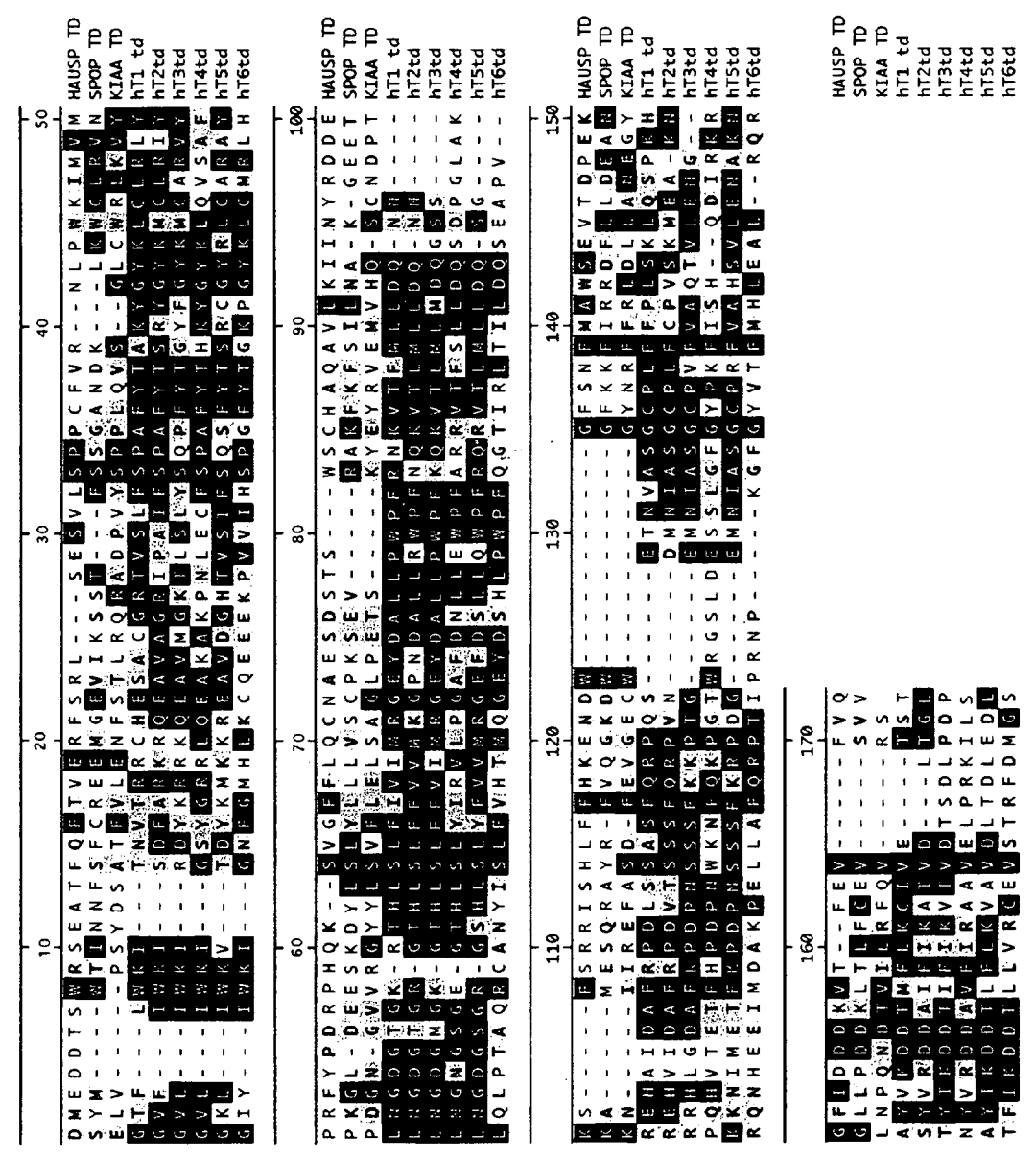

FIG. 2 shows amino acid sequences of the TRAF domains of TRAF 7 (SEQ ID NO:25)(also known as KIAA), HAUSP (SEQ ID NO:23)(also known as USP7), and SPOP (SEQ ID NO:24) in alignment with TRAF domains of six other known human TRAF proteins (hT1td through hT6td, SEQ ID NOS:26–31). Dark boxes indicate identical residues between family members. Light boxes indicate structurally related residues.

FIG. 3 shows the predicted amino acid sequence of TRAF7 (SEQ ID NO:32, corresponding to amino acids 16–979 of SEQ ID NO:6). The different protein domains and regions of the protein are indicated: ring finger domain (amino acids 15–55); ZF-B Box domain (amino acids 90–132); coiled coil (amino acids 132–177); coiled coil (amino acids 195–231); two leucine zipper domains (amino acids 197–218 and 222–245); TRAF domain (amino acids 277–403); coiled coil (amino acids 427–446); and two poly-acidic regions (amino acids)(amino acids 868–964).

FIG. 6 shows an analysis of the binding of human TRAF proteins 1–6 and I-TRAF (Rothe et al., *Proc. Natl. Acad. Sci. USA* 93:8241–8246 (1996)) to TRAF-7, HAUSP and SPOP. GST-TRAF7 (282–435), GST HAUSP (1–213) and SPOP (1–180) proteins immobilized on glutathione-Sepharose were incubated with in vitro translated $^{35}$S-TRAF proteins and I-TRAF, as indicated. Bound TRAF proteins were detected by SDS-PAGE and fluorography.

DETAILED DESCRIPTION OF THE INVENTION

Figure 1:
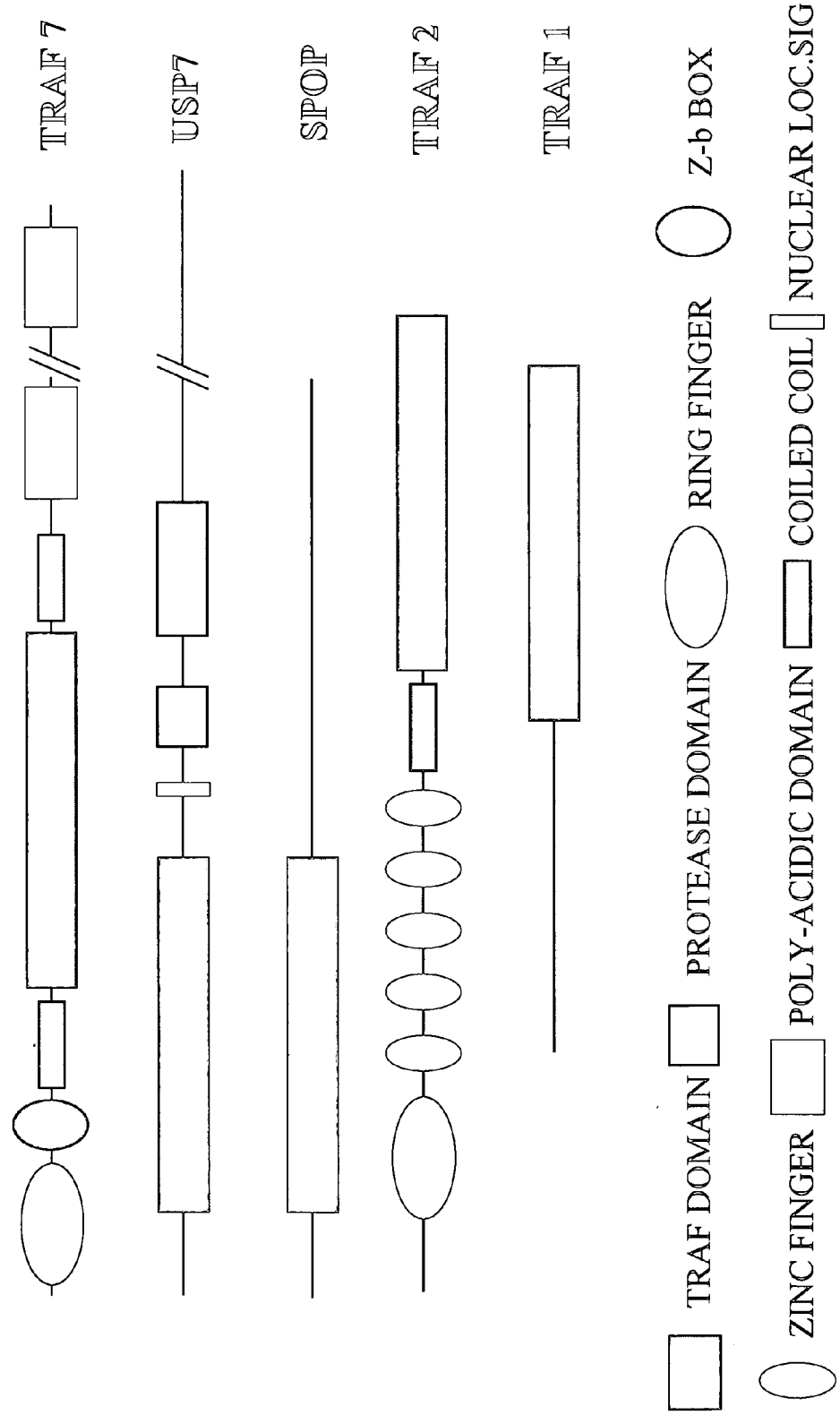
FIG. 1 shows a schematic representation of the structure of newly identified TRAF proteins referred to as HAUSP (SEQ ID NO:8) (also known as USP7), SPOP (SEQ ID NO:10) and TRAF 7 (SEQ ID NO:12); and additionally, TRAF 1 and TRAF 2, showing in shaded boxes the relative positions of the indicated protein domains: TRAF domain, protease domain, ring finger, Z-b box, zinc finger, polyacidic domain, coiled coil, and nuclear localization signal.

In accordance with the present invention, there are provided novel TRAF-protein-binding-domains (TPBDs) of newly identified TRAF proteins, and fragments thereof. As used herein, an invention TPBD refers to a peptide region that binds to one or more TRAF proteins. Invention TPBDs share sequence homology with the C-TRAF domain of TRAF proteins, and have been found herein to have binding properties similar to those of other known TRAF proteins. This domain corresponds to the portion of the TRAF domain commonly referred to as the C-TRAF or TRAF-C domain (Arch et al., supra.; and Wajant et al., *Cytokine Growth Factor Rev.* 10:15–26 (1999), each of which is incorporated herein by reference). Previously characterized human TRAF domain proteins have also been found to have N-TRAF domains immediately amino-terminal of the C-TRAF domain.

TRAF proteins were initially identified as a family of proteins that are associated with members of the TNF-receptors family. TRAF proteins are known to influence a variety of cellular processes such as class switching in B cells, apoptosis, cell proliferation, and stress response (Arch et al., *Genes Dev.* 12:2821–2830 (1998)). These effects on cellular process are thought to occur by TRAF-mediated modulation of NF-κB and/or cJun N-terminal kinase (JNK) activity. TRAF proteins thus represent an important class of intracellular proteins that mediate the signal transduction of cell surface receptors such as TNFR-family members that ultimately influence a variety of cellular processes.

In addition to binding TNF-family receptors, TRAF domain proteins also interact with other TRAF domain proteins. For example, TRAF 1, TRAF 2 and TRAF 3 all have been shown to homo-oligomerize. TRAF 2 has further been demonstrated capable of hetero-oligomerization with TRAF 1 and TRAF 5. As shown herein, TRAF domains of the present invention have all been demonstrated as capable of interacting with other TRAF-domain proteins.

The functions of the TRAF domain containing proteins, generally, supports the role of invention TPBDs and invention TRAF domain proteins in cellular pathways that effect apoptosis, cell proliferation, cell adhesion, cell stress responses and B cell immunoglobulin class switching.

For example, invention TPBDs have been found to associate with other proteins, including proteins comprising TRAF domains. Exemplary TRAF proteins to which invention TPBDs bind are human TRAF1, TRAF2, TRAF3, TRAF4, TRAF5 or TRAF6. As used herein, the term "bind" or "binding" refers to the association of an invention TPBD with another protein relatively specifically and, therefore, can form a bound complex. In particular, the binding of a TPBD to a TRAF protein is sufficiently specific such that the bound complex can form in vivo in a cell or in vitro under suitable condition.

In one embodiment, it has been found that the invention HAUSP TPBD (SEQ ID NOS:8 or 23) binds TRAF1, TRAF2, TRAF3, TRAF4, TRAF5 and TRAF6, and can inhibit the NF-κB activation activity of TRAF2, TRAF5 and TRAF6. In another embodiment, it has been found that the invention SPOP TPBD domain (SEQ ID NOS:10 or 24) binds TRAF1 and TRAF6, and can inhibit the NF-κB activation activity of TRAF6. In yet another embodiment, it has been found that the invention TRAF-7 TPBD (SEQ ID NOS:12 or 25) binds TRAF1, TRAF2, TRAF3, TRAF4, TRAF5 and TRAF6, and can inhibit the NF-κB activation activity of TRAF2 and TRAF6, and can increase the NF-κB activation activity of TRAF5. Furthermore, it has been found that the TRAF domain of TRAF7 and USP7 can inhibit the NF-κB activation induced by TNFα and CD40 overexpression, whereas the TRAF domain of SPOP showed no inhibitory activity.

In an additional embodiment, it was found that TRAF7, the TRAF domain of TRAF7, and the TRAF domain of USP7 (HAUSP) inhibited NIK-induced NFκB activation. Therefore, the invention provides TPBDs that can be used to inhibit NIK-induced NFκB activation.

In another embodiment, invention TPBDs also bind to TNF receptor family proteins. For example, the SPOP TPBD of SEQ ID NO:10 binds TNF-R2, and the TRAF-7 TPBD (SEQ ID NOS:12 or 25) binds to TNF-R2, CD40, lymphotoxin-βR, NGFRp75 and DR4, and the TRAF domain of TRAF7 also binds with itself. Further, TRAF proteins generally, are known to bind to a wide variety of cell-surface receptors, and in particular, with cytokine receptors of the TNF receptor family. Exemplary receptors to which TRAF proteins are known to bind are: TNFR1, TNFR2, CD27, CD30, CD40, 4-1BB, Ox40, LT-βR, Fas, DR3, DR4, DR5, HVEM, LMP-1 and IL-1R. In addition, TRAF proteins have been observed to bind to all members of the TNF receptor family that do not comprise a death domain. Thus, it is contemplated herein that invention TPBDs also bind one or more receptors selected from TNFR1, TNFR2, CD27, CD30, CD40, 4-1BB, Ox40, LT-βR, Fas, DR3, DR4, DR5, HVEM, LMP-1, IL-1R, and members of the TNF receptor family that do not comprise a death domain.

In another embodiment of the invention, invention TPBDs have been found to bind to TRAF-associated proteins. For example, the TRAF-7 TPBD (SEQ ID NOS:12 or 25) binds I-TRAF. Further, TRAF proteins generally are known to interact with numerous TRAF-associated proteins, such as TRADD, FADD, I-TRAF, TRIP, A20, c-IAP1, c-IAP2, Casper, RIP, RIP2, NIK, Peg3, GCK, NIK, ASK1 and IRAK. Thus, it is contemplated herein that TPBDs also bind one or more TRAF-associated proteins selected from TRADD, FADD, I-TRAF, TRIP, A20, c-IAP1, c-IAP2, Casper, RIP, RIP2, NIK, Peg3, GCK, NIK, ASK1 and IRAK.

Structurally, an invention TPBD is characterized as having the sequence: $E(X)_{17-21}LXW(X)_3VXP(X)_{15-16}L(X)_{24-28}K(X)_{15-16}W$ (SEQ ID NO:19), where X is any amino acid. Alternatively, an invention TRAF domain is characterized as having the sequence: $LXWX(X')XVXP$ (SEQ ID NO:20) where X is any amino acid and X' is selected from L and I. Preferably, an invention TRAF domain has the sequence: $E(X)_{10-13}S(X)_{6-7}LXW(X)_3VXP(x)_{10-11}S(X)_4L(X)_{24-28}K(X)_{9-10}F(X)_5WG(X)_3F(X)_{16}D(X)_{5-7}V$ (SEQ ID NO:21) where X is any amino acid. More preferably, an invention TRAF domain has the following sequence: $E(X)_4(X_A)(X)_{5-8}SX(X_B)(X)_{4-5}LXWX(X_A)XVXP(X)_{10-11}S(X_A)(X)_3L(X)_{16-18}(X_A)(X)_{4-6}(X_C)(X)_2K(X)_{9-10}F(X)_5WG(X_D)(X)_2F(X)_5(X_A)X(X_C)(X)_7(X_C) \ DX(X_A)(X)_{2-4}(X_C)V$ (SEQ ID NO:22), where X is any amino acid, $X_A$ is selected from V, L and I; $X_B$ is selected from P and G; $X_C$ is selected from D, E, N and Q; and $X_D$ is selected from Y and F. Most preferably, an invention TRAF domain comprises the sequence SEQ ID NOS:8, 10, 12, 23, 24 or 25.

TRAF domain proteins, generally, are well known in the art to modulate the activity of NF-κB and JNK. In accordance with another embodiment of the invention, invention TPBDs, HAUSP (preferably SEQ ID NOS:8 or 23), SPOP (SEQ ID NOS:10 or 24), and TRAF-7 (SEQ ID NOS:12 or 25), have been found to modulate the activity NFκB or cJun N-terminal kinase (JNK).

It has also been found that invention TPBDs modulate a variety of cellular pathways. TRAF domain proteins, generally, are well known in the art as modulating the cellular pathways that effect apoptosis, cell proliferation, cell adhesion, cell stress responses and B cell immunoglobulin class switching, and NF-kB and JNK are further known to modulate these pathways. Thus, those of skill in the art will recognize that it is within the scope of the invention that TPBDs modulate one or more cellular pathways that effect apoptosis, cell proliferation, cell adhesion, cell stress responses and B cell immunoglobulin class switching.

Presently preferred TRAF domains of the invention include amino acid sequences that comprise substantially the same protein sequence set forth in SEQ ID NOS:8, 10, 12, 23, 24 and 25, as well as biologically active, modified forms thereof.

In another embodiment, invention TPBDs include proteins comprising TPBD fragments having the sequence SEQ ID NO:19 or SEQ ID NO:20, which retain at least one native biological TPBD activity, such as immunogenicity, the ability to bind to a TNF family receptor, the ability to bind a TRAF domain protein, the ability to bind a TRAF-associated protein, the ability to modulate NF-κB activity or JNK activity, the ability to modulate apoptosis, cell proliferation, cell adhesion, cell stress responses or B cell immunoglobulin class switching, provided the TRAF protein is no longer than 213 amino acids.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

As used herein, "eukaryotic" refers to the variety of species from which an invention TPBD is derived, e.g., yeast, slime mold, plant, insect, nematode, mammal, and the like. A preferred TPBD herein, is mammalian TRAF.

As used herein, "mammalian" refers to the variety of species from which a preferred invention TPBD is derived, e.g., human, rat, mouse, rabbit, monkey, baboon, bovine, porcine, ovine, canine, feline, and the like. A more preferred TPBD herein, is human TRAF.

The term "biologically active" or "functional", when used herein as a modifier of invention TPBD(s), or polypeptide fragment thereof, refers to a polypeptide that exhibits functional characteristics similar to a TPBD. For example, one biological activity of a TPBD is the ability to bind, preferably in vivo, to a TRAF protein. Such TRAF binding activity can be assayed, for example, using the methods described in the Examples described herein.

Another biological activity of TRAF is the ability to act as an immunogen for the production of polyclonal and monoclonal antibodies that bind specifically to an invention TPBD. Thus, an invention TPBD will encode a polypeptide specifically recognized by an antibody that also specifically recognizes the TPBD having the amino acid sequence SEQ ID NO:19 or SEQ ID NO:20, preferably including an amino acid set forth in SEQ ID NOS:8, 10, 12, 23, 24 or 25. Such immunologic activity may be assayed by any method known to those of skill in the art. For example, a test-TPBD polypeptide can be used to produce antibodies, which are then assayed for their ability to bind to an invention TPBD comprising SEQ ID NO:19 or SEQ ID NO:20, preferably including a sequence set forth in SEQ ID NOs:8, 10, 12, 23, 24 or 25. If the antibody binds to the test-polypeptide and a protein including the sequence SEQ ID NO:19 or SEQ ID NO:20, and preferably also a protein including SEQ ID NOS:8, 10, 12, 23, 24 or 25 with substantially the same affinity, then the polypeptide possesses the requisite immunologic biological activity.

The TPBD containing protein set forth in SEQ ID NO:2 was initially identified as a herpes-associated ubiquitin-specific protease (HAUSP) associated with the nuclear domain of the PML protein and with Herpes simplex virus type 1 protein Vmw110 (Everett et al., *EMBO J.* 16:566–577 (1997)). The subject application represents the first identification of a portion of this protein as forming a TRAF domain.

The TPBD containing protein set forth in SEQ ID NO:4 was initially identified in serum from a scleroderma patient as having a speckled pattern in nuclei, and was termed a speckle-type POZ protein, or SPOP (Nagai et al., *FEBS Lett.* 418:23–26 (1997)). The POZ domain of SPOP has an undetermined function, but the protein was found to be widely expressed.

The TPBD containing protein set forth in SEQ ID NO:6 was identified as having a leucine-zipper region, a zinc finger region and a leucine zipper-like K-box region (Nagase et al., *DNA Res.* 5:355–364 (1998)). Initially named KIAA0898, this protein is also referred to herein as TRAF7.

In addition to the TRAF domain, TRAF7 was also found to have a number of previously unrecognized domains (see FIG. 3). The existence of a RING finger domain (amino acids 15–55) close to the N-terminus of TRAF7 was previously known. TRAF7 is KIAA0898, which was described in the database as a RING finger protein of unknown function. Besides this domain, several other new protein domains were identified in this molecule. The RING finger domain is followed by a ZF-BBox domain (amino acids 90–132) and a coiled coil (amino acids 132–177). These three protein domains form what is denominated the tripartite motif. The tripartite motif has been found in a very restricted list of proteins, including transcription factors, ribonucleoproteins, and oncoproteins and appears to be involved in protein—protein interaction (Borden, *Biochem. Cell. Biol.* 76:351–358 (1998)). After the tripartite motif, a second coiled coil (amino acids 195–231) is found. Two putative leucine zipper domains are also found in this region of the protein (amino acids 197–218 and 222–245). The TRAF domain (amino acids 277–403) is located after the leucine zippers. The TRAF domain is followed by another coiled coil (amino acids 427–446) and by two regions rich in acidic residues (amino acids 452–577 and 868–964). Therefore, in addition to TRAF domains, including the TRAF domain of TRAF7 (SEQ ID NOS:12 or 25), the invention also provides additional functional domains of TRAF7, including a ZF-BBox domain (amino acids 90–132 of SEQ ID NO:32); coiled coil domains (amino acids 132–177, 195–231 and 427–446 of SEQ ID NO:32); leucine zipper domains (amino acids 197–218 and 222–245 of SEQ ID NO:32); and poly-acidic domains (amino acids 452–577 and 868–964 of SEQ ID NO:32).

In accordance with one embodiment of the invention, it has been found that the invention TPBD (SEQ ID NOS:8 or 23) can bind all known human TRAF proteins (i.e., TRAF proteins 1 through 6), although the TRAF domain of HAUSP (SEQ ID NOS:8 or 23) binds TRAF 3 somewhat weakly, and binds TRAF 6 quite strongly. The invention TPBD of HAUSP (SEQ ID NOS:8 or 23) has also been found to inhibit NF-κB activation mediated by any of TRAF2, TRAF5 or TRAF6. The TPBD of TRAF7 (SEQ ID NOS:12 or 25) also was found to inhibit NFκB activation mediated by TRAF2 or TRAF6 (see Examples).

In another embodiment of the invention, the invention TPBD of SPOP (SEQ ID NOS:10 or 24) shows selectivity in TRAF protein interaction, binding human TRAF 1 and TRAF 6, but not human TRAF proteins 2, 3, 4 or 5. The invention TPBD of SPOP (SEQ ID NOS:10 or 24) has also been found to be specific in TNF-receptor interaction, binding TNF-receptor 2, but not FAS, CD40, lymphotoxin-β receptor, NGF receptor and DR4. The invention TPBD of SPOP (SEQ ID NOS:10 or 24) has also found to inhibit NF-κB activation mediated by TRAF6.

In a further embodiment of the invention, the invention TPBD of TRAF7 (SEQ ID NOS:12 or 25) binds all know human TRAF proteins, but binds TRAF 2 somewhat weakly, and binds TRAF 6 quite strongly. The invention TPBD of SPOP (SEQ ID NOS:10 or 24) also binds numerous members of the TNF-receptor family, including TNF-receptor 2, CD40 (albeit weakly), lymphotoxin-β receptor, NGF receptor and DR4, but not to FAS. The invention TPBD of SPOP (SEQ ID NOS:10 or 24) has also been demonstrated to inhibit NF-κB activation by either TRAF2 or TRAF6.

Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as amino acids set forth in SEQ ID NOS:8, 10, 12, 23, 24 and 25 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention. Identity of any two amino acid sequences can be determined by those skilled in the art based, for example, on a BLAST 2.0 computer alignment, using default parameters.

The invention TPBDs can be isolated by a variety of methods well-known in the art, e.g., recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra., 1989).

An example of the means for preparing the invention TPBD(s) is to express nucleic acids encoding the TPBD in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term TPBD are functional fragments or polypeptide analogs thereof. The term "functional fragment" refers to a peptide fragment that is a portion of a full length TPBD, provided that the portion has a biological activity, as defined above, that is characteristic of the corresponding full length protein. For example, a functional fragment of an invention TPBD can have an activity such as the ability, for example, to bind a TNF-family receptor, to bind another TRAF protein, to bind a TRAF-associated protein, or to modulate NF-κB activity or JNK activity, or to modulate the level of cell proliferation, apoptosis, cell adhesion, cell stress responses, class switching, and the like. In addition, the characteristic of a functional fragment of invention TPBDs to elicit an immune response is useful for obtaining an anti-TPBD antibodies. Thus, the invention also provides functional fragments of invention TPBDs, which can be identified using the binding and routine methods, such as bioassays described herein.

The term "polypeptide analog" includes any polypeptide having an amino acid residue sequence substantially the same as a sequence specifically shown herein in which one or more residues have been conservatively substituted with a functionally similar residue and which displays the ability to functionally mimic a TPBD as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of functional fragments or polypeptide analogs of the present invention can range from about 5 amino acids up to one residue less than a full-length protein sequence of an invention TPBD. In certain embodiments, the amino acid lengths include, for example, at least about 10 amino acids, at least about 20, at least about 30, at least about 40, at least about 50, at least about 75, at least about 100, at least about 150, at least about 200, at least 213, at least about 250, at least about 300, at least about 350 or more amino acids in length up to one residue less than a full-length TPBD-containing protein sequence, provided as sequence SEQ ID NO:2, 4 or 6.

Preferably, a fragment comprises a sequence selected from SEQ ID NO:19, 21 or 22. Such a fragment can also include at least about 10 residues at its amino-terminus, carboxy-terminus, or both; at least about 20 residues at its amino-terminus, carboxy-terminus, or both; at least about 30 residues at its amino-terminus, carboxy-terminus, or both; at least about 40 residues at its amino-terminus, carboxy-terminus, or both; at least about 50 residues at its amino-terminus, carboxy-terminus, or both; at least about 60 residues at its amino-terminus, carboxy-terminus, or both.

More preferably, a fragment comprises a sequence selected from SEQ ID NO:19, 21 or 22, further comprising one or more domains selected from N-TRAF, Ring Finger, Zinc finger, coiled-coil, POZ, and USP. Most preferably, a fragment has at least one fewer domains than the domains in proteins from SEQ ID NO:2, 4 or 6, wherein the domains are selected from N-TRAF, Ring Finger, Zinc finger, coiled-coil, POZ, and USP. Such domains are known in the art, as exemplified in Arch et al., supra.; and Wajant et al., supra. Identification of the domains in proteins from SEQ ID NO:2, 4 and 6 is carried out by reference to the publication reporting such proteins (i.e., Everett et al., supra., Nagai et al., supra., and Nagase et al., supra., for HAUSP (SEQ ID NO:2), SPOP (SEQ ID NO:4) and TRAF7 (SEQ ID NO:6), respectively).

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

In accordance with another embodiment, novel TPBD-containing TRAF proteins are provided. Invention TPBD-containing TRAF proteins refer to a protein comprising an invention TPBD including SEQ ID NO:19 or including SEQ ID NO:20, or a recombinantly produced invention TPBD-containing TRAF protein, including naturally occurring allelic variants thereof encoded by mRNA generated by alternative splicing of a primary transcript, provided the TPBD-containing TRAF protein are not the sequence SEQ ID NO:2, 4 or 6. Preferably, a TPBD-containing TRAF protein comprises an invention TPBD with a sequence substantially the same as SEQ ID NO:8, 10, 12, 23, 24, or 25. More preferably, a TPBD-containing TRAF protein comprises an invention TPBD with the sequence of SEQ ID NO:8, 10, 12, 23, 24, or 25.

A TPBD-containing TRAF protein comprising an invention TPBD domain is further characterized as binding one or more members of the TNF-family of receptors, or binding to one or more TRAF domain proteins, or binding to one or more TRAF associated proteins; or modulating NF-kB activity, or modulating cJun N-terminal kinase (JNK) activity; or modulating apoptosis, cell proliferation, cell adhesion, cell stress responses or B cell immunoglobulin class switching; or any combination thereof.

In another embodiment of the invention, TPBD-containing chimeric proteins are provided comprising an invention TPBD, or fragments thereof, having the sequence of SEQ ID NO:19 or SEQ ID NO:20, and further comprising one or more sequences from a heterologous protein. Invention TPBD-containing chimeric proteins include, for example, polypeptides having the sequence SEQ ID NO:8, 10, 12, 23, 24 or 25. Sequences from heterologous proteins with which the TPBD or functional fragment thereof are fused will include, for example, glutathione-S-transferase, an antibody, or other proteins or functional fragments thereof which facilitate recovery of the chimera. Further proteins with which the TPBD or functional fragment thereof are fused will include, for example, luciferase, green fluorescent protein, an antibody, or other proteins or functional fragments thereof which facilitate identification of the chimera. Still further proteins with which the TPBD or functional fragment thereof are fused will include, for example, the LexA DNA binding domain, ricin, α-sarcin, an antibody, or other proteins which have therapeutic properties or other biological activity.

As such chimeric proteins include sequences from two different proteins, the resultant amino acid sequence of the chimeric protein will typically be a non-naturally occurring sequence. Thus, in accordance with this embodiment of the invention, there are provided chimeric proteins comprising an invention TPBD, or fragments thereof, having the sequence of SEQ ID NO:19 or SEQ ID NO:20, provided the sequence of the chimeric protein is not naturally occurring.

Further invention chimeric proteins contemplated herein are chimeric proteins wherein an invention TPBD is combined with one or more domains selected from a Ring-Finger domain, a Zinc-finger domain and an N-TRAF domain from a heterologous protein. For example, the TPBD of SEQ ID NO:8, 10, 12, 23, 24, or 25 can be fused with the Ring-Finger domain of TRAF proteins such as human TRAF 2, 3, 4, 5 or 6, and the like. Another example of such a chimera is a protein wherein the TPBD of SEQ ID NO:8, 10, 12, 23, 24, or 25 is fused with the N-TRAF domain from a TRAF protein such as human TRAF 1, 2, 3, 4, 5 or 6, and the like.

Another embodiment of the invention provides TPBD, or a functional fragment thereof, fused with a moiety to form a conjugate. As used herein, a "moiety" can be a physical, chemical or biological entity which contributes functionality to TPBD or a functional fragment thereof. Functionalities contributed by a moiety include therapeutic or other biological activity, or the ability to facilitate identification or recovery of TPBD. Therefore, a moiety will include molecules known in the art to be useful for detection of the conjugate by, for example, by fluorescence, magnetic imaging, detection of radioactive emission, and the like. A moiety may also be useful for recovery of the conjugate, for example a His tag or other known tags used for protein isolation/purification, or a physical substance such as a bead. A moiety can be a therapeutic compound, for example, a cytotoxic drug which can be useful to effect a biological change in cells to which the conjugate localizes.

In accordance with another embodiment of the invention there are provided oligomers comprising invention TPBDs and fragments thereof, invention TPBD-containing proteins, TPBD-containing chimeric proteins, or combinations thereof. It has been found that a TPBD such as the TPBD of TRAF 7 (SEQ ID NOS:12 or 25) can bind at least one other, equivalent TPBD in forming a homo-oligomer. Thus in one embodiment, the invention comprises homo-oligomers of invention TPBDs and fragments thereof, invention TPBD-containing proteins, TPBD-containing chimeric proteins, or combinations thereof.

In another embodiment of the invention, there are provided hetero-oligomers comprising invention TPBDs and fragments thereof, invention TPBD-containing proteins, TPBD-containing chimeric proteins, or combinations thereof. It was found that invention HAUSP-TPBD (SEQ ID NOS:8 or 23), SPOP-TPBD (SEQ ID NOS:10 or 24) and TRAF7-TPBD (SEQ ID NOS:12 or 25) all bind, for example, multiple TRAF proteins. Thus hetero-oligomers comprising invention TPBDs and fragments thereof, invention TPBD-containing proteins, TPBD-containing chimeric proteins, or combinations thereof, and further comprising TRAF proteins such as human TRAF1, TRAF2, TRAF3, TRAF4, TRAF5, TRAF6, or combinations thereof. For example, the HAUSP-TPBD (SEQ ID NOS:8 or 23) can form a hetero-oligomer with human TRAF1, TRAF2, TRAF3, TRAF4, TRAF5, TRAF6, or combinations thereof. In another example, the SPOP-TPBD (SEQ ID NOS:10 or 24) can form a hetero-oligomer with human TRAF1, TRAF6, or combinations thereof. In a further example, the TRAF7-TPBD (SEQ ID NOS:12 or 25) can form a hetero-oligomer with human TRAF1, TRAF2, TRAF3, TRAF4, TRAF5, TRAF6, or combinations thereof.

In accordance with another embodiment of the invention, there are provided isolated nucleic acids, which encode a novel TPBD, and fragments thereof, TPBD-containing TRAF proteins and TPBD-containing chimeric proteins. Nucleic acids that encode a TPBD are those that encode a protein with the ability to bind, preferably in vivo, to one ore more members of the Tumor Necrosis Factor Receptor-family (TNFR-family), or to one or more members of the TRAF family, or to one or more TRAF-associated proteins, or any combination thereof, or have the ability to modulate NF-κB activity, JNK activity, apoptosis, cell proliferation, cell adhesion, cell stress responses or B cell immunoglobulin class switching. An invention nucleic acid encodes a TPBD having the sequence: $E(X)_{17-21}L(X)_2W(X)_3VXP(X)_{15-16}L(X)_{24-28}K(X)_{15-16}W$ (SEQ ID NO:19), where X is any amino acid. Alternatively, an invention nucleic acid encodes a TPBD having the sequence: LXWX(X')XVXP (SEQ ID NO:20) where X is any amino acid and X' is selected from L and I. Preferably, an invention nucleic acid encodes a TPBD having the sequence: $E(X)_{10-13}S(X)_{6-7}LXW(X)_3VXP(X)_{10-11}S(X)_4L(X)_{24-28}K(X)_{9-10}F(X)_5WG(X)_3F(X)_{16}D(X)_{5-7}V$ (SEQ ID NO:21), where X is any amino acid. More preferably, an invention nucleic acid encodes a TPBD having the sequence: $E(X)_4(X_A)(X)_{5-8}SX(X_B)(X)_{4-5}LXWX(X_A)XVXP(X)_{10-11}S(X_A)(X)_3L$ $(X)_{16-18}(X_A)(X)_{4-6}$ $(X_C)(X)_2K(X)_{9-10}F(X)_5WG(X_A)(X)_2F(X)_5(X_A)$ $X(X_C)(X)_7(X_C)$ $DX(X_A)(X)_{2-4}(X_C)V$ (SEQ ID NO:22), where X is any amino acid, $X_A$ is selected from V, L and I; $X_B$ is selected from P and G; $X_C$ is selected from D, E, N and Q; and $X_D$ is selected from Y and F. Most preferably, an invention nucleic acid encodes a TPBD comprising the sequence SEQ ID NO:8, 10, 12, 23, 24 or 25.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention TPBD gene or mRNA transcript in a given sample. The nucleic acid molecules described herein, and fragments thereof, are also useful as primers and/or templates in a Polymerase Chain Reacion (PCR) for amplifying genes encoding invention proteins described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a TPBD. One means of isolating a nucleic acid encoding a TPBD is to probe a mammalian genomic library with a natural or artificially designed DNA probe using methods well known in the art. DNA probes derived from the TPBD gene are particularly useful for this purpose. DNA and cDNA molecules that encode TPBDs can be used to obtain complementary genomic DNA, cDNA or RNA from eukaryotic (e.g., human, primate, mammal, plant, nematode, insect, yeast, and the like), or mammalian sources, or to isolate related cDNA or genomic clones by the screening of cDNA or genomic libraries, by methods described in more detail below. Examples of nucleic acids are RNA, cDNA, or isolated genomic DNA encoding a TPBD, provided the nucleic acids do not comprise the nucleotide sequence set forth in SEQ ID NOs:1, 3, or 5. Such nucleic acids may include, but are not limited to, nucleic acids comprising substantially the same nucleotide sequence as set forth in SEQ ID NOs:7, 9, and 11.

In one embodiment of the present invention, cDNAs encoding the invention TPBD disclosed herein comprise substantially the same nucleotide sequence as set forth in SEQ ID NOs:19 or 20, provided they do not comprise the sequence set forth in SEQ ID NO: 1, 3 or 5. Preferably, cDNAs encoding the invention TPBDs disclosed herein comprise substantially the same nucleotide sequence as set forth in any of SEQ ID NOs:7, 9, and 11, provided they do not comprise the sequence set forth in SEQ ID NO: 1, 3 or 5. Preferred cDNA molecules encoding the invention proteins comprise the same nucleotide sequence as set forth in SEQ ID No: 7, 9 and 11.

In another embodiment of the present invention, cDNAs encoding the invention TPBDs disclosed herein comprise substantially the same nucleotide sequence as set forth in SEQ ID NOs:19 or 20, provided they are no longer than 639 bases in length. Preferably, cDNAs encoding the invention TPBDs disclosed herein comprise substantially the same nucleotide sequence as set forth in any of SEQ ID NOs:7, 9, and 11, provided they are not longer than 639 bases in length. Preferred cDNA molecules encoding the invention proteins comprise the same nucleotide sequence as set forth in SEQ ID No: 7, 9 and 11.

cDNA molecules SEQ ID NOs:7, 9 and 11 encoding the invention TRAF domains respectively represent the same nucleotide sequence as nucleotides 1–639 set forth in SEQ ID No:1; nucleotides 1–540 set forth in SEQ ID NO:3; and nucleotides 847–1305 set forth in SEQ ID NO:5.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID Nos:8, 10, 12, 23, 24 and 25, provided the DNA does not encode the sequence set forth in SEQ ID NO: 2, 4 or 6. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred. Identity of any two nucleic acid sequences can be determined by those skilled in the art based, for example, on a BLAST 2.0 computer alignment, using default parameters. BLAST 2.0 searching is available at http://www.ncbi.nlm.nih.gov/gorf/b12.html., as described by Tatiana et al., *FEMS Microbiol Lett.* 174:247–250 (1999).

This invention also encompasses nucleic acids which differ from the nucleic acids shown in SEQ ID NOs:7, 9, and 11, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding TPBDs that, by virtue of the degeneracy of the genetic code, do not necessarily hybridize to the invention nucleic acids under specified hybridization conditions. Preferred nucleic acids encoding the invention TPBDs are comprised of nucleotides that encode substantially the same amino acid sequence as set forth in SEQ ID NOs:8, 10, and 12, provided they do not encode the sequence set forth in SEQ ID NO: 2, 4 or 6.

Thus, an exemplary nucleic acid encoding an invention TPBD may be selected from:
(a) DNA encoding the amino acid sequence set forth in SEQ ID NOs:19 or 20
(b) DNA that hybridizes to the DNA of (a) under moderately stringent conditions, wherein said DNA encodes biologically active TPBD, or
(c) DNA degenerate with (b), wherein said DNA encodes biologically active TPBD, wherein the nucleic acid sequence does not encode an amino acid sequence longer than 213 residues.

Another exemplary nucleic acid encoding an invention TPBD may be selected from:
(a) DNA encoding the amino acid sequence set forth in SEQ ID NOS:8, 10, 12, 23, 24 and 25,
(b) DNA that hybridizes to the DNA of (a) under moderately stringent conditions, wherein said DNA encodes biologically active TPBD, or
(c) DNA degenerate with (b), wherein said DNA encodes biologically active TPBD, wherein the nucleic acid sequence does not encode the amino acid sequence set forth in SEQ ID Nos:2, 4 or 6.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 42° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1× SSPE, and 0.1% SDS at 65° C.

The phrase "low stringency hybridization" refers to conditions equivalent to hybridization in 10% formamide, 5× Denhart's solution, 6× SSPE, 0.2% SDS at 42° C., followed by washing in 1× SSPE, 0.2% SDS, at 50° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NOs:7, 9, and 11, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NOs:7, 9, and 11, provided they do not comprise the sequence set forth in SEQ ID NO: 1, 3 or 5.

The invention nucleic acids can be produced by a variety of methods well-known in the art, e.g., the methods described herein, employing PCR amplification using oligonucleotide primers from various regions of SEQ ID NOs:7, 9, and 11, and the like.

In accordance with a further embodiment of the present invention, optionally labeled TRAF-encoding cDNAs, or fragments thereof, can be employed to probe library(ies) (e.g., cDNA, genomic, and the like) for additional nucleic acid sequences encoding novel eukaryotic TPBDs. Construction of suitable eukaryotic cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as SEQ ID NOs:1, 3, and 5, are obtained.

As used herein, a nucleic acid "probe" is single-stranded DNA or RNA, or analogs thereof, that has a sequence of nucleotides that includes at least 14, at least 20, at least 50, at least 100, at least 200, at least 300, at least 400, or at least 500 contiguous bases that are the same as (or the complement of) any contiguous bases set forth in any of SEQ ID NOs:7, 9, and 11. Preferred regions from which to construct probes include 5' and/or 3' coding regions of SEQ ID NOs:7, 9, and 11. In addition, the entire cDNA encoding region of an invention TRAF, or the entire sequence corresponding to SEQ ID NOs:7, 9, and 11, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

In another embodiment of the invention, nucleic acids are provided encoding chimeric proteins comprising an invention TPBD, or fragment thereof, having the sequence of SEQ ID NO:19 or SEQ ID NO:20, and further comprising one or more sequences from a heterologous protein. Functional fragments of TPBD include, for example, polypeptides having the sequence SEQ ID NO:8, 10, 12, 23, 24 or 25. Nucleic acids encoding proteins with which the TPBD or functional fragment thereof are fused will also encode, for example, glutathione-S-transferase, an antibody, or other proteins or functional fragments thereof which facilitate recovery of the chimera. Nucleic acids of the invention can also encode proteins with which the TPBD or functional fragment thereof are fused, for example, luciferase, green fluorescent protein, an antibody, or other proteins or functional fragments thereof which facilitate identification of the chimera. Still further nucleic acids of the invention encode proteins with which the TPBD or functional fragment thereof are fused including, for example, the LexA DNA binding domain, ricin, α-sarcin, an antibody, or other proteins which have therapeutic properties or other biological activity.

The present invention also provides compositions containing an acceptable carrier and any of an isolated, purified TPBD-containing protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

The TPBD compositions described herein can be used, for example, in methods for modulating the activity of members of the TNFR family. TNF family receptor binding is well known in the art as mediating the signal transduction activity of the receptor, and it is demonstrated herein that invention TPBDs can bind TNF receptors. Thus it is within the scope of the present invention that a protein comprising the sequence SEQ ID NO:19 or 20, or a nucleic acid encoding a protein comprising the sequence SEQ ID NO:19 or 20, modulates the activity of one or more TNF family receptors.

In one embodiment, modulation of a member of the TNFR family will comprise the step of contacting a member of the TNFR family with a protein comprising the sequence SEQ ID NO:19 or 20. Preferably, the method comprises contacting a cell with a protein comprising the sequence of SEQ ID NO:8, 10, 12, 23, 24 or 25.

In another embodiment, modulation of a member of the TNFR family will comprise the step of contacting a member of the TNFR family with a nucleic acid encoding a protein comprising the sequence SEQ ID NO:19 or 20. Preferably, the method comprises contacting a cell with a nucleic acid encoding a protein comprising the sequence of SEQ ID NO:8, 10, 12, 23, 24 or 25.

In another embodiment, the TPBD compositions described herein can be used, for example, in methods for modulating the activity of TRAF domain containing proteins. Thus it is within the scope of the present invention that a protein comprising the sequence SEQ ID NO:19 or 20, or a nucleic acid encoding a protein comprising the sequence SEQ ID NO:19 or 20, modulates the activity of one or more TRAF domain containing proteins.

In one embodiment, modulation of a TRAF domain containing protein will comprise the step of contacting a TRAF domain containing protein with a protein comprising the sequence SEQ ID NO:19 or 20. Preferably, the method comprises contacting a cell with a protein comprising the sequence of SEQ ID NO:8, 10, 12, 23, 24 or 25.

In another embodiment, modulation of a TRAF domain containing protein will comprise the step of contacting a TRAF domain containing protein with a nucleic acid encoding a protein comprising the sequence SEQ ID NO:19 or 20. Preferably, the method comprises contacting a cell with a nucleic acid encoding a protein comprising the sequence of SEQ ID NO:8, 10, 12, 23, 24 or 25.

In another embodiment, a TPBD comprising the sequence SEQ ID NO:19 or 20, or a nucleic acid encoding a protein comprising the sequence SEQ ID NO:19 or 20, modulates the activity of one or more TRAF-associated proteins. While some TRAF-associated proteins are known to modulate NF-κB activity, others are known to modulate cJun N-terminal kinase (JNK) activity, and still others are known to modulate the activity of other proteins. For example, c-IAP1 and c-IAP2 modulate caspase activity and thus influence apoptosis. Thus it is within the scope of the invention that an invention TRAF domain protein can modulate the activity of TRAF-associated proteins any protein with which TRAF-associated proteins are known to interact.

In one embodiment, modulation of a TRAF-associated protein will comprise the step of contacting a TRAF-associated protein with a protein comprising the sequence SEQ ID NO:19 or 20. Preferably, the method comprises contacting a cell with a protein comprising the sequence of SEQ ID NO:8, 10, 12, 23, 24 or 25.

In another embodiment, modulation of a TRAF-associated protein will comprise the step of contacting a TRAF-associated protein with a nucleic acid encoding a protein comprising the sequence SEQ ID NO:19 or 20. Preferably, the method comprises contacting a cell with a nucleic acid encoding a protein comprising the sequence of SEQ ID NO:8, 10, 12, 23, 24 or 25.

TPBD compositions can also be used, for example, in methods for modulating the activity of NF-κB and cJun N-terminal kinase (JNK). Proteins homologous to invention TPBDs, for example, human TRAF domain proteins, are well known in the art as modulating the activity of NF-κB and JNK, and it is further shown herein that SEQ ID NOS:8, 10, 12, 23, 24 and 25 can modulate NF-κB activity. Thus, in accordance with another embodiment of the invention, a protein comprising the sequence SEQ ID NO:19 or 20, or a nucleic acid encoding a protein comprising the sequence SEQ ID NO:19 or 20, modulates the activity of NF-κB or JNK.

In one embodiment, modulation of NF-κB or JNK activity will comprise the step of contacting a cell containing NF-κB or JNK activity with a protein comprising the sequence SEQ ID NO:19 or 20. Preferably, the method comprises contacting a cell with a protein comprising the sequence of SEQ ID NO:8, 10, 12, 23, 24 or 25.

In another embodiment, modulation of NF-κB or JNK activity will comprise the step of contacting a cell containing NF-κB or JNK activity with a nucleic acid encoding a protein comprising the sequence SEQ ID NO:19 or 20. Preferably, the method comprises contacting a cell with a nucleic acid encoding a protein comprising the sequence of SEQ ID NO:8, 10, 12, 23, 24 or 25.

The functions of the invention TPBDs support the role of TRAFs in modulating cellular pathways that effect apoptosis, cell proliferation, cell adhesion, cell stress responses and B cell immunoglobulin class switching. Thus, in accordance with another embodiment of the invention, a protein comprising the sequence SEQ ID NO:19 or 20, or a nucleic acid encoding a protein comprising the sequence SEQ ID NO:19 or 20, modulates apoptosis, cell proliferation, cell adhesion, cell stress responses or B cell immunoglobulin class switching.

In one embodiment, modulation of apoptosis, cell proliferation, cell adhesion, cell stress responses or B cell immunoglobulin class switching will comprise the step of contacting a cell with a protein comprising the sequence SEQ ID NO:19 or 20, whereby apoptosis, cell proliferation, cell adhesion, cell stress responses or B cell immunoglobulin class switching is modulated. Preferably, the method comprises contacting a cell with a protein comprising the sequence of SEQ ID NO:8, 10, 12, 23, 24 or 25.

In another embodiment, modulation of apoptosis, cell proliferation, cell adhesion, cell stress responses or B cell immunoglobulin class switching will comprise the step of contacting a cell with a nucleic acid encoding a protein comprising the sequence SEQ ID NO:19 or 20, whereby apoptosis, cell proliferation, cell adhesion, cell stress responses or B cell immunoglobulin class switching is modulated. Preferably, the method comprises contacting a cell with a nucleic acid encoding a protein comprising the sequence of SEQ ID NO:8, 10, 12, 23, 24 or 25.

Also provided are antisense-nucleic acids having a sequence capable of binding specifically with full-length or any portion of an mRNA that encodes TPBD polypeptides so as to prevent translation of the mRNA. The antisense-nucleic acid may have a sequence capable of binding specifically with any portion of the sequence of the cDNA encoding TPBD polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Compositions comprising an amount of the antisense-nucleic acid, described above, effective to reduce expression of TPBD polypeptides by passing through a cell membrane and binding specifically with mRNA encoding TPBD polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense-nucleic acid compositions are useful to inhibit translation of mRNA encoding invention polypeptides. Synthetic oligonucleotides, or other antisense chemical structures are designed to bind to mRNA encoding TPBD polypeptides and inhibit translation of mRNA and are useful as compositions to inhibit expression of TPBD associated genes in a tissue sample or in a subject.

In accordance with another embodiment of the invention, kits for detecting mutations, duplications, deletions, rearrangements and aneuploidies in TPBD genes comprising at least one invention probe or antisense nucleotide.

The present invention provides means to modulate levels of expression of TPBD polypeptides by employing synthetic antisense-nucleic acid compositions (hereinafter SANC) which inhibit translation of mRNA encoding these polypeptides. Synthetic oligonucleotides, or other antisense-nucleic acid chemical structures designed to recognize and selectively bind to mRNA, are constructed to be complementary to full-length or portions of a TPBD coding strand, including nucleotide sequences set forth in SEQ ID NOs:7, 9, and 11. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed supra. The SANC is also designed to recognize and selectively bind to target mRNA sequence, which may correspond to a sequence contained within the sequences shown in SEQ ID NOs:7, 9, and 11. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp. 40; both incorporated herein by reference).

In accordance with yet another embodiment of the present invention, there is provided a method for the recombinant production of invention TPBDs by expressing the above-described nucleic acid sequences in suitable host cells. Recombinant DNA expression systems that are suitable to produce TPBDs described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, *Nature Vol.* 277:108–114 (1979)) the Okayama-Berg cloning system (*Mol. Cell. Biol.* 2:161–170 (1982)), and the expression cloning vector described by Genetics Institute (Wong et al., *Science* 228:810–815 (1985)), are available which provide substantial assurance of at least some expression of the protein of interest in the transformed eukaryotic cell line.

Particularly preferred base vectors which contain regulatory elements that can be linked to the invention TPBD-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning*: A Laboratory Manual (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is *E. coli*.

In one embodiment, nucleic acids encoding the invention TPBDs can be delivered into mammalian cells, either in vivo or in vitro using suitable viral vectors well-known in the art. Suitable retroviral vectors, designed specifically for "gene therapy" methods, are described, for example, in WIPO publications WO 9205266 and WO 9214829, which provide a description of methods for efficiently introducing nucleic acids into human cells. In addition, where it is desirable to limit or reduce the in vivo expression of the invention TRAF, the introduction of the antisense strand of the invention nucleic acid is contemplated.

Viral based systems provide the advantage of being able to introduce relatively high levels of the heterologous nucleic acid into a variety of cells. Suitable viral vectors for introducing invention nucleic acid encoding an TPBD into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology,* 153:545–563 (1987); Cytomegalovirus vectors (Mocarski et al., in *Viral Vectors,* Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS, USA,* 85:6469 (1980)), adenovirus vectors (e.g., Logan et al., *PNAS, USA,* 81:3655–3659 (1984); Jones et al., *Cell,* 17:683–689 (1979); Berkner, *Biotechniques,* 6:616–626 (1988); Cotten et al., *PNAS, USA,* 89:6094–6098 (1992); Graham et al., *Meth. Mol. Biol.,* 7:109–127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS, USA,* 89:6099–6103 (1992); Curiel et al., *Hum. Gene Ther.,* 3:147–154 (1992); Gao et al., *Hum. Gene Ther.,* 4:14–24 (1993)) are employed to transduce mammalian cells with heterologous TPBD nucleic acid. Any of the plasmid expression vectors described herein may be employed in a TfAdpl-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *PNAS, USA,* 85:9655–9659 (1988)), and the like.

In accordance with yet another embodiment of the present invention, there are provided anti-TPBD antibodies having specific reactivity with one or more TPBD polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY (1989) which are incorporated herein by reference).

Antibody so produced can be used, inter alia, in diagnostic methods and systems to detect the level of TPBD present in a mammalian, preferably human, body sample, such as tissue or vascular fluid. Such antibodies can also be used for the immunoaffinity or affinity chromatography purification of the invention TRAF. In addition, methods are contemplated herein for detecting the presence of an invention TPBD either within a cell, or on the surface of a cell, comprising contacting the cell with an antibody that specifically binds to TPBD polypeptides, under conditions permitting binding of the antibody to the TPBD polypeptides, detecting the presence of the antibody bound to the TPBD polypeptide, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target TPBD polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-TPBD antibodies are contemplated for use herein to modulate the activity of the TPBD polypeptide in living animals, in humans, or in biological tissues or fluids isolated therefrom. The term "modulate" refers to a compound's ability to increase (e.g., via an agonist), decrease (e.g., via an antagonist), or otherwise modify (e.g., increasing a first TPBD activity while decreasing a second TPBD activity) the biological activity of an invention TPBD protein, such as TNFR family-binding, TRAF protein binding activity, TRAF-associated protein binding activity, NF-κB modulating activity, JNK modulating activity, apoptosis modulating activity, cell proliferation modulating activity, cell adhesion, cell stress responses modulating activity, or B cell immunoglobulin class switching modulating activity, and the like. Accordingly, compositions comprising a carrier and an amount of an antibody having specificity for TPBD polypeptides effective to block naturally occurring ligands or other TPBD-associated proteins, and the like, from binding to invention TPBD polypeptides are contemplated herein. For example, a monoclonal antibody directed to an epitope of an invention TPBD polypeptide including an amino acid sequence set forth in SEQ ID NOs:8, 10, 12, 23, 24 and 25 can be useful for this purpose.

The present invention further provides transgenic non-human mammals that are capable of expressing exogenous nucleic acids encoding TPBDs. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of TPBD-containing proteins, invention TPBDs can either be overexpressed or underexpressed (such as in the well-known knock-out transgenics) in transgenic mammals.

Also provided are transgenic non-human mammals capable of expressing nucleic acids encoding TPBD polypeptides so mutated as to be incapable of normal activity, i.e., do not express native TPBD. The present invention also provides transgenic non-human mammals having a genome comprising antisense nucleic acids complementary to nucleic acids encoding TPBD polypeptides, placed so as to be transcribed into antisense mRNA complementary to mRNA encoding TPBD polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NOs:1, 3, and 5. An example of a non-human transgenic mammal is a transgenic mouse. Examples of tissue specificity-determining elements are the metallothionein promoter and the L7 promoter.

Animal model systems which elucidate the physiological and behavioral roles of TPBD polypeptides are also provided, and are produced by creating transgenic animals in which the expression of the TPBD polypeptide is altered using a variety of techniques. Examples of such techniques include the insertion of normal or mutant versions of nucleic acids encoding an TRAF polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of TPBD genes with the native gene locus in transgenic animals, to alter the regulation of expression or the structure of TPBD polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of TPBD polypeptides.

In contrast to homologous recombination, microinjection adds genes to the host genome, without removing host genes. Microinjection can produce a transgenic animal that is capable of expressing both endogenous and exogenous TPBDs. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention TPBDs. These in vitro screening assays provide information regarding the function and activity of invention TPBDs, which can lead to the identification and design of compounds that are capable of specific interaction with one or more types of polypeptides, peptides or proteins.

An invention TPBD, as used herein, contains the sequence $E(X)_{17-21}L(X)_2W(X)_3VXP(X)_{15-16}L(X)_{24-28}K(X)_{15-16}W$ (SEQ ID NO:19), where X is any amino acid. Alternatively, an invention TPBD is characterized as having the sequence: LXWX(X')XVXP (SEQ ID NO:20) where X is any amino acid and X' is selected from L and I. Preferably, an invention TPBD has the sequence: $E(X)_{10-13}S(X)_{6-7}LXW(X)_3VXP(X)_{10-11}S(X)_4L(X)_{24-28}K(X)_{9-10}F(X)_5WG(X)_3F(X)_{16}D(X)_{5-7}V$ (SEQ ID NO:21), where X is any amino acid. More preferably, an invention TPBD has the following sequence: $E(X)_4(X_A)(X)_{5-8}SX(X_B)(X)_{4-5}LXWX(X_A)XVXP(X)_{10-11}S(X_A)(X)_3L(X)_{16-18}(X_A)(X)_{4-6}(X_C)(X)_2K(X)_{9-10}F(X)_5WG(X_A)(X)_2F(X)_5(X_A)X(X_C)(X)_7(X_C)DX(X_A)(X)_{2-4}(X_C)V$ (SEQ ID NO:22), where X is any amino acid, $X_A$ is selected from V, L and I; $X_B$ is selected from P and G; $X_C$ is selected from D, E, N and Q; and $X_D$ is selected from Y and F. Most preferably, an invention TPBD comprises the sequence SEQ ID NO:8, 10, 12, 23, 24 or 25.

By the known homology of invention TPBDs to known TRAF domains, it is within the scope of the invention that invention TPBD also have a role in cellular pathways that effect apoptosis, cell proliferation, cell adhesion, cell stress responses and B cell immunoglobulin class switching. Thus, invention TPBDs also provide drug discovery targets for a broad variety of pathologies including autoimmunity, inflammation, allergy, allograph-rejection and sepsis, and for a broad variety of cancer pathologies, such as, gliomas, carcinomas, sarcomas, melanomas, hamartomas and the like. In certain aspects of the invention, invention TRAF proteins, agonist or antagonists thereto, are used to treat autoimmunity, inflammation, allergy, allograph-rejection, sepsis, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like.

Also provided herein are methods of treating pathologies, said method comprising administering an effective amount of an invention therapeutic composition. Such compositions are typically administered in a physiologically compatible composition.

Methods of treating pathologies of abnormal cell proliferation will include methods of modulating the activity of one or more oncogenic proteins, wherein the oncogenic proteins specifically interact with a TPBD. Methods of modulating the activity of such oncogenic proteins will include contacting the oncogenic protein with a substantially pure TPBD or an active fragment (i.e., oncogenic protein-binding fragment) thereof. This contacting will modulate the activity of the oncogenic protein, thereby providing a method of treating a pathology caused by the oncogenic protein. Further methods of modulating the activity of oncogenic proteins will include contacting the oncogenic protein with an agent, wherein the agent modulates the interactions between the TPBD and the oncogenic protein.

Methods of treating immune-based pathologies such as autoimmunity, inflammation, allergy, allograph-rejection, and sepsis will include modulating the activity of one or more proteins that modulate immune response, wherein the protein that modulates immune response specifically interact with a TPBD. Methods of modulating the activity of such protein that modulates immune response will include contacting the protein that modulates immune response with a substantially pure TPBD or an active fragment (i.e., protein-binding fragment) thereof. This contacting will modulate the activity of the protein that modulates immune response, thereby providing a method of treating a pathology caused by the protein that modulates immune response. Further methods of modulating the activity of a protein that modulates immune response will include contacting the protein that modulates immune response with an agent, wherein the agent modulates the interactions between the TPBD and the protein that modulates immune response.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides therapeutic compositions useful for practicing the therapeutic methods described herein. Therapeutic compositions of the present invention, such as pharmaceutical compositions, contain a physiologically compatible carrier together with an invention TPBD (or functional fragment thereof), a TPBD modulating agent, such as a compound (agonist or antagonist) identified by the methods described herein, or an anti-TPBD antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate activity of an invention TPBD. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of an TPBD-modulating agent or compound identified herein that, when administered in a physiologically acceptable composition, is sufficient to achieve a plasma concentration of from about 0.1 μg/ml to about 100 μg/ml, preferably from about 1.0 μg/ml to about 50 μg/ml, more preferably at least about 2 μg/ml and usually 5 to 10 μg/ml. Therapeutic invention anti-TPBD antibodies can be administered in proportionately appropriate amounts in accordance with known practices in this art.

In accordance with still another embodiment of the present invention, there are provided methods for identifying compounds which bind to TPBD polypeptides. The invention proteins may be employed in a competitive binding assay. Such an assay can accommodate the rapid screening of a large number of compounds to determine which compounds, if any, are capable of binding to TPBDs. Subsequently, more detailed assays can be carried out with those compounds found to bind, to further determine whether such compounds act as modulators, agonists or antagonists of invention TPBDs. Compounds that bind to and/or modulate invention TPBDs can be used to treat a variety of pathologies mediated by invention TPBDs.

In another embodiment of the invention, there is provided a bioassay for identifying compounds which modulate the activity of invention TPBD polypeptides. Invention TPBD polypeptides are known to influence the activities of, for example, NF-κB. Further, homologous TRAF polypeptides are known to influence the activities of, for example, NF-κB and cJun N-terminal kinase (JNK). Thus a reporter gene construct to assay for NF-κB or JNK activity can be used to test invention TPBD activity (see Examples). According to this method, invention TPBD polypeptides are contacted with an "unknown" or test substance, the activity of the invention TPBD polypeptide is monitored subsequent to the contact with the "unknown" or test substance, and those substances which effect a resultant modulation of, for example, NF-κB activity or JNK activity are identified as functional ligands for TPBD polypeptides.

Alternative bioassays for identifying compounds which modulate the activity of invention TPBD polypeptides can be used which routinely are used to test for protein:protein interactions. Such bioassays include yeast two-hybrid assays, glutathione-S-transferase fusion protein binding assays, co-immunoprecipitation assays, and the like. Such assays are well known in the art and can be found in standard reference texts such as Sambrook et al., supra., and Current Protocols in Molecular Biology, supra.

In accordance with another embodiment of the present invention, transformed host cells that recombinantly express invention polypeptides can be contacted with a test compound, and the modulating effect(s) thereof can then be evaluated by comparing the TPBD-mediated response (e.g., via reporter gene expression) in the presence and absence of test compound, or by comparing the response of test cells or control cells (i.e., cells that do not express TPBD polypeptides), to the presence of the compound.

As used herein, a compound or a signal that "modulates the activity" of invention TPBD polypeptides refers to a compound or a signal that alters the activity of TRAF polypeptides so that the activity of the invention polypeptide is different in the presence of the compound or signal than in the absence of the compound or signal. In particular, such compounds or signals include agonists and antagonists. An agonist encompasses a compound or a signal that activates TPBD protein expression. Alternatively, an antagonist includes a compound or signal that interferes with TPBD expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate TPBD activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of TPBD polypeptides can be modulated by contacting the polypeptides with an effective amount of at least one compound identified by the above-described bioassays.

In accordance with another embodiment of the present invention, there are provided methods for diagnosing cancer, said method comprising:

detecting, in said subject, a defective sequence or mutant of SEQ ID NOs:7, 9, and 11.

In accordance with another embodiment of the present invention, there are provided diagnostic systems, preferably in kit form, comprising at least one invention nucleic acid in a suitable packaging material. The diagnostic nucleic acids are derived from the TPBD-encoding nucleic acids described herein. In one embodiment, for example, the diagnostic nucleic acids are derived from any of SEQ ID NOs:7, 9, and 11. Invention diagnostic systems are useful for assaying for the presence or absence of nucleic acid encoding TPBD in either genomic DNA or in transcribed nucleic acid (such as mRNA or cDNA) encoding TRAF.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding TPBD including the nucleotide sequences set forth in SEQ ID NOs:7, 9, and 11 or mutations or deletions therein, thereby diagnosing the presence of, or a predisposition for, cancer. In addition, the packaging material contains instructions indicating how the materials within the kit are employed both to detect a particular sequence and diagnose the presence of, or a predisposition for, cancer.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

EXAMPLES

I. Isolation of the TPBDs of TRAF7, HAUSP and SPOP

Nucleic acids encoding the TRAF protein binding domain fragments (TPBDs) of TRAF7 (residues 282–435 of SEQ ID NO:6), HAUSP (residues 1–213 of SEQ ID NO:2) and SPOP (residues 1–180 of SEQ ID NO:4) were isolated by polymerase chain reaction (PCR) using 2 µg of cDNA from Jurkat cells (The method for RNA extraction and cDNA synthesis was provided by the manufacturer (Pharmingen). The PCR was performed for 1 cycle of 94° C. for 2 min followed by 35 cycles of 94° C. for 15 s, 60° C. for 20 s and 72° C. for 100 s, followed by a final cycle of 72° C. for 5 min, using the following primers HAUSP: 5' GCGAATTC-CAGGCCGCG 3' (SEQ ID NO:13) and 5' TTCCTCGAGC-CGACTTAGCCTGTGTGC 3' (SEQ ID NO:14); SPOP: 5' CTTCGAATTCGCGATGTCAAGGGTTCC 3' (SEQ ID NO:15) and 5' CCATGCTCGAGGTATTCTAGCCA-GAAATG 3' (SEQ ID NO:16); TRAF 7: 5' CCAGAAT-TCACCAGTGAATTAGTGCC 3' (SEQ ID NO:17) and 5' CCACTCGAGTAATGTACCAATGCTAGTCC 3' (SEQ ID NO:18). The amplified fragments were purified, digested with EcoR1 and Xho 1 restriction enzymes and subcloned into pcDNA-3-myc tag and into pGEX4T (Pharmacia).

II. Expression of TPBCs TRAF7, USP7 and SPOP

To determine mRNA expression of genes encoding various TRAF domain proteins, Northern blot analysis of the mRNA levels of TRAF7, USP7 and SPOP was performed in human tissues. $^{32}$P-labeled cDNA fragments of TRAF7, USP7 or SPOP corresponding to the TRAF domains were sequentially hybridized, in the order of TRAF7, USP7 and SPOP, to filter-immobilized poly-A$^+$ RNA from various tissues (1 μg/lane) (Clontech; Palo Alto Calif.). The tissues tested were brain, heart, skeletal muscle, colon, thymus, spleen, kidney, liver, small intestine, placenta, lung and peripheral blood leukocytes (PBL). Hybridized fragments were visualized by autoradiography. The same RNA blot was finally hybridized with a human β-actin cDNA probe to control for RNA loading (bottom panel).

Figure 4:
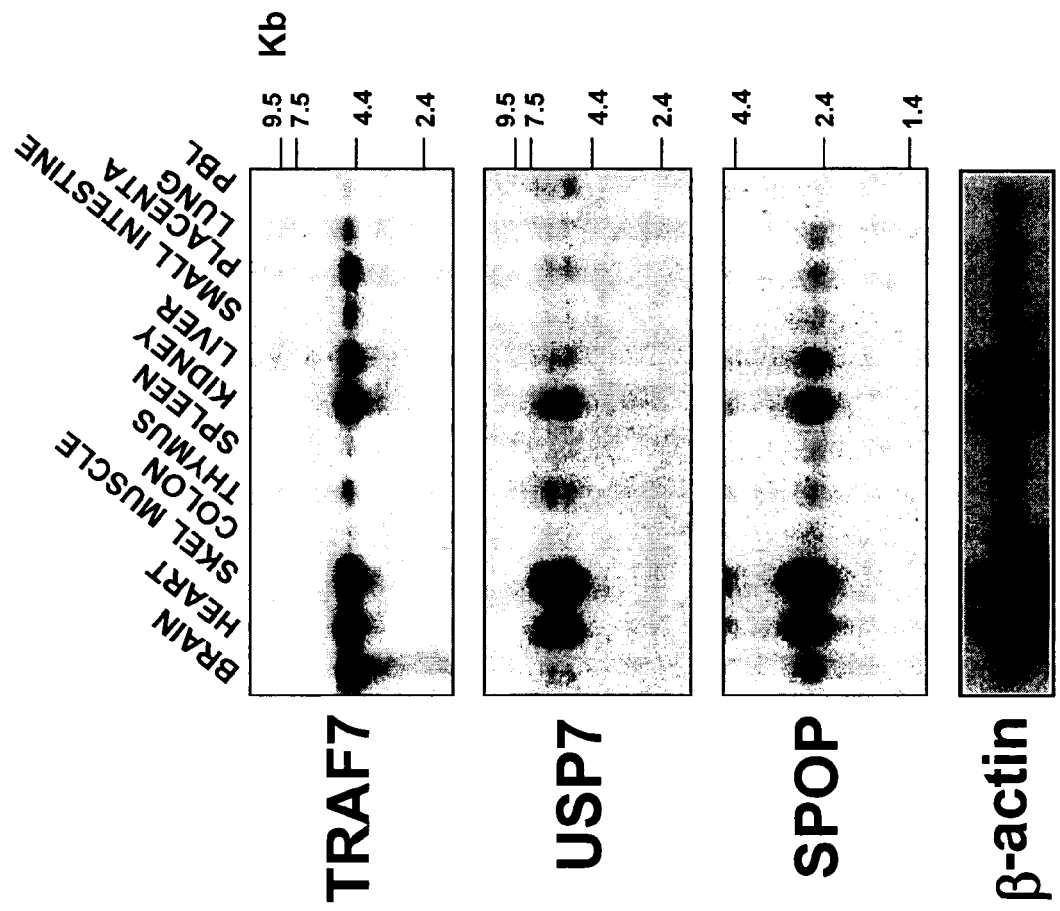
FIG. 4 shows Northern blot analysis of the mRNA levels of TRAF7, USP7 and SPOP in human tissues. Northern blot analyses were performed using the human 12 lane multiple tissue northern blot (MTN; Clontech; Palo Alto Calif.), as recommended by the manufacturer. The TRAF domains of TRAF7, USP7 and SPOP, as well as actin as a control, were labeled with $^{32}$P-cytidine using a nick translation assay kit.

As shown in FIG. 4, the TRAF7 probe hybridized to mRNA of about 5 kb. TRAF7 mRNA was most highly expressed in brain, heart, skeletal muscle, kidney, liver and placenta. TRAF7 was expressed at a lower level in thymus, small intestine, lung, spleen, PBL and colon.

USP7, also known as HAUSP, was expressed as a doublet of about 7 and 5.5 kb. USP7 was most highly expressed in heart, skeletal muscle, and kidney, with lower expression in brain, thymus, liver, placenta and PBLs, and lowest expression, barely detectable, in colon, spleen, small intestine and lung.

SPOP was expressed as mRNA of about 2.6 kb. SPOP was most highly expressed in heart and skeletal muscle, with lower expression in kidney and liver, and even lower expression in brain, skeletal muscle, colon, thymus, small intestine, placenta, lung, and PBLs.

III. Binding to the TNF-Receptor Family

For GST-fusion protein production, PGEX-plasmids were transformed into competent XL-1 blue bacteria cells and grown in LB medium and induced at an $A_{600}$=1.0 with 1 mM isopropyl-1-thio-β-D-galactopyranoside for 4 h at 25° C. Cells were then recovered and resuspended in PBS containing 1 mM dithiothreitol, 1 mM phenyl-methyl-sulphonyl-fluoride and 100 μg/ml lysozyme and lysed by sonication. The GST-TRAF2 (263–501), (GST-HAUSP (SEQ ID NO: 8), GST-SPOP (SEQ ID NO: 10) and GST-TRAF7 (SEQ ID NO: 12) proteins were purified from bacterial lysates by affinity chromatography using glutathione-Sepharose (Amersham Pharmacia Biotech). The resins were then washed with PBS containing 1 mM dithiothreitol until the $OD_{280nm}$ reached <0.01.

Plasmids pGEX-TRAF2(263–501), pGEX-CD40(ct), pGEX-Fas(ct), pGEX-LTβR(ct), pGEX-DR4(ct) and PGEX-NGFR(ct) have been previously described (Leo et al., 1999, JBC 274, 22414; Sato et al., 1995, FEBS lett. 358 113; Crowe et al., J Exp Med 1995, 181, 1205; McFarlane et al., J Biol Chem 1997, 272, 25417; Rabizadeh et al., Proc Natl Acad Sci USA 1994, 91, 10703). Plasmid pGEX-TNF-R2(ct) was kindly provided by Dr. C. Ware (La Jolla Institute for Allergy and Immunology).

In vitro GST-protein binding assays were performed as previously described (Hanada, M., Aime-Sempe, C., Sato, T. and Reed, J C. 1995, JBC 270, 11962–11968; Sato, T., Irie, S., Kitada, S. and Reed, J C. 1995, Science 268, 411–415; Takayama, S., Sato, T., Krajewski, S., Kochel, C., Irie, S., Millan, J. and Reed, J C. 1995, Cell 80, 279–284, Leo et al., 1999, JBC 274, 22414). Briefly, ($^{35}$S)-methionine labeled GST-fused TNF family receptors FAS(ct), TNF-R2(ct), CD40(ct), LTβR(ct), NGFRp75(ct) and DR4(ct) were produced by in vitro translation using the TnT coupled reticulocyte system following the manufacturer indications (Promega Inc.). Equal amounts of each labeled protein (2–6 μl lysate) were then diluted with 250 μl of binding buffer (142 mM KCl, 5 mM MgCl2, 10 mM Hepes pH 7.4, 0.2% Nonidet-P40, 0.5 mM dithiothreitol, 1 mM EGTA, 0.5 mM phenyl-methyl-sulphonyl-fluoride and a mixture of other protease inhibitors (Boehringer 1697498) and incubated with the GST-protein resins (0.25 μg protein) at 4° C. for 2 h. The resins were then extensively washed with binding buffer and the GST-protein binding complexes were eluted with buffer containing 50 mM Tris-HCl pH 8, 1 mM dithiothreitol and 100 mM glutathione and analyzed by SDS-PAGE and fluorography.

Figure 5:
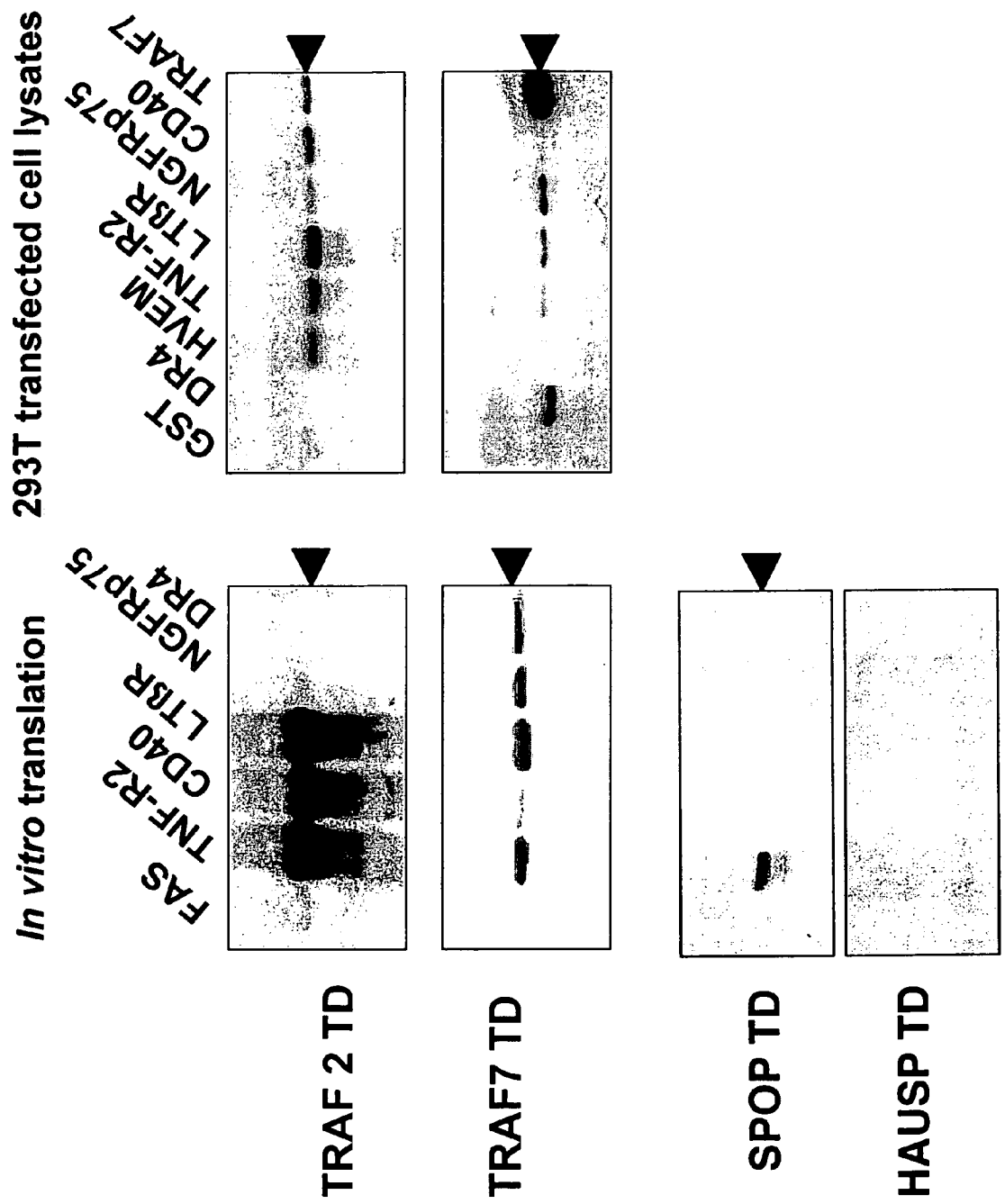
FIG. 5 shows an analysis of the binding of the invention TRAF-protein-binding-domains (TPBDs) to different members of the TNF receptor family. In vitro binding assay results of the cytosolic domains of selected members of the TNF-R family are presented. GST-Fas(ct), GST-TNF-R2 (ct), GST-CD40(ct), GST-LTβR(ct), GST-NGFR(ct) and GST-DR4(ct) immobilized on glutathione-Sepharose were incubated with in vitro translated ($^{35}$)S-TRAF2, -SPOP, -HAUSP, and -TRAF7 TRAF domains. Alternatively, TRAF domains of TRAF7 or TRAF2 were expressed in 293 cells. Bound TRAF proteins were detected by SDS-PAGE and fluorography.

The results of the binding assay are shown in FIG. 5. In vitro protein binding assays were performed by in vitro translating TRAF2 or the TRAF domain of TRAF7 in the presence of $^{35}$S-L-methionine in reticulocyte lysates, as described above, or following in vivo overexpression of TRAF2 or the TRAF domain of TRAF7 by transfection of 293T cells. Equal volumes of the in vitro translation mixtures (10 μl) were incubated with GST-fusion proteins containing the cytosolic domains of different members of the TNF-R family (1 μg)(FAS, TNF-R2, CD40, LTβR, NGFRp75, and DR4) immobilized on glutathione-Sepharose. For TRAF domain protein expression in vivo, 293T lysates (50 μl) were incubated with GST-fusion proteins (1 μg) containing the cytosolic domains of the TNF-R family members DR4, HVEM, TNF-R2, LTβR, NGFRp75, CD40, and TRAF7 and then immobilized on glutathione-Sepharose. Control GST and other GST control proteins were included in all assays After washing, bound proteins were analyzed by SDS-PAGE followed by fluorography for binding assays using in vitro translated proteins. For transfected 293 cells, samples were immunoblotted using anti-TRFA2 or anti-Myc antibodies to detect TRAF2 or TRAF7 TD binding, respectively. Bound proteins were then detected by standard chemiluminescence assay (ECL; Amersham; Piscataway N.J.).

As shown in FIG. 5, three TNF family receptors interacted with the GST-fused TRAF domain of TRAF2: TNF-R2, CD40 and LTβR. However, FAS, NGFRp75 and DR4 did not appreciably interact with the TRAF domain of TRAF2. In contrast, the GST-SPOP fusion protein showed significant interaction with only one of these six receptors, TNF-R2; and GST-HAUSP did not significantly interact with any of the six receptors. In contrast, GST-TRAF7 binds TNF-R2, CD40 (albeit weakly), LTβR, NRFRp75 and DR4. This result shows that invention TPBDs SPOP (SEQ ID NO: 10) and HAUSP (SEQ ID NO: 8) can demonstrate higher selectivity in receptor binding than the TRAF domain of TRAF2 and the invention TPBD of TRAF7 (SEQ ID NO:12).

In cell lysates of 293 cells transfected with TRAF2 or the TRAF domain of TRAF7, binding was observed with several TNF-R family members. TRAF2 interacted with HVEM, TNF-R2, LTβR, CD40 and TRAF7, with low binding activity also observed with NGFRp75. The TRAF domain of TRAF7 interacted with DR4, LTβR, and NGFRp75, with strongest binding observed with TRAF7. A faint band of TRAF7 was also observed to interact with TNF-R2 under these conditions, but no binding of TRAF7 to CD40 or HVEM was detected. Therefore, TRAF7 has strong binding activity with itself.

IV. Binding to TRAF Family Proteins

The above described GST-HAUSP and GST-SPOP, and GST-TRAF7 were produced and purified using the above described procedure.

Plasmids containing cDNAs encompassing the complete open reading frames of hTRAF 1 (pSG5-TRAF 1), hTRAF 2 (pcDNA3-HA-TRAF2), hTRAF3 (pbluscriptKS-TRAF3b), hTRAF4 (pcDNA3-HA-TRAF4), hTRAF5 (pcDNA3-Flag-TRAF5) and hTRAF6 (pcDNA3-myc-TRAF6) have been previously described (Sato et al., 1995, FEBS lett. 358, 113; Nakano et al., 1996, JBC 271, 14661; Mosialos et al., 1995, Cell 80, 389; Krajewska et al., 1998, Am. J. Pathol. 152, 1549; Leo et al., 1999, JBC 274, 22414; Song and Donner. 1995, Biochem. J. 309, 825; Rothe et al., 1995, Cell 78, 281).

In vitro translated TRAF1, TRAF2, TRAF3, TRAF4, TRAF5, TRAF6, full-length I-TRAF (Rothe et al., Proc. Natl. Acad. Sci. USA 93:8241–8246 (1996)), HAUSP (1–213, SEQ ID NO:8), SPOP (1–180, SEQ ID NO:10) and TRAF7 (282–435, SEQ ID NO:12) were incubated with the GST-protein resins using the previously described method.

The resultant images showed that the GST-fused TPBD of TRAF7 (SEQ ID NO: 12) interacted with all previously identified TRAF proteins, TRAFS1–6, and with I-TRAF (see FIG. 6). Additionally, the TPBD of TRAF7 showed an ability to self-associate. The GST-fused TPBD of HAUSP (SEQ ID NO: 8) also was able to interact with all previously known TRAF proteins, although somewhat weakly with TRAF3, and weakly with I-TRAF. However, HAUSP did not demonstrate an ability to self-associate. In contrast, the GST-fused TPBD of SPOP (SEQ ID NO: 10) demonstrated a higher selectivity, having significant interactions with only TRAF1 and TRAF6, and no ability to self-associate. Interestingly, no heterologous interaction between invention TPBDs (i.e., HAUSP:SPOP, HAUSP:TRAF7 and SPOP:TRAF7) were observed.

V. Reporter Gene Assays 293T cells were obtained from ATCC (Rockville, Mass.) and cultured in Dulbecco modified Eagle's-high glucose medium (Life technology, Inc) supplemented with 10% FCS (Hyclone, Utah), 1 mM glutamine and antibiotics. The promoter-containing reporter gene plasmids pUC13-4xN-FkB-luc (containing 4 tandem HIV-NFκB response elements and the minimal fos promoter) and pCMV-β-galactosidase has been previously described (Miyashita and Reed, 1995, Cell 80, 293; Lin and Stavnezer, 1996, MCB 16, 4591).

For NF-κB reporter gene assays, 293T cells were calcium phosphate-transfected with 12 µg DNA, including 3.5 µg of either pcDNA3-myc-hTRAF2, pcDNA3-myc-hTRAF5 or pcDNA3-myc-hTRAF6, in combination with either 3.5 or 7 µg of control plasmid, pcDNA3-myc-HAUSP (1–213, SEQ ID NO: 8), pcDNA3-myc-SPOP (1–180, SEQ ID NO: 10) or pcDNA3-myc-TRAF7 (282–435, SEQ ID NO: 12) at 60% confluency in 6-well plates in duplicate, except in the case of TRAF5 in which only 7 µg of pcDNA3-myc-HAUSP or pcDNA3-myc-TRAF7 were transfected. In the case of SPOP, only 3.5 µg of either pcDNA3-myc-hTRAF6 was used. Also transfected were a total of 0.5 µg pUC13-4xNFκB-luc plasmid and 1 µg pCMV-β-galactosidase plasmid. After 36 h, cells were lysed with 0.5 ml of Promega lysis buffer. The luciferase activity from 10 µl of each cell lysate was determined using the Luciferase assay system from Promega, following the manufacturer protocol, and read using a luminometer (EG&G Berthold). The luciferase activity was normalized relative to β-galactosidase activity (Miyashita and Reed, 1995, Cell 80, 293).

Immunobloting was performed as described (Krajewski et al., 1996, Anal. Biochem. 236, 221). Briefly, 5 µl of each cell lysate was analyzed by immunoblotting using anti-TRAF6 or anti-myc antibodies and standard chemiluminiscence methods (Amersham) for detection.

Figure 7A:
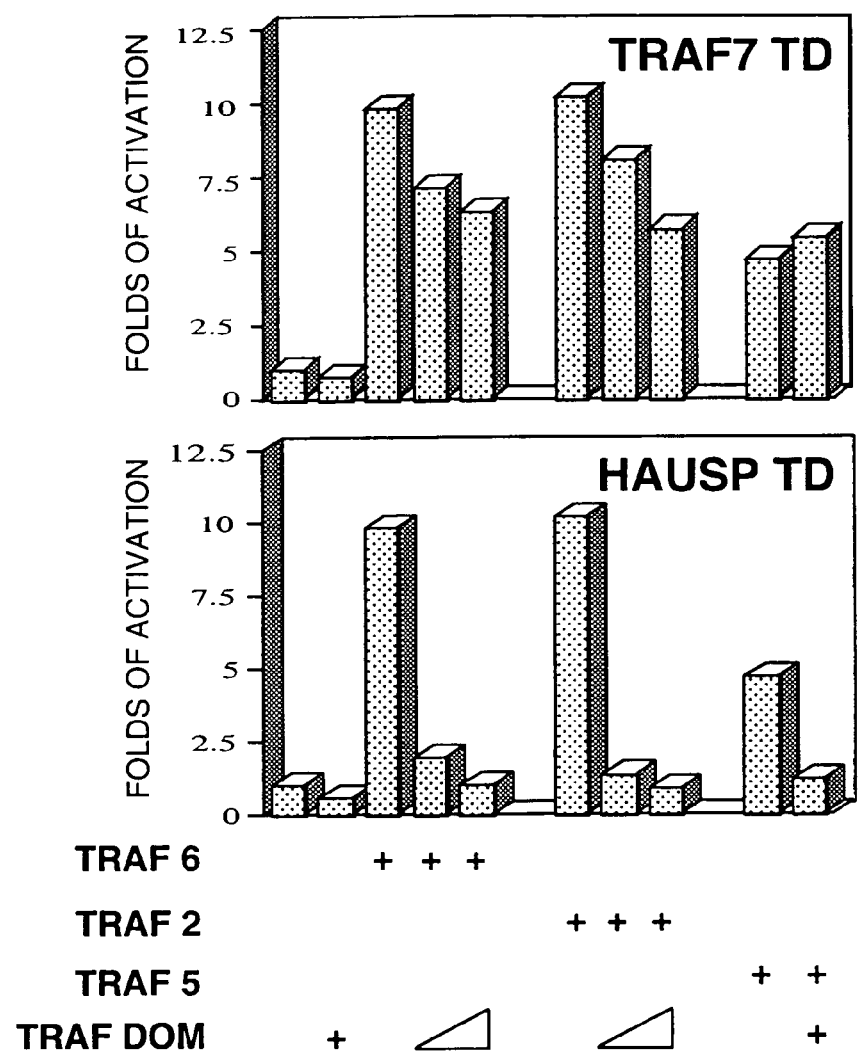
FIG. 7 shows that TPBDs of HAUSP, SPOP and TRAF7 can specifically inhibit the NF-κB activity induced by TRAF containing proteins. In upper panel relative NF-κB activities effected by different TRAF domains are shown. Cells were transfected with control plasmid, pcDNA3-myc-hTRAF6 alone or with 7 μg of either pcDNA3-myc-HAUSP(1–213) or pcDNA3-myc-SPOP(1–180), together with 0.5 μg pUC13-4xNFκB-luc plasmid and 1 μg pCMV-β-galactosidase plasmid, as indicated. Relative NF-κB activity was assessed by luciferase assays, with normalization for β-galactosidase activity. The results are presented as fold of activation relative to the control.
Figure 7B:
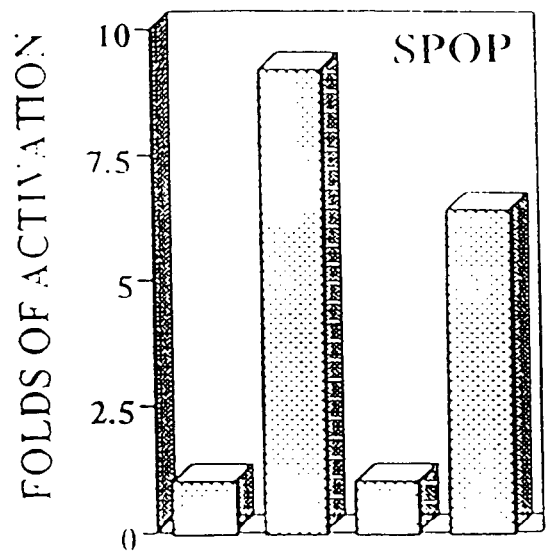

The results show that TPBDs of HAUSP (SEQ ID NO: 8) and SPOP (SEQ ID NO: 10) and TRAF 7 (SEQ ID NO: 12) can inhibit NF-κB activitation induced by TRAF6 (see FIG. 7). In particular, the TPBD of HAUSP is capable of canceling nearly all of the TRAF6-induced increase in NF-κB activitation. Further, the TPBD of HAUSP also strongly inhibits NF-κB activation induced by TRAF 2 and TRAF 5. The TPBD of TRAF 7 also demonstrates the ability to inhibit TRAF 2-mediated NF-κB activation, but actually increases TRAF 5 mediated NF-κB activation.

The activity of various domains of the TRAF proteins USP7 and TRAF7 were further characterized with respect to regulating NFκB activity. The effect of TRAF7 and USP7 in regulating the NFκB activity induced by TRAF2 and TRAF6 in a mammalian cell line was tested. Briefly, 293T cells were transfected in 6 well plates with approximately 10 µg of pcDNA3 control plasmid, 3.5 µg of either pcDNA3-myc-hTRAF6 or pcDNA3-hTRAF2, and 7 µg of any of several TRAF7 or USP7 plasmid constructs containing various domains (see FIG. 8, bottom). The transfections also included 0.5 µg pUC13-4xNFκB-luc plasmid and 1 µg pCMV-β-galactosidase plasmid. Relative NFκB activity was assessed by luciferase assays using 10 µl of each of the cell lysates prepared 36 h after transfection, with normalization for β-galactosidase activity. At least three to eight independent experiments were performed. The results are presented as fold of activation, with one representative experiment shown (FIG. 8).

Figure 8:
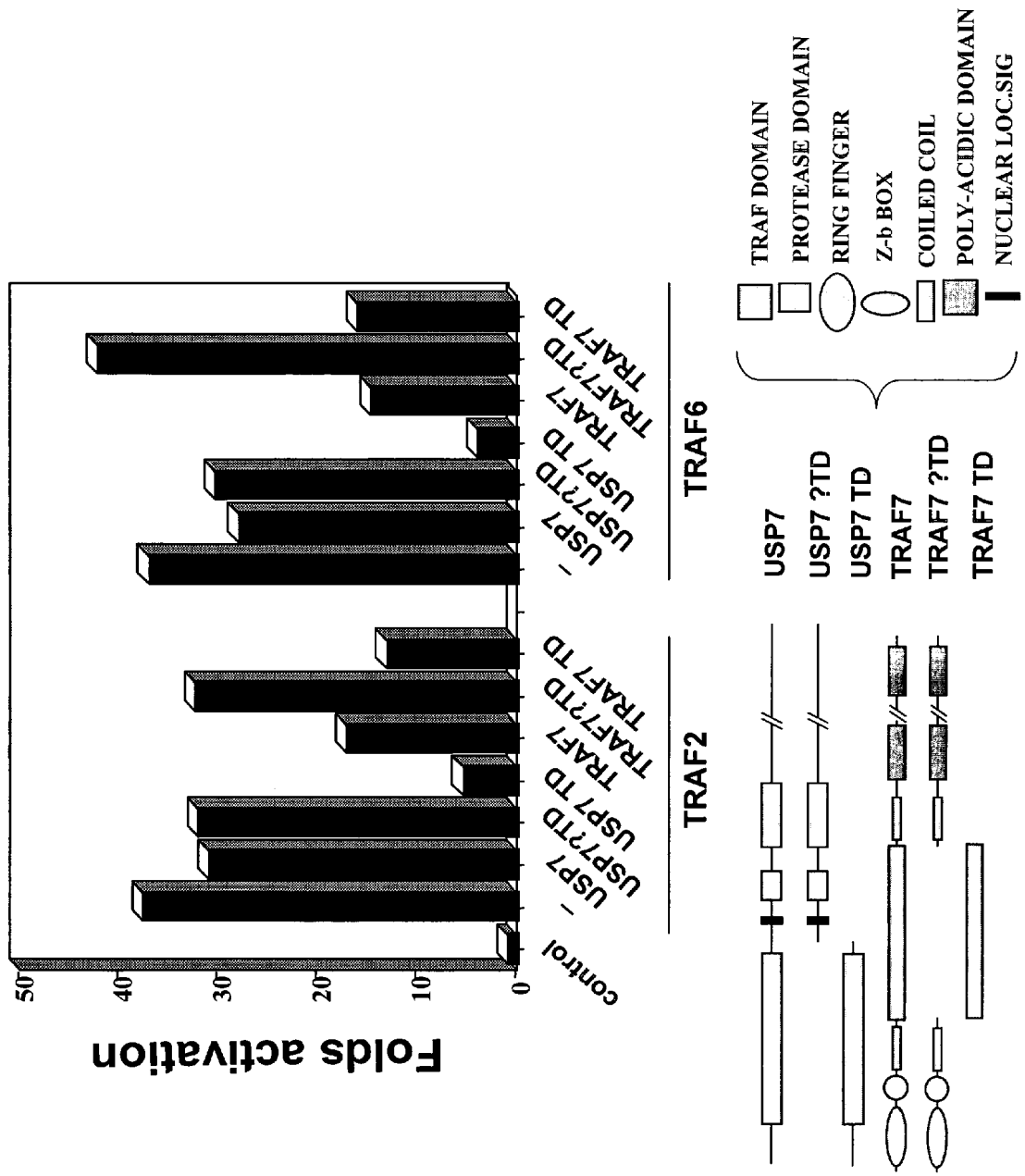
FIG. 8 shows the effect of TRAF7 and USP7 in regulating NFκB activity induced by TRAF2 and TRAF6 in a mammalian cell line.

As shown in FIG. 8, full length USP7 and a USP7 construct lacking the TRAF domain had a slight inhibitory effect on NFκB activity induced by TRAF2 or TRAF6. The USP7 TRAF domain alone strongly inhibited the TRAF2 and TRAF6-induced increase in NFκB activation. In contrast to USP7, full length TRAF7, as well as the TRAF domain of TRAF7 alone, had inhibitory activity for TRAF2 and TRAF6-induced increase in NFκB activation. A TRAF7 mutant construct lacking the TRAF domain did not show any effect on inhibiting the NFκB activation mediated by TRAF2 or TRAF6.

The effect of the TRAF domains of TRAF7, USP7 and SPOP in regulating the NFκB activity induced by TNFα or CD40 overexpression was also tested. 293T cells were transfected in 6 well plates with approximately 10 µg of pcDNA3 control plasmid, 7 µg of either TRAF7 TD, USP7 TD or SPOP TD plasmids, and either no plasmid (TNFα in FIG. 9) or 3.5 µg of pcDNA3-myc-CD40 (CD40 in FIG. 9), together with 0.5 µg pUC13-4xNFkB-luc plasmid and 1 µg pCMV-β-galactosidase plasmid. TNFα treatment was performed by adding 100 ng/ml of TNFα to the cells 12 h before harvesting. Relative NFκB activity was assessed by luciferase assays using 10 µl of each of the cell lysates prepared 36 h after transfection, with normalization for β-galactosidase activity. At least three independent experiments were performed. The results of a representative experiment are presented as fold of activation.

Figure 9:
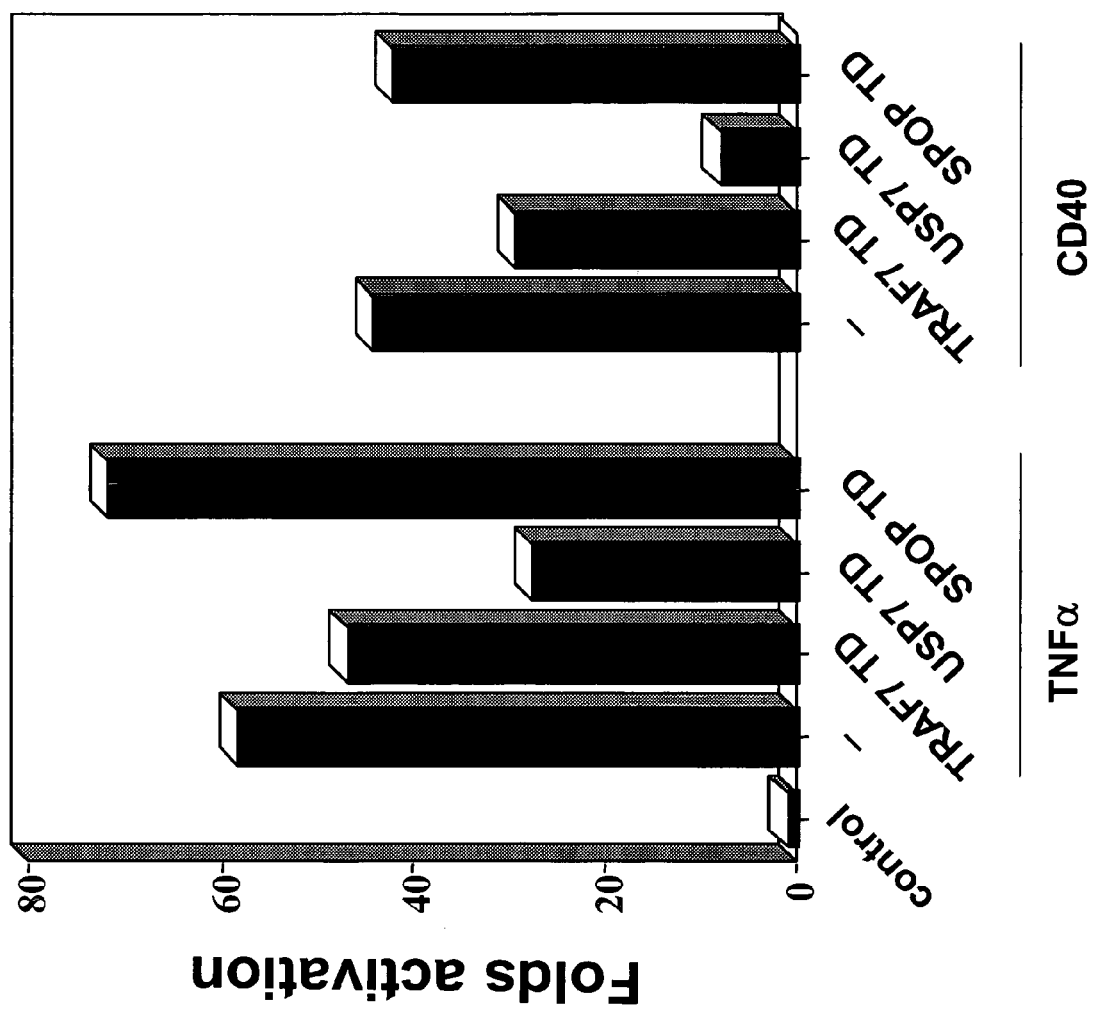
FIG. 9 shows the effect of the TRAF domains of TRAF7, USP7 and SPOP in regulating the NFκB activity induced by TNFα or CD40 overexpression.

As shown in FIG. 9, the TRAF domain of TRAF7 had some inhibitory activity for activation of NFκB induced by both TNFα and CD40 overexpression. The TRAF domain of USP7 had even stronger inhibitory activity than the TRAF domain of TRAF7. In contrast, the TRAF domain of SPOP showed essentially no inhibitory activity of NFκB activation by either TNFα or CD40 overexpression.

Regulation by TRAF7 and USP7 of NFκB activation induced by the TRAF-associated protein NIK was also examined. 293T cells were transfected in 6 well plates with approximately 10 μg of pcDNA3 control plasmid, 7 μg of either empty pcDNA3, or pcDNA3-myc-containing TRAF7, TRAF7 TD, USP7 TD or SPOP TD plasmids, and 3.5 μg of pcDNA3-Flag-NIK, together with 0.5 μg pUC13-4xNFκB-luc plasmid and 1 μg pCMV-β-galactosidase plasmid. Relative NFκB activity was assessed by luciferase assays using 10 μl of each of the cell lysates prepared 36 h after transfection, with normalization for β-galactosidase activity. At least three independent experiments were performed. The results of a representative experiment are presented as fold of activation (FIG. 10).

Figure 10:
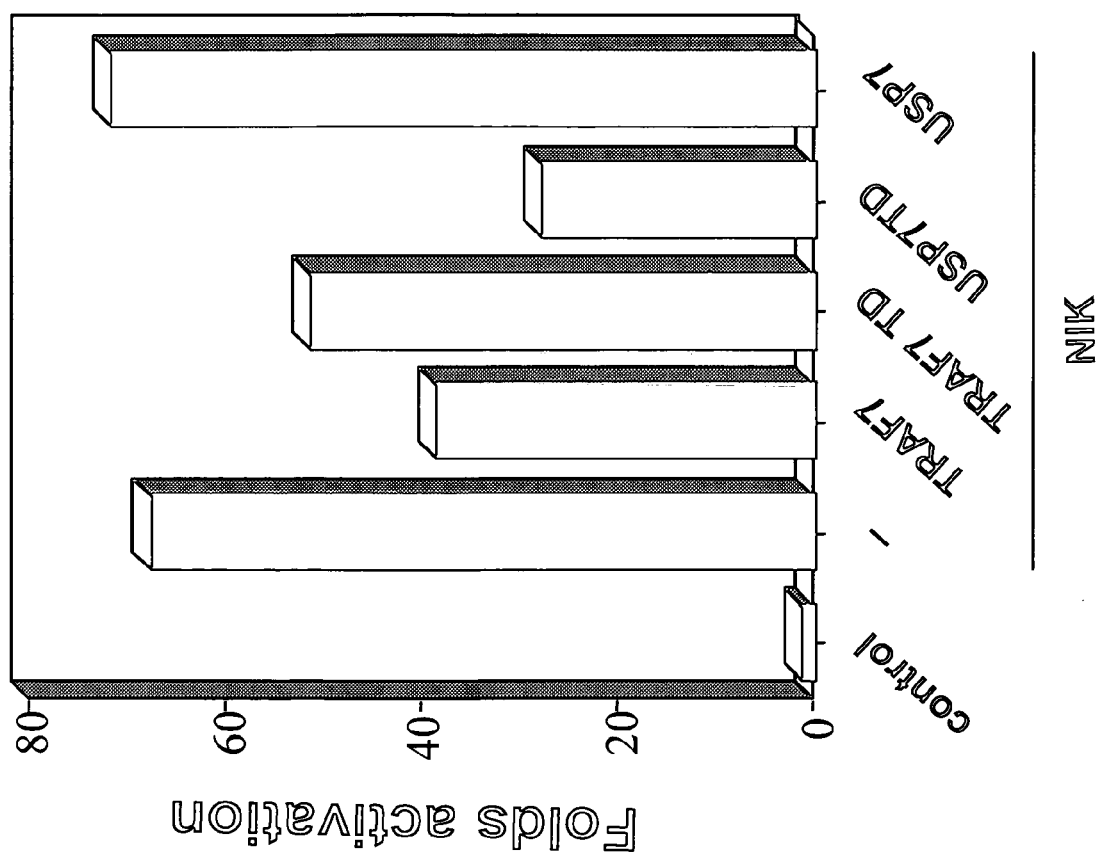
FIG. 10 shows regulation of NIK induced NFκB activation by TRAF7 and USP7.

As shown in FIG. 10, NIK induced NFκB activation can be partially regulated by TRAF7 and USP7. Both TRAF7 and the TRAF domain of TRAF7 partially inhibited NIK-induced NFκB activation. USP7 TRAF domain also partially inhibited NIK induced NFκB activation, although the full length USP7 did not inhibit NIK-induced NFκB activation (FIG. 10)

VI. Subcellular Localization of Domains of TPBDs

To test the function of various domains in subcellular localization, TRAF7 and USP7 deletion mutants were constructed. For TRAF7 deletion mutants, Cos7 cells were transfected with Lipofectamin plus (Life Technologies; Rockville Md.) and a total of 3 μg of plasmid. The TRAF7 deletion mutants (shown in FIG. 11) were constructed as Myc fusion proteins. 24 hours after transfection, cells were plated onto poly-lysinated cover-glasses and allowed to settle for 24 h more. Cells were fixed with methanol-acetone (50% each). After blocking, cells were stained with anti-myc mAb (Santa Cruz Biotechnology; Santa Cruz Calif.) and a secondary FITC-labelled rabbit anti-mouse Ig (Dako; Carpinteria Calif.). Analysis was performed using a Bio-Rad confocal microscope (BioRad; Hercules Calif.).

Figure 11:
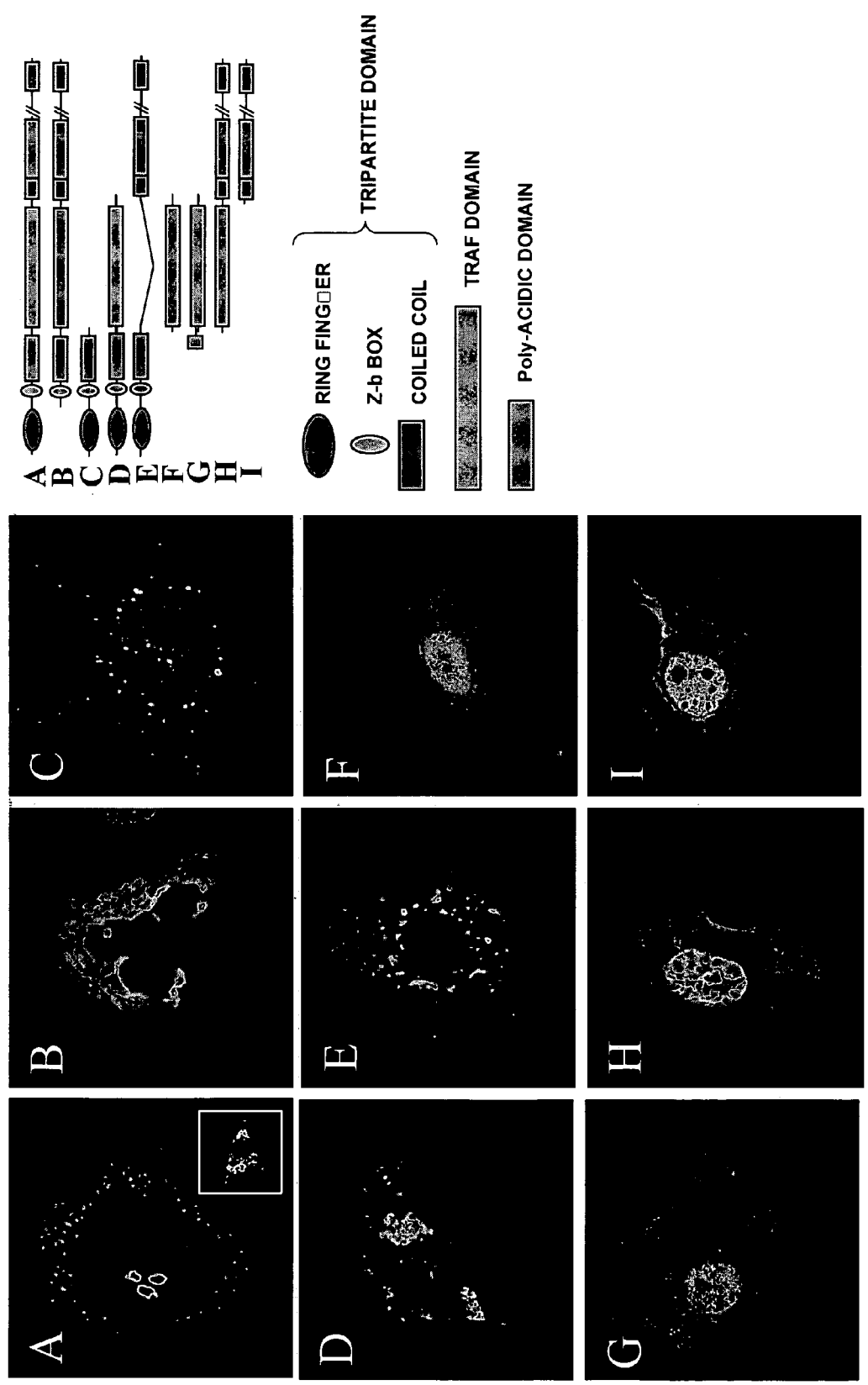
FIG. 11 shows the subcellular localization of different TRAF7 deletion mutants.

FIG. 11 shows the subcellular localization of TRAF7 and different deletion mutants of the molecule. A scheme of the different TRAF7 mutants analyzed is also shown. TRAF7 localizes in cytosolic corpuscles, which can appear as individual dots (panel A) or as large aggregates (A, small panel). Deletion mutants of TRAF7 lacking the RING finger domain (B), containing only the tripartite domain (C), lacking the poly-acidic region (D), or lacking the TRAF domain (E) have a similar subcellular localization as the full length TRAF7. In contrast, the TRAF domain alone (F) or the TRAF domain containing also the leucine zippers (G) did not show this particular subcellular localization, having a diffuse cytosolic localization. The C-terminal region of the molecule containing the TRAF domain and the poly-acidic region (H) or the poly-acidic region alone (I) have a similar diffuse cytosolic localization, although in this case they appear to be also located in the nucleus. These results indicate that the region of TRAF7 which is determinant for its subcellular localization can be mapped to the Z-b box and the first coiled coil.

For characterizing the localization of USP7 deletion mutants, Cos7 cells were transfected with Lipofectamin plus (Life Technologies) and a total of 3 μg of plasmid. USP7 full length and deletion mutants were constructed as Myc fusion proteins. The USP7 deletion mutants tested were a mutant lacking the TRAF domain and a mutant containing USP7 TRAF domain. 24 hours after transfection, cells were plated onto poly-lysinated cover-glasses and allowed to settle for 24 h more. Cells were fixed with methanol-acetone (50% each). After blocking, cells were stained with anti-myc mAb (Santa Cruz Biotech.) and a secondary FITC-labelled rabbit anti-mouse Ig (Dako). Analysis was performed using a Bio-Rad confocal microscope. Two representative examples of each construct are shown.

Figure 12:
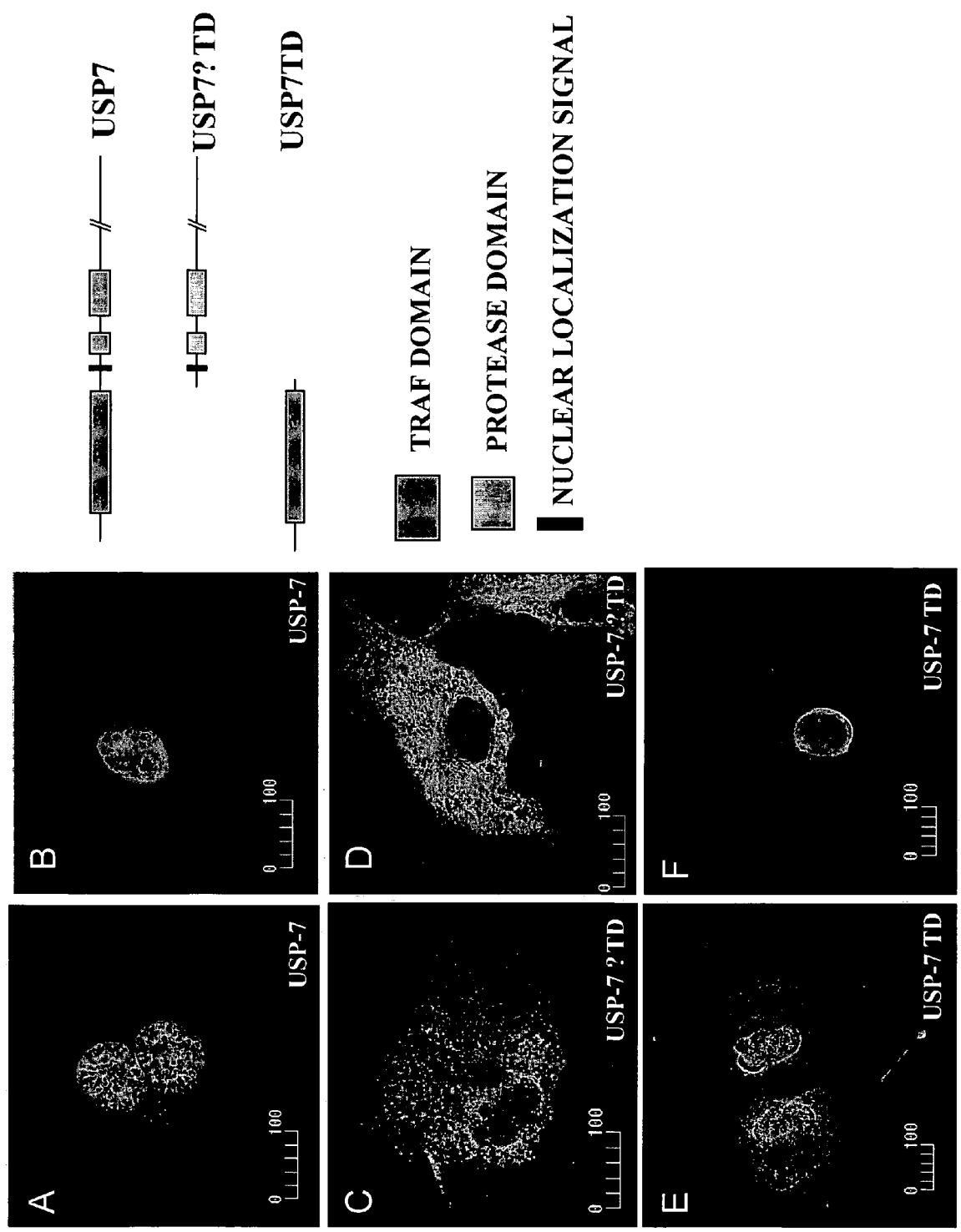
FIG. 12 shows the subcellular localization of different domains of USP7.

FIG. 12 shows the subcellular localization of USP7 full length (A and B), a deletion mutant of USP7 lacking the TRAF domain (C and D) and USP7 TRAF domain (E and F). USP7 is mainly located in the nucleus, although some cytosolic staining can also be observed in some cells. The deletion mutant lacking the TRAF domain is completely excluded from the nucleus, even when it still contains the nuclear localization signal. Finally, the TRAF domain of USP7 appears to have a diffuse localization, with a larger concentration in the perinuclear region. These results indicate that the TRAF domain of USP7 is necessary, but not sufficient, to target this molecule to the nucleus.

Although the invention has been described with reference to the examples above, it should be understood that various modifications can be made without departing from the spirit of the invention. Accordingly, the invention is limited only by the following claims.

The invention claimed is:

1. An isolated anti-TPBD antibody having specific reactivity with SEQ ID NO:24, wherein said antibody inhibits the association of said TPBD with a TNF family receptor, TRAF protein or a TRAF-associated protein.

2. The isolated anti-TPBD antibody of claim 1, wherein said TNF family receptor is TNF-R2, said TRAF protein is human TRAF6 and said TRAF-associated protein is I-TRAF.

3. The isolated anti-TPBD antibody of claim 1, wherein said TNF family receptor is CD40, said TRAF protein is human TRAF2 and said TRAF-associated protein is I-TRAF.

4. An antibody according to claim 1, wherein said antibody is a monoclonal antibody.

5. A cell line producing the monoclonal antibody of claim 4.

6. The cell line of claim 5, wherein said cell line is a hybridoma.

7. An antibody according to claim 1, wherein said antibody is a polyclonal antibody.

8. An isolated anti-TPBD antibody having specific reactivity with the TPBD amino acid sequence consisting of SEQ ID NO:24.

9. An antibody according to claim 8, wherein said antibody is a monoclonal antibody.

10. A cell line producing the monoclonal antibody of claim 9.

11. An antibody according to claim 8, wherein said antibody is a polyclonal antibody.

12. A cell line producing a monoclonal antibody having specific reactivity with a TPBD amino acid sequence selected from the group consisting of SEQ ID NOS: 12, 24 and 25.

13. The cell line of claim 12, wherein said antibody has specific reactivity with SEQ ID NO:12.

14. The cell line of claim 13, wherein said cell line is a hybridoma.

15. The cell line of claim 12, wherein said antibody has specific reactivity with SEQ ID NO:24.

16. The cell line of claim 15, wherein said cell line is a hybridoma.

17. The cell line of claim 12, wherein said antibody has specific reactivity with SEQ ID NO:25.

18. The cell line of claim 17, wherein said cell line is a hybridoma.

19. A cell line producing a monoclonal antibody having specific reactivity with a TPBD amino acid sequence selected from the group consisting of SEQ ID NOS: 12, 24 and 25, wherein said antibody inhibits the association of said TPBD with a TNF family receptor, TRAF protein or a TRAF-associated protein.

20. The cell line of claim 19, wherein said antibody has specific reactivity with SEQ ID NO:12.

21. The cell line of claim 20, wherein said cell line is a hybridoma.

22. The cell line of claim 19, wherein said antibody has specific reactivity with SEQ ID NO:24.

23. The cell line of claim 22, wherein said cell line is a hybridoma.

24. The cell line of claim 19, wherein said antibody has specific reactivity with SEQ ID NO:25.

25. The cell line of claim 24, wherein said cell line is a hybridoma.

* * * * *

SEQUENCE LISTING

```
<160> NUMBER OF SEQ ID NOS: 32

<210> SEQ ID NO 1
<211> LENGTH: 4022
<212> TYPE: DNA
<213> ORGANISM: Homo sapiens
<220> FEATURE:
<221> NAME/KEY: CDS
<222> LOCATION: (200)..(3505)

<400> SEQUENCE: 1
gtacgtgcgc gtctccctgc cgccgccgcc gcccgccgcg ggccgcccg gggccgccgt      60
```

-continued

```
cgccgacgac gcgcgggagg aggaggagga ggccgccccg ccgccgccgc cgccgccgcc      120
gccccggctc gccgccgccc gcccgccggg ctcgcagccc cggcccccgg ccgcaggcga      180
ggcccaggcc gcggccgac atg aac cac cag cag cag cag cag cag cag aaa      232
                     Met Asn His Gln Gln Gln Gln Gln Gln Gln Lys
                      1               5                  10 gcg ggc gag cag cag ttg agc gag ccc gag gac atg gag atg gaa gcg       280
Ala Gly Glu Gln Gln Leu Ser Glu Pro Glu Asp Met Glu Met Glu Ala
             15                  20                  25 gga gat aca gat gac cca cca aga att act cag aac cct gtg atc aat       328
Gly Asp Thr Asp Asp Pro Pro Arg Ile Thr Gln Asn Pro Val Ile Asn
         30                  35                  40 ggg aat gtg gcc ctg agt gat gga cac aac acc gcg gag gag gac atg       376
Gly Asn Val Ala Leu Ser Asp Gly His Asn Thr Ala Glu Glu Asp Met
 45                  50                  55 gag gat gac acc agt tgg cgc tcc gag gca acc ttt cag ttc act gtg       424
Glu Asp Asp Thr Ser Trp Arg Ser Glu Ala Thr Phe Gln Phe Thr Val
 60                  65                  70                  75 gag cgc ttc agc aga ctg agt gag tcg gtc ctt agc cct ccg tgt ttt       472
Glu Arg Phe Ser Arg Leu Ser Glu Ser Val Leu Ser Pro Pro Cys Phe
             80                  85                  90 gtg cga aat ctg cca tgg aag att atg gtg atg cca cgc ttt tat cca       520
Val Arg Asn Leu Pro Trp Lys Ile Met Val Met Pro Arg Phe Tyr Pro
         95                 100                 105 gac aga cca cac caa aaa agc gta gga ttc ttt ctc cag tgc aat gct       568
Asp Arg Pro His Gln Lys Ser Val Gly Phe Phe Leu Gln Cys Asn Ala
        110                 115                 120 gaa tct gat tcc acg tca tgg tct tgc cat gca caa gca gtg ctg aag       616
Glu Ser Asp Ser Thr Ser Trp Ser Cys His Ala Gln Ala Val Leu Lys
125                 130                 135 ata ata aat tac aga gat gat gaa aag tcg ttc agt cgt cgt att agt       664
Ile Ile Asn Tyr Arg Asp Asp Glu Lys Ser Phe Ser Arg Arg Ile Ser
140                 145                 150                 155 cat ttg ttc ttc cat aaa gaa aat gat tgg gga ttt tcc aat ttt atg       712
His Leu Phe Phe His Lys Glu Asn Asp Trp Gly Phe Ser Asn Phe Met
             160                 165                 170 gcc tgg agt gaa gtg acc gat cct gag aaa gga ttt ata gat gat gac       760
Ala Trp Ser Glu Val Thr Asp Pro Glu Lys Gly Phe Ile Asp Asp Asp
         175                 180                 185 aaa gtt acc ttt gaa gtc ttt gta cag gcg gat gct ccc cat gga gtt       808
Lys Val Thr Phe Glu Val Phe Val Gln Ala Asp Ala Pro His Gly Val
        190                 195                 200 gcg tgg gat tca aag aag cac aca ggc tac gtc ggc tta aag aat cag       856
Ala Trp Asp Ser Lys Lys His Thr Gly Tyr Val Gly Leu Lys Asn Gln
205                 210                 215 gga gcg act tgt tac atg aac agc ctg cta cag acg tta ttt ttc acg       904
Gly Ala Thr Cys Tyr Met Asn Ser Leu Leu Gln Thr Leu Phe Phe Thr
220                 225                 230                 235 aat cag cta cga aag gct gtg tac atg atg cca acc gag ggg gat gat       952
Asn Gln Leu Arg Lys Ala Val Tyr Met Met Pro Thr Glu Gly Asp Asp
             240                 245                 250 tcg tct aaa agc gtc cct tta gca tta caa aga gtg ttc tat gaa tta      1000
Ser Ser Lys Ser Val Pro Leu Ala Leu Gln Arg Val Phe Tyr Glu Leu
         255                 260                 265 cag cat agt gat aaa cct gta gga aca aaa aag tta aca aag tca ttt      1048
Gln His Ser Asp Lys Pro Val Gly Thr Lys Lys Leu Thr Lys Ser Phe
        270                 275                 280 ggg tgg gaa act tta gat agc ttc atg caa cat gat gtt cag gag ctt      1096
Gly Trp Glu Thr Leu Asp Ser Phe Met Gln His Asp Val Gln Glu Leu
```

-continued

|  |  |  |  |  |  |  |  |  |  |  |  |  |  |  |  |
|---|---|---|---|---|---|---|---|---|---|---|---|---|---|---|---|
|  |  | 285 |  |  |  |  | 290 |  |  |  |  | 295 |  |  |  |

```
tgt cga gtg ttg ctc gat aat gtg gaa aat aag atg aaa ggc acc tgt    1144
Cys Arg Val Leu Leu Asp Asn Val Glu Asn Lys Met Lys Gly Thr Cys
300             305                 310                 315 gta gag ggc acc ata ccc aaa tta ttc cgc ggc aaa atg gtg tcc tat    1192
Val Glu Gly Thr Ile Pro Lys Leu Phe Arg Gly Lys Met Val Ser Tyr
        320                 325                 330 atc cag tgt aaa gaa gta gac tat cgg tct gat aga aga gaa gat tat    1240
Ile Gln Cys Lys Glu Val Asp Tyr Arg Ser Asp Arg Arg Glu Asp Tyr
            335                 340                 345 tat gat atc cag cta agt atc aaa gga aag aaa aat ata ttt gaa tca    1288
Tyr Asp Ile Gln Leu Ser Ile Lys Gly Lys Lys Asn Ile Phe Glu Ser
                350                 355                 360 ttt gtg gat tat gtg gca gta gaa cag ctc gat ggg gac aat aaa tac    1336
Phe Val Asp Tyr Val Ala Val Glu Gln Leu Asp Gly Asp Asn Lys Tyr
365                 370                 375 gac gct ggg gaa cat ggc tta cag gaa gca gag aaa ggt gtg aaa ttc    1384
Asp Ala Gly Glu His Gly Leu Gln Glu Ala Glu Lys Gly Val Lys Phe
380                 385                 390                 395 cta aca ttg cca cca gtg tta cat cta caa ctg atg aga ttt atg tat    1432
Leu Thr Leu Pro Pro Val Leu His Leu Gln Leu Met Arg Phe Met Tyr
            400                 405                 410 gac cct cag acg gac caa aat atc aag atc aat gat agg ttt gaa ttc    1480
Asp Pro Gln Thr Asp Gln Asn Ile Lys Ile Asn Asp Arg Phe Glu Phe
                415                 420                 425 cca gag cag tta cca ctt gat gaa ttt ttg caa aaa aca gat cct aag    1528
Pro Glu Gln Leu Pro Leu Asp Glu Phe Leu Gln Lys Thr Asp Pro Lys
                430                 435                 440 gac cct gca aat tat att ctt cat gca gtc ctg gtt cat agt gga gat    1576
Asp Pro Ala Asn Tyr Ile Leu His Ala Val Leu Val His Ser Gly Asp
445                 450                 455 aat cat ggt gga cat tat gtg gtt tat cta aac ccc aaa ggg gat ggc    1624
Asn His Gly Gly His Tyr Val Val Tyr Leu Asn Pro Lys Gly Asp Gly
460                 465                 470                 475 aaa tgg tgt aaa ttt gat gac gac gtg gtg tca agg tgt act aaa gag    1672
Lys Trp Cys Lys Phe Asp Asp Asp Val Val Ser Arg Cys Thr Lys Glu
            480                 485                 490 gaa gca att gag cac aat tat ggg ggt cac gat gac gac ctg tct gtt    1720
Glu Ala Ile Glu His Asn Tyr Gly Gly His Asp Asp Asp Leu Ser Val
                495                 500                 505 cga cac tgc act aat gct tac atg tta gtc tac atc agg gaa tca aaa    1768
Arg His Cys Thr Asn Ala Tyr Met Leu Val Tyr Ile Arg Glu Ser Lys
                510                 515                 520 ctg agt gaa gtt tta cag gcg gtc acc gac cat gat att cct cag cag    1816
Leu Ser Glu Val Leu Gln Ala Val Thr Asp His Asp Ile Pro Gln Gln
525                 530                 535 ttg gtg gag cga tta caa gaa gag aaa agg atc gag gct cag aag cgg    1864
Leu Val Glu Arg Leu Gln Glu Glu Lys Arg Ile Glu Ala Gln Lys Arg
540                 545                 550                 555 aag gag cgg cag gaa gcc cat ctc tat atg caa gtg cag ata gtc gca    1912
Lys Glu Arg Gln Glu Ala His Leu Tyr Met Gln Val Gln Ile Val Ala
            560                 565                 570 gag gac cag ttt tgt ggc cac caa ggg aat gac atg tac gat gaa gaa    1960
Glu Asp Gln Phe Cys Gly His Gln Gly Asn Asp Met Tyr Asp Glu Glu
                575                 580                 585 aaa gtg aaa tac act gtg ttc aaa gta ttg aag aac tcc tcg ctt gct    2008
Lys Val Lys Tyr Thr Val Phe Lys Val Leu Lys Asn Ser Ser Leu Ala
                590                 595                 600 gag ttt gtt cag agc ctc tct cag acc atg gga ttt cca caa gat caa    2056
```

```
Glu Phe Val Gln Ser Leu Ser Gln Thr Met Gly Phe Pro Gln Asp Gln
    605                 610                 615 att cga ttg tgg ccc atg caa gca agg agt aat gga aca aaa cga cca        2104
Ile Arg Leu Trp Pro Met Gln Ala Arg Ser Asn Gly Thr Lys Arg Pro
620                 625                 630                 635 gca atg tta gat aat gaa gcc gac ggc aat aaa aca atg att gag ctc        2152
Ala Met Leu Asp Asn Glu Ala Asp Gly Asn Lys Thr Met Ile Glu Leu
                640                 645                 650 agt gat aat gaa aac cct tgg aca ata ttc ctg gaa aca gtt gat ccc        2200
Ser Asp Asn Glu Asn Pro Trp Thr Ile Phe Leu Glu Thr Val Asp Pro
            655                 660                 665 gag ctg gct gct agt gga gcg acc tta ccc aag ttt gat aaa gat cat        2248
Glu Leu Ala Ala Ser Gly Ala Thr Leu Pro Lys Phe Asp Lys Asp His
        670                 675                 680 gat gta atg tta ttt ttg aag atg tat gat ccc aaa acg cgg agc ttg        2296
Asp Val Met Leu Phe Leu Lys Met Tyr Asp Pro Lys Thr Arg Ser Leu
    685                 690                 695 aat tac tgt ggg cat atc tac aca cca ata tcc tgt aaa ata cgt gac        2344
Asn Tyr Cys Gly His Ile Tyr Thr Pro Ile Ser Cys Lys Ile Arg Asp
700                 705                 710                 715 ttg ctc cca gtt atg tgt gac aga gca gga ttt att caa gat act agc        2392
Leu Leu Pro Val Met Cys Asp Arg Ala Gly Phe Ile Gln Asp Thr Ser
                720                 725                 730 ctt atc ctc tat gag gaa gtt aaa ccg aat tta aca gag aga att cag        2440
Leu Ile Leu Tyr Glu Glu Val Lys Pro Asn Leu Thr Glu Arg Ile Gln
            735                 740                 745 gac tat gac gtg tct ctt gat aaa gcc ctt gat gaa cta atg gat ggt        2488
Asp Tyr Asp Val Ser Leu Asp Lys Ala Leu Asp Glu Leu Met Asp Gly
        750                 755                 760 gac atc ata gta ttt cag aag gat gac cct gaa aat gat aac agt gaa        2536
Asp Ile Ile Val Phe Gln Lys Asp Asp Pro Glu Asn Asp Asn Ser Glu
    765                 770                 775 tta ccc acc gca aag gag tat ttc cga gat ctc tac cac cgc gtt gat        2584
Leu Pro Thr Ala Lys Glu Tyr Phe Arg Asp Leu Tyr His Arg Val Asp
780                 785                 790                 795 gtc att ttc tgt gat aaa aca atc cct aat gat cct gga ttt gtg gtt        2632
Val Ile Phe Cys Asp Lys Thr Ile Pro Asn Asp Pro Gly Phe Val Val
                800                 805                 810 acg tta tca aat aga atg aat tat ttt cag gtt gca aag aca gtt gca        2680
Thr Leu Ser Asn Arg Met Asn Tyr Phe Gln Val Ala Lys Thr Val Ala
            815                 820                 825 cag agg ctc aac aca gat cca atg ttg ctg cag ttt ttc aag tct caa        2728
Gln Arg Leu Asn Thr Asp Pro Met Leu Leu Gln Phe Phe Lys Ser Gln
        830                 835                 840 ggt tat agg gat ggc cca ggt aat cct ctt aga cat aat tat gaa ggt        2776
Gly Tyr Arg Asp Gly Pro Gly Asn Pro Leu Arg His Asn Tyr Glu Gly
    845                 850                 855 act tta aga gat ctt cta cag ttc ttc aag cct aga caa cct aag aaa        2824
Thr Leu Arg Asp Leu Leu Gln Phe Phe Lys Pro Arg Gln Pro Lys Lys
860                 865                 870                 875 ctt tac tat cag cag ctt aag atg aaa atc aca gac ttt gag aac agg        2872
Leu Tyr Tyr Gln Gln Leu Lys Met Lys Ile Thr Asp Phe Glu Asn Arg
                880                 885                 890 cga agt ttt aaa tgt ata tgg tta aac agc caa ttt agg gaa gag gaa        2920
Arg Ser Phe Lys Cys Ile Trp Leu Asn Ser Gln Phe Arg Glu Glu Glu
            895                 900                 905 ata aca cta tat cca gac aag cat ggg tgt gtc cgg gac ctg tta gaa        2968
Ile Thr Leu Tyr Pro Asp Lys His Gly Cys Val Arg Asp Leu Leu Glu
        910                 915                 920
```

-continued

| | |
|---|---|
| gaa tgt aaa aag gcc gtg gag ctt ggg gag aaa gca tca ggg aaa ctt<br>Glu Cys Lys Lys Ala Val Glu Leu Gly Glu Lys Ala Ser Gly Lys Leu<br>925     930     935 | 3016 |
| agg ctg cta gaa att gta agc tac aaa atc att ggt gtt cat caa gaa<br>Arg Leu Leu Glu Ile Val Ser Tyr Lys Ile Ile Gly Val His Gln Glu<br>940     945     950     955 | 3064 |
| gat gaa cta tta gaa tgt tta tct cct gca acg agc cgg acg ttt cga<br>Asp Glu Leu Leu Glu Cys Leu Ser Pro Ala Thr Ser Arg Thr Phe Arg<br>960     965     970 | 3112 |
| ata gag gaa atc cct ttg gac cag gtg gac ata gac aaa gag aat gag<br>Ile Glu Glu Ile Pro Leu Asp Gln Val Asp Ile Asp Lys Glu Asn Glu<br>975     980     985 | 3160 |
| atg ctt gtc aca gtg gcg cat ttc cac aaa gag gtc ttc gga acg ttc<br>Met Leu Val Thr Val Ala His Phe His Lys Glu Val Phe Gly Thr Phe<br>990     995     1000 | 3208 |
| gga atc ccg ttt ttg ctg agg ata cac cag ggc gag cat ttt cga gaa<br>Gly Ile Pro Phe Leu Leu Arg Ile His Gln Gly Glu His Phe Arg Glu<br>1005     1010     1015 | 3256 |
| gtg atg aag cga atc cag agc ctg ctg gac atc cag gag aag gag ttt<br>Val Met Lys Arg Ile Gln Ser Leu Leu Asp Ile Gln Glu Lys Glu Phe<br>1020     1025     1030     1035 | 3304 |
| gag aag ttt aaa ttt gca att gta atg acg ggc cga cac cag tac ata<br>Glu Lys Phe Lys Phe Ala Ile Val Met Thr Gly Arg His Gln Tyr Ile<br>1040     1045     1050 | 3352 |
| aat gaa gac gag tat gaa gta aat ttg aaa gac ttt gag cca cag ccc<br>Asn Glu Asp Glu Tyr Glu Val Asn Leu Lys Asp Phe Glu Pro Gln Pro<br>1055     1060     1065 | 3400 |
| ggt aat atg tct cat cct cgg cct tgg cta ggg ctc gac cac ttc aac<br>Gly Asn Met Ser His Pro Arg Pro Trp Leu Gly Leu Asp His Phe Asn<br>1070     1075     1080 | 3448 |
| aaa gcc cca aag agg agt cgc tac act tac ctt gaa aag gcc att aaa<br>Lys Ala Pro Lys Arg Ser Arg Tyr Thr Tyr Leu Glu Lys Ala Ile Lys<br>1085     1090     1095 | 3496 |
| atc cat aac tgatttccaa gctggtgtgt tcaaggcgag gacggtgtgt<br>Ile His Asn<br>1100 | 3545 |
| gggtggcccc ttaacagcct agaactttgg tgcacgtgcc ctctagccga agtcttcagc | 3605 |
| aagaggattc gctgctggtg ttaattttat tttattgagg ctgttcagtt tggcttctct | 3665 |
| gtatctattg actgcccttt tgagcaaaa tgaagatgtt tttataaagc ttggatgcca | 3725 |
| atgagagtta ttttatggta accacagtgc aaggcaactg tcagcgcaat ggggagaag | 3785 |
| aggttagtgg atcggggtc cctggctcaa ggtctctggg ctgtcccctag tgggcacgag | 3845 |
| tggctcggct gccttcctgg ggtcccgtgc accagccctg cagctagcaa gtcttgtgtt | 3905 |
| taggctcgtc tgacctattt ccttcagtta tactttcaat gaccttttgt gcatctgtta | 3965 |
| aggcaaaaca gagaaactca caacctaata aatagcgctc ttcccttcaa aaaaaaa | 4022 |

<210> SEQ ID NO 2
<211> LENGTH: 1102
<212> TYPE: PRT
<213> ORGANISM: Homo sapiens

<400> SEQUENCE: 2

Met Asn His Gln Gln Gln Gln Gln Gln Lys Ala Gly Glu Gln Gln
1     5     10     15

Leu Ser Glu Pro Glu Asp Met Glu Met Glu Ala Gly Asp Thr Asp Asp
     20     25     30

Pro Pro Arg Ile Thr Gln Asn Pro Val Ile Asn Gly Asn Val Ala Leu

-continued

```
              35                  40                  45
Ser Asp Gly His Asn Thr Ala Glu Glu Asp Met Glu Asp Thr Ser
 50                  55                  60

Trp Arg Ser Glu Ala Thr Phe Gln Phe Thr Val Glu Arg Phe Ser Arg
 65                  70                  75                  80

Leu Ser Glu Ser Val Leu Ser Pro Pro Cys Phe Val Arg Asn Leu Pro
                 85                  90                  95

Trp Lys Ile Met Val Met Pro Arg Phe Tyr Pro Asp Arg Pro His Gln
                100                 105                 110

Lys Ser Val Gly Phe Phe Leu Gln Cys Asn Ala Glu Ser Asp Ser Thr
                115                 120                 125

Ser Trp Ser Cys His Ala Gln Ala Val Leu Lys Ile Ile Asn Tyr Arg
130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Lys Val Thr Phe Glu
                180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
        210                 215                 220

Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Ser Lys Ser Val
                245                 250                 255

Pro Leu Ala Leu Gln Arg Val Phe Tyr Glu Leu Gln His Ser Asp Lys
                260                 265                 270

Pro Val Gly Thr Lys Lys Leu Thr Lys Ser Phe Gly Trp Glu Thr Leu
                275                 280                 285

Asp Ser Phe Met Gln His Asp Val Gln Glu Leu Cys Arg Val Leu Leu
290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
                340                 345                 350

Ser Ile Lys Gly Lys Lys Asn Ile Phe Glu Ser Phe Val Asp Tyr Val
                355                 360                 365

Ala Val Glu Gln Leu Asp Gly Asp Asn Lys Tyr Asp Ala Gly Glu His
        370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
                420                 425                 430

Leu Asp Glu Phe Leu Gln Lys Thr Asp Pro Lys Asp Pro Ala Asn Tyr
                435                 440                 445

Ile Leu His Ala Val Leu Val His Ser Gly Asp Asn His Gly Gly His
450                 455                 460
```

```
Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Leu Ser Val Arg His Cys Thr Asn
            500                 505                 510

Ala Tyr Met Leu Val Tyr Ile Arg Glu Ser Lys Leu Ser Glu Val Leu
            515                 520                 525

Gln Ala Val Thr Asp His Asp Ile Pro Gln Gln Leu Val Glu Arg Leu
530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
            595                 600                 605

Leu Ser Gln Thr Met Gly Phe Pro Gln Asp Gln Ile Arg Leu Trp Pro
610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
            675                 680                 685

Leu Lys Met Tyr Asp Pro Lys Thr Arg Ser Leu Asn Tyr Cys Gly His
690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
            755                 760                 765

Gln Lys Asp Asp Pro Glu Asn Asp Asn Ser Glu Leu Pro Thr Ala Lys
770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830

Asp Pro Met Leu Leu Gln Phe Phe Lys Ser Gln Gly Tyr Arg Asp Gly
            835                 840                 845

Pro Gly Asn Pro Leu Arg His Asn Tyr Glu Gly Thr Leu Arg Asp Leu
            850                 855                 860

Leu Gln Phe Phe Lys Pro Arg Gln Pro Lys Lys Leu Tyr Tyr Gln Gln
865                 870                 875                 880
```

```
Leu Lys Met Lys Ile Thr Asp Phe Glu Asn Arg Arg Ser Phe Lys Cys
            885                 890                 895
Ile Trp Leu Asn Ser Gln Phe Arg Glu Glu Ile Thr Leu Tyr Pro
        900                 905                 910
Asp Lys His Gly Cys Val Arg Asp Leu Leu Glu Cys Lys Lys Ala
            915                 920                 925
Val Glu Leu Gly Glu Lys Ala Ser Gly Lys Leu Arg Leu Leu Glu Ile
    930                 935                 940
Val Ser Tyr Lys Ile Ile Gly Val His Gln Glu Asp Glu Leu Leu Glu
945                 950                 955                 960
Cys Leu Ser Pro Ala Thr Ser Arg Thr Phe Arg Ile Glu Glu Ile Pro
                965                 970                 975
Leu Asp Gln Val Asp Ile Asp Lys Glu Asn Glu Met Leu Val Thr Val
            980                 985                 990
Ala His Phe His Lys Glu Val Phe Gly Thr Phe Gly Ile Pro Phe Leu
        995                 1000                1005
Leu Arg Ile His Gln Gly Glu His Phe Arg Glu Val Met Lys Arg Ile
    1010                1015                1020
Gln Ser Leu Leu Asp Ile Gln Glu Lys Glu Phe Glu Lys Phe Lys Phe
1025                1030                1035                1040
Ala Ile Val Met Thr Gly Arg His Gln Tyr Ile Asn Glu Asp Glu Tyr
                1045                1050                1055
Glu Val Asn Leu Lys Asp Phe Glu Pro Gln Pro Gly Asn Met Ser His
            1060                1065                1070
Pro Arg Pro Trp Leu Gly Leu Asp His Phe Asn Lys Ala Pro Lys Arg
        1075                1080                1085
Ser Arg Tyr Thr Tyr Leu Glu Lys Ala Ile Lys Ile His Asn
    1090                1095                1100

<210> SEQ ID NO 3
<211> LENGTH: 1642
<212> TYPE: DNA
<213> ORGANISM: Homo sapiens
<220> FEATURE:
<221> NAME/KEY: CDS
<222> LOCATION: (158)..(1279)

<400> SEQUENCE: 3
gaatcggcgg tcccgcaggt cccggatgtt gcggacagta tgaggcaagc gcaggggac      60 ggggaccagc agctgtcgcc gccgctctca gggtgaagag ggaacagaaa tctttgcccc    120
ctgactttgg aaatctcgtt taaccttcaa actggcg atg tca agg gtt cca agt    175
                                        Met Ser Arg Val Pro Ser
                                          1               5 cct cca cct ccg gca gaa atg tcg agt ggc ccc gta gct gag agt tgg    223
Pro Pro Pro Pro Ala Glu Met Ser Ser Gly Pro Val Ala Glu Ser Trp
             10                  15                  20 tgc tac aca cag atc aag gta gtg aaa ttc tcc tac atg tgg acc atc    271
Cys Tyr Thr Gln Ile Lys Val Val Lys Phe Ser Tyr Met Trp Thr Ile
         25                  30                  35 aat aac ttt agc ttt tgc cgg gag gaa atg ggt gaa gtc att aaa agt    319
Asn Asn Phe Ser Phe Cys Arg Glu Glu Met Gly Glu Val Ile Lys Ser
     40                  45                  50 tct aca ttt tca tca gga gca aat gat aaa ctg aaa tgg tgt ttg cga    367
Ser Thr Phe Ser Ser Gly Ala Asn Asp Lys Leu Lys Trp Cys Leu Arg
 55                  60                  65                  70 gta aac ccc aaa ggg tta gat gaa gaa agc aaa gat tac ctg tca ctt    415
Val Asn Pro Lys Gly Leu Asp Glu Glu Ser Lys Asp Tyr Leu Ser Leu
```

```
                        75                   80                     85
tac ctg tta ctg gtc agc tgt cca aag agt gaa gtt cgg gca aaa ttc         463
Tyr Leu Leu Val Ser Cys Pro Lys Ser Glu Val Arg Ala Lys Phe
            90                    95                  100 aaa ttc tcc atc ctg aat gcc aag gga gaa gaa acc aaa gct atg gag         511
Lys Phe Ser Ile Leu Asn Ala Lys Gly Glu Glu Thr Lys Ala Met Glu
        105                   110                 115 agt caa cgg gca tat agg ttt gtg caa ggc aaa gac tgg gga ttc aag         559
Ser Gln Arg Ala Tyr Arg Phe Val Gln Gly Lys Asp Trp Gly Phe Lys
    120                   125                 130 aaa ttc atc cgt aga gat ttt ctt ttg gat gag gcc aac ggg ctt ctc         607
Lys Phe Ile Arg Arg Asp Phe Leu Leu Asp Glu Ala Asn Gly Leu Leu
135                   140                 145                 150 cct gat gac aag ctt acc ctc ttc tgc gag gtg agt gtt gtg caa gat         655
Pro Asp Asp Lys Leu Thr Leu Phe Cys Glu Val Ser Val Val Gln Asp
                155                   160                 165 tct gtc aac att tct ggc cag aat acc atg aac atg gta aag gtt cct         703
Ser Val Asn Ile Ser Gly Gln Asn Thr Met Asn Met Val Lys Val Pro
            170                   175                 180 gag tgc cgg ctg gca gat gag tta gga gga ctg tgg gag aat tcc cgg         751
Glu Cys Arg Leu Ala Asp Glu Leu Gly Gly Leu Trp Glu Asn Ser Arg
        185                   190                 195 ttc aca gac tgc tgc ttg tgt gtt gcc ggc cag gaa ttc cag gct cac         799
Phe Thr Asp Cys Cys Leu Cys Val Ala Gly Gln Glu Phe Gln Ala His
    200                   205                 210 aag gct atc tta gca gct cgt tct ccg gtt ttt agt gcc atg ttt gaa         847
Lys Ala Ile Leu Ala Ala Arg Ser Pro Val Phe Ser Ala Met Phe Glu
215                   220                 225                 230 cat gaa atg gag gag agc aaa aag aat cga gtt gaa atc aat gat gtg         895
His Glu Met Glu Glu Ser Lys Lys Asn Arg Val Glu Ile Asn Asp Val
                235                   240                 245 gag cct gaa gtt ttt aag gaa atg atg tgc ttc att tac acg ggg aag         943
Glu Pro Glu Val Phe Lys Glu Met Met Cys Phe Ile Tyr Thr Gly Lys
            250                   255                 260 gct cca aac ctc gac aaa atg gct gat gat ttg ctg gca gct gct gac         991
Ala Pro Asn Leu Asp Lys Met Ala Asp Asp Leu Leu Ala Ala Ala Asp
        265                   270                 275 aag tat gcc ctg gag cgc tta aag gtc atg tgt gag gat gcc ctc tgc        1039
Lys Tyr Ala Leu Glu Arg Leu Lys Val Met Cys Glu Asp Ala Leu Cys
    280                   285                 290 agt aac ctg tcc gtg gag aac gct gca gaa att ctc atc ctg gcc gac        1087
Ser Asn Leu Ser Val Glu Asn Ala Ala Glu Ile Leu Ile Leu Ala Asp
295                   300                 305                 310 ctc cac agt gca gat cag ttg aaa act cag gca gtg gat ttc atc aac        1135
Leu His Ser Ala Asp Gln Leu Lys Thr Gln Ala Val Asp Phe Ile Asn
                315                   320                 325 tat cat gct tcg gat gtc ttg gag acc tct ggg tgg aag tca atg gtg        1183
Tyr His Ala Ser Asp Val Leu Glu Thr Ser Gly Trp Lys Ser Met Val
            330                   335                 340 gtg tca cat ccc cac ttg gtg gct gag gca tac cgc tct ctg gct tca        1231
Val Ser His Pro His Leu Val Ala Glu Ala Tyr Arg Ser Leu Ala Ser
        345                   350                 355 gca cag tgc cct ttt ctg gga ccc cca cgc aaa cgc ctg aag caa tcc        1279
Ala Gln Cys Pro Phe Leu Gly Pro Pro Arg Lys Arg Leu Lys Gln Ser
    360                   365                 370 taagatcctg cttgttgtaa gactccgttt aatttccaga agcagcagcc actgttgctg     1339
ccactgacca ccaggtagac agcgcaatct gtggagcttt tactctgttg tgaggggaag     1399
agactgcatt gtggccccag acttttaaaa cagcactaaa taacttgggg gaaacggggg     1459
```

-continued

```
gagggaaaat gaaatgaaaa ccctgttgct gcgtcactgt gttcccttttg gcctgtctga    1519 gtttgatact gtggggattc agtttaggcg ctggcccgag gatatcccag cggtggtact    1579
tcggagacac ctgtctgcat ctgactgagc agaacaaatc gtcaggtgcc tggagcaaaa    1639
agg                                                                   1642
```

<210> SEQ ID NO 4
<211> LENGTH: 374
<212> TYPE: PRT
<213> ORGANISM: Homo sapiens

<400> SEQUENCE: 4

```
Met Ser Arg Val Pro Ser Pro Pro Ala Glu Met Ser Gly
  1               5                  10              15

Pro Val Ala Glu Ser Trp Cys Tyr Thr Gln Ile Lys Val Val Lys Phe
                 20                  25                  30

Ser Tyr Met Trp Thr Ile Asn Asn Phe Ser Phe Cys Arg Glu Glu Met
             35                  40                  45

Gly Glu Val Ile Lys Ser Ser Thr Phe Ser Ser Gly Ala Asn Asp Lys
 50                  55                  60

Leu Lys Trp Cys Leu Arg Val Asn Pro Lys Gly Leu Asp Glu Glu Ser
 65                  70                  75                  80

Lys Asp Tyr Leu Ser Leu Tyr Leu Leu Val Ser Cys Pro Lys Ser
                 85                  90                  95

Glu Val Arg Ala Lys Phe Lys Phe Ser Ile Leu Asn Ala Lys Gly Glu
                100                 105                 110

Glu Thr Lys Ala Met Glu Ser Gln Arg Ala Tyr Arg Phe Val Gln Gly
            115                 120                 125

Lys Asp Trp Gly Phe Lys Lys Phe Ile Arg Arg Asp Phe Leu Leu Asp
130                 135                 140

Glu Ala Asn Gly Leu Leu Pro Asp Asp Lys Leu Thr Leu Phe Cys Glu
145                 150                 155                 160

Val Ser Val Val Gln Asp Ser Val Asn Ile Ser Gly Gln Asn Thr Met
                165                 170                 175

Asn Met Val Lys Val Pro Glu Cys Arg Leu Ala Asp Glu Leu Gly Gly
            180                 185                 190

Leu Trp Glu Asn Ser Arg Phe Thr Asp Cys Cys Leu Cys Val Ala Gly
        195                 200                 205

Gln Glu Phe Gln Ala His Lys Ala Ile Leu Ala Ala Arg Ser Pro Val
210                 215                 220

Phe Ser Ala Met Phe Glu His Glu Met Glu Glu Ser Lys Lys Asn Arg
225                 230                 235                 240

Val Glu Ile Asn Asp Val Glu Pro Glu Val Phe Lys Glu Met Met Cys
                245                 250                 255

Phe Ile Tyr Thr Gly Lys Ala Pro Asn Leu Asp Lys Met Ala Asp Asp
            260                 265                 270

Leu Leu Ala Ala Ala Asp Lys Tyr Ala Leu Glu Arg Leu Lys Val Met
        275                 280                 285

Cys Glu Asp Ala Leu Cys Ser Asn Leu Ser Val Glu Asn Ala Ala Glu
290                 295                 300

Ile Leu Ile Leu Ala Asp Leu His Ser Ala Asp Gln Leu Lys Thr Gln
305                 310                 315                 320

Ala Val Asp Phe Ile Asn Tyr His Ala Ser Asp Val Leu Glu Thr Ser
                325                 330                 335
```

```
Gly Trp Lys Ser Met Val Val Ser His Pro His Leu Val Ala Glu Ala
        340                 345                 350

Tyr Arg Ser Leu Ala Ser Ala Gln Cys Pro Phe Leu Gly Pro Pro Arg
        355                 360                 365

Lys Arg Leu Lys Gln Ser
        370

<210> SEQ ID NO 5
<211> LENGTH: 4111
<212> TYPE: DNA
<213> ORGANISM: Homo sapiens
<220> FEATURE:
<221> NAME/KEY: CDS
<222> LOCATION: (1)..(2937)

<400> SEQUENCE: 5 gcg gag cct gcg ggt cgc cag cgg ccc cgc cga gag ccg gag gca atg         48
Ala Glu Pro Ala Gly Arg Gln Arg Pro Arg Arg Glu Pro Glu Ala Met
 1               5                  10                  15 gat gaa cag agc gtg gag agc att gct gag gtt ttc cga tgt ttc att         96
Asp Glu Gln Ser Val Glu Ser Ile Ala Glu Val Phe Arg Cys Phe Ile
                20                  25                  30 tgt atg gag aaa ttg cgg gat gca cgc ctg tgt cct cat tgc tcc aaa        144
Cys Met Glu Lys Leu Arg Asp Ala Arg Leu Cys Pro His Cys Ser Lys
            35                  40                  45 ctg tgt tgt ttc agc tgt att agg cgc tgg ctg aca gag cag aga gct        192
Leu Cys Cys Phe Ser Cys Ile Arg Arg Trp Leu Thr Glu Gln Arg Ala
        50                  55                  60 caa tgt cct cat tgc cgt gct cca ctc cag cta cga gaa cta gta aat        240
Gln Cys Pro His Cys Arg Ala Pro Leu Gln Leu Arg Glu Leu Val Asn
 65                  70                  75                  80 tgt cgt tgg gca gaa gaa gta aca caa cag ctt gat act ctt caa ctc        288
Cys Arg Trp Ala Glu Glu Val Thr Gln Gln Leu Asp Thr Leu Gln Leu
                85                  90                  95 tgc agt ctc acc aaa cat gaa gaa aat gaa aag gac aaa tgt gaa aat        336
Cys Ser Leu Thr Lys His Glu Glu Asn Glu Lys Asp Lys Cys Glu Asn
            100                 105                 110 cac cat gaa aaa ctt agt gta ttt tgc tgg act tgt aag aag tgt atc        384
His His Glu Lys Leu Ser Val Phe Cys Trp Thr Cys Lys Lys Cys Ile
        115                 120                 125 tgc cat cag tgt gca ctt tgg gga gga atg cat ggc gga cat acc ttt        432
Cys His Gln Cys Ala Leu Trp Gly Gly Met His Gly Gly His Thr Phe
    130                 135                 140 aaa cct ttg gca gaa att tat gag caa cac gtc act aaa gtg aat gaa        480
Lys Pro Leu Ala Glu Ile Tyr Glu Gln His Val Thr Lys Val Asn Glu
145                 150                 155                 160 gag gta gcc aaa ctt cgt cgg cgt ctc atg gaa ctg atc agc tta gtt        528
Glu Val Ala Lys Leu Arg Arg Arg Leu Met Glu Leu Ile Ser Leu Val
                165                 170                 175 caa gaa gtg gaa agg aat gta gaa gct gta aga aat gca aaa gat gag        576
Gln Glu Val Glu Arg Asn Val Glu Ala Val Arg Asn Ala Lys Asp Glu
            180                 185                 190 cgt gtt cgg gaa att agg aat gca gtg gag atg atg att gca cgg tta        624
Arg Val Arg Glu Ile Arg Asn Ala Val Glu Met Met Ile Ala Arg Leu
        195                 200                 205 gac aca cag ctg aag aat aag ctt ata aca ctg atg ggt cag aag aca        672
Asp Thr Gln Leu Lys Asn Lys Leu Ile Thr Leu Met Gly Gln Lys Thr
    210                 215                 220 tct cta acc caa gaa aca gag ctt ttg gaa tcc tta ctt cag gag gtg        720
Ser Leu Thr Gln Glu Thr Glu Leu Leu Glu Ser Leu Leu Gln Glu Val
```

|     |     |     |     |     |
| --- | --- | --- | --- | --- |
| 225 | 230 | 235 | 240 | |

```
gag cac cag ttg cgg tct tgt agt aag agt gag ttg ata tct aag agc      768
Glu His Gln Leu Arg Ser Cys Ser Lys Ser Glu Leu Ile Ser Lys Ser
                245                 250                 255 tca gag atc ctt atg atg ttt cag caa gtt cat cgg aag ccc atg gca      816
Ser Glu Ile Leu Met Met Phe Gln Gln Val His Arg Lys Pro Met Ala
                260                 265                 270 tct ttt gtt acc act cct gtt cca cca gac ttt acc agt gaa tta gtg      864
Ser Phe Val Thr Thr Pro Val Pro Pro Asp Phe Thr Ser Glu Leu Val
                275                 280                 285 cca tct tac gat tca gct act ttt gtt tta gag aat ttc agc act ttg      912
Pro Ser Tyr Asp Ser Ala Thr Phe Val Leu Glu Asn Phe Ser Thr Leu
            290                 295                 300 cgt cag aga gca gat cct gtt tac agt cca cct ctt caa gtt tca gga      960
Arg Gln Arg Ala Asp Pro Val Tyr Ser Pro Pro Leu Gln Val Ser Gly
305                 310                 315                 320 ctt tgc tgg agg tta aaa gtt tac cca gat gga aat gga gtt gtg cga     1008
Leu Cys Trp Arg Leu Lys Val Tyr Pro Asp Gly Asn Gly Val Val Arg
                325                 330                 335 ggt tac tac tta tct gtg ttt ctg gag ctc tca gct ggc ttg cct gaa     1056
Gly Tyr Tyr Leu Ser Val Phe Leu Glu Leu Ser Ala Gly Leu Pro Glu
                340                 345                 350 act tct aaa tat gaa tat cgt gta gag atg gtt cac cag tcc tgt aat     1104
Thr Ser Lys Tyr Glu Tyr Arg Val Glu Met Val His Gln Ser Cys Asn
                355                 360                 365 gat cct aca aaa aat atc att cga gaa ttt gca tct gac ttt gaa gtt     1152
Asp Pro Thr Lys Asn Ile Ile Arg Glu Phe Ala Ser Asp Phe Glu Val
            370                 375                 380 gga gaa tgc tgg ggc tat aat aga ttt ttc cgt ttg gac tta ctc gca     1200
Gly Glu Cys Trp Gly Tyr Asn Arg Phe Phe Arg Leu Asp Leu Leu Ala
385                 390                 395                 400 aat gaa gga tac ttg aat cca caa aat gat aca gtg att tta agg ttt     1248
Asn Glu Gly Tyr Leu Asn Pro Gln Asn Asp Thr Val Ile Leu Arg Phe
                405                 410                 415 cag gta cgt tca cca act ttc ttt caa aaa tcc cgg gac cag cat tgg     1296
Gln Val Arg Ser Pro Thr Phe Phe Gln Lys Ser Arg Asp Gln His Trp
            420                 425                 430 tac att act cag ttg gaa gct gca cag act agt tat atc caa caa ata     1344
Tyr Ile Thr Gln Leu Glu Ala Ala Gln Thr Ser Tyr Ile Gln Gln Ile
            435                 440                 445 aac aac ctt aaa gag aga ctt act att gag ctg tct cga act cag aag     1392
Asn Asn Leu Lys Glu Arg Leu Thr Ile Glu Leu Ser Arg Thr Gln Lys
            450                 455                 460 tca aga gat ttg tca cca cca gat aac cat ctt agc ccc caa aat gat     1440
Ser Arg Asp Leu Ser Pro Pro Asp Asn His Leu Ser Pro Gln Asn Asp
465                 470                 475                 480 gat gct ctg gag aca cga gct aag aag tct gca tgc tct gac atg ctt     1488
Asp Ala Leu Glu Thr Arg Ala Lys Lys Ser Ala Cys Ser Asp Met Leu
                485                 490                 495 ctc gaa ggt ggt cct act aca gct tct gta aga gag gcc aaa gag gat     1536
Leu Glu Gly Gly Pro Thr Thr Ala Ser Val Arg Glu Ala Lys Glu Asp
                500                 505                 510 gaa gaa gat gag gag aag att cag aat gaa gat tat cat cac gag ctt     1584
Glu Glu Asp Glu Glu Lys Ile Gln Asn Glu Asp Tyr His His Glu Leu
                515                 520                 525 tca gat gga gat ctg gat ctg gat ctt gtt tat gag gat gaa gta aat     1632
Ser Asp Gly Asp Leu Asp Leu Asp Leu Val Tyr Glu Asp Glu Val Asn
            530                 535                 540 cag ctc gat ggc agc agt tcc tct gct agt tcc aca gca aca agt aat     1680
```

| | | |
|---|---|---|
| Gln Leu Asp Gly Ser Ser Ser Ala Ser Ser Thr Ala Thr Ser Asn<br>545                          550                        555                        560 | | |
| aca gaa gaa aat gat att gat gaa gaa act atg tct gga gaa aat gat<br>Thr Glu Glu Asn Asp Ile Asp Glu Glu Thr Met Ser Gly Glu Asn Asp<br>                        565                        570                        575 | | 1728 |
| gtg gaa tat aac aac atg gaa tta gaa gag gga gaa ctc atg gaa gat<br>Val Glu Tyr Asn Asn Met Glu Leu Glu Glu Gly Glu Leu Met Glu Asp<br>                580                        585                        590 | | 1776 |
| gca gct gct gca gga ccc gca ggt agt agc cat ggt tat gtg ggt tcc<br>Ala Ala Ala Ala Gly Pro Ala Gly Ser Ser His Gly Tyr Val Gly Ser<br>            595                        600                        605 | | 1824 |
| agt agt aga ata tca aga aga aca cat tta tgc tcc gct gct acc agt<br>Ser Ser Arg Ile Ser Arg Arg Thr His Leu Cys Ser Ala Ala Thr Ser<br>610                          615                        620 | | 1872 |
| agt tta cta gac att gat cca tta att tta ata cat ttg ttg gac ctt<br>Ser Leu Leu Asp Ile Asp Pro Leu Ile Leu Ile His Leu Leu Asp Leu<br>625                          630                        635                        640 | | 1920 |
| aag gac cgg agc agt ata gaa aat ttg tgg ggc tta cag cct cgc cca<br>Lys Asp Arg Ser Ser Ile Glu Asn Leu Trp Gly Leu Gln Pro Arg Pro<br>                        645                        650                        655 | | 1968 |
| cct gct tca ctt ctg cag ccc aca gca tca tat tct cga aaa gat aaa<br>Pro Ala Ser Leu Leu Gln Pro Thr Ala Ser Tyr Ser Arg Lys Asp Lys<br>                660                        665                        670 | | 2016 |
| gac caa agg aag caa cag gca atg tgg cga gtg ccc tct gat tta aag<br>Asp Gln Arg Lys Gln Gln Ala Met Trp Arg Val Pro Ser Asp Leu Lys<br>            675                        680                        685 | | 2064 |
| atg cta aaa aga ctc aaa act caa atg gcc gaa gtt cga tgt atg aaa<br>Met Leu Lys Arg Leu Lys Thr Gln Met Ala Glu Val Arg Cys Met Lys<br>690                          695                        700 | | 2112 |
| act gat gta aag aat aca ctt tca gaa ata aaa agc agc agt gct gct<br>Thr Asp Val Lys Asn Thr Leu Ser Glu Ile Lys Ser Ser Ser Ala Ala<br>705                          710                        715                        720 | | 2160 |
| tct gga gac atg cag aca agc ctt ttt tct gct gac cag gca gct ctg<br>Ser Gly Asp Met Gln Thr Ser Leu Phe Ser Ala Asp Gln Ala Ala Leu<br>                        725                        730                        735 | | 2208 |
| gct gca tgt gga act gaa aac tct ggc aga ttg cag gat ttg gga atg<br>Ala Ala Cys Gly Thr Glu Asn Ser Gly Arg Leu Gln Asp Leu Gly Met<br>                740                        745                        750 | | 2256 |
| gaa ctc ctg gca aag tca tca gtt gcc aat tgt tac ata cga aac tcc<br>Glu Leu Leu Ala Lys Ser Ser Val Ala Asn Cys Tyr Ile Arg Asn Ser<br>            755                        760                        765 | | 2304 |
| aca aat aag aag agt aat tcg ccc aag cca gct cga tcc agt gta gca<br>Thr Asn Lys Lys Ser Asn Ser Pro Lys Pro Ala Arg Ser Ser Val Ala<br>770                          775                        780 | | 2352 |
| ggt agt cta tca ctt cga aga gca gtg gac cct gga gaa aat agt cgt<br>Gly Ser Leu Ser Leu Arg Arg Ala Val Asp Pro Gly Glu Asn Ser Arg<br>785                          790                        795                        800 | | 2400 |
| tca aag gga gac tgt cag act ctg tct gaa ggc tcc cca gga agc tct<br>Ser Lys Gly Asp Cys Gln Thr Leu Ser Glu Gly Ser Pro Gly Ser Ser<br>                        805                        810                        815 | | 2448 |
| cag tct ggg agc agg cac agt tct ccc cga gcc ttg ata cat ggc agt<br>Gln Ser Gly Ser Arg His Ser Ser Pro Arg Ala Leu Ile His Gly Ser<br>                820                        825                        830 | | 2496 |
| atc ggt gat att ctg cca aaa act gaa gac cgg cag tgt aaa gct ttg<br>Ile Gly Asp Ile Leu Pro Lys Thr Glu Asp Arg Gln Cys Lys Ala Leu<br>            835                        840                        845 | | 2544 |
| gat tca gat gct gtt gtg gtt gca gtt ttc agt ggc ttg cct gcg gtt<br>Asp Ser Asp Ala Val Val Val Ala Val Phe Ser Gly Leu Pro Ala Val<br>850                          855                        860 | | 2592 |

-continued

| | |
|---|---|
| gag aaa agg agg aaa atg gtc acc ttg ggg gct aat gct aaa gga ggt<br>Glu Lys Arg Arg Lys Met Val Thr Leu Gly Ala Asn Ala Lys Gly Gly<br>865                      870                      875                      880 | 2640 |
| cat ctg gaa gga ctg cag atg act gat ttg gaa aat aat tct gaa act<br>His Leu Glu Gly Leu Gln Met Thr Asp Leu Glu Asn Asn Ser Glu Thr<br>                     885                      890                      895 | 2688 |
| gga gag tta cag cct gta cta cct gaa gga gct tca gct gcc cct gaa<br>Gly Glu Leu Gln Pro Val Leu Pro Glu Gly Ala Ser Ala Ala Pro Glu<br>900                      905                      910 | 2736 |
| gaa gga atg agt agc gac agt gac att gaa tgt gac act gag aat gag<br>Glu Gly Met Ser Ser Asp Ser Asp Ile Glu Cys Asp Thr Glu Asn Glu<br>915                      920                      925 | 2784 |
| gag cag gaa gag cat acc agt gtg ggc ggg ttt cac gac tcc ttc atg<br>Glu Gln Glu Glu His Thr Ser Val Gly Gly Phe His Asp Ser Phe Met<br>930                      935                      940 | 2832 |
| gtc atg aca cag ccc ccg gat gaa gat aca cat tcc agt ttt cct gat<br>Val Met Thr Gln Pro Pro Asp Glu Asp Thr His Ser Ser Phe Pro Asp<br>945                      950                      955                      960 | 2880 |
| ggt gaa caa ata ggc cct gaa gat ctc agc ttc aat aca gat gaa aat<br>Gly Glu Gln Ile Gly Pro Glu Asp Leu Ser Phe Asn Thr Asp Glu Asn<br>        &nbsbsp;          965                      970                      975 | 2928 |
| agt gga agg taattgccaa atcaagagaa ctgacttgca agctaccttg<br>Ser Gly Arg | 2977 |
| accctgaatt ttgctgtagt tggtgctcaa atttgtcatc agtcagataa tcagatttgg | 3037 |
| tcttatttct tcattatctc gacctgaaat agtaatttgg aaactgttgg aaggtggcac | 3097 |
| agtttagtct aagacagcag tagtacatgg gaaaaacagt atgggaagag ttctttgtaa | 3157 |
| tgtaaggaaa taacaatgta gttctctatt aatttagcaa atttgtacat tcacaaaagg | 3217 |
| cagtttgtct actacagcag aaggctggtt aactgccaga aaatgtacct ccaggccctg | 3277 |
| catgccgtca gtaacccgcc cggcattggt gctctactgt ctttggctag agcttagttg | 3337 |
| tgtttaaata atcatcttta tatttggggt tttaattaca gttccattag tgcctgtaga | 3397 |
| ttagtgaaca gaaaattgct ttggaagaga ttctgccctg tagacactat gtgaataact | 3457 |
| gaagtaacac tagactgaat ctccttttg gagtatgtat cttctctcac ttgttcaagt | 3517 |
| acaggcacac tgttcaaccg catggtatct ttctgttgtg tgacttctac aaatgtaatt | 3577 |
| ttaaatgaaa ttaagttaac atggattcat tacgttcctg gccctgtaga cacgtgtaag | 3637 |
| attatttaaa attctttcat ttttttctgc ctcttactat acgactgtag tgcaacaaat | 3697 |
| attttaaagc ccccttttct tctttatttt cattagttgt acattgattt cagtgtcaac | 3757 |
| acatttaaag attcattcat gttgcacagt ggcttacatg aacgtgaaac tgtgatataa | 3817 |
| ggttttcttt catactcata attagcccaa aacagttgcc aaactttgcc attgtgctcc | 3877 |
| tgcatttgtg tttgagctgc tatatatttg tggaaattac actgaaagtt gactaagaga | 3937 |
| ctattgaaaa agcatgaata attaaatata catgtgagag acatctcatc tgctgtattt | 3997 |
| tacttagtga atattgttca ctcttccgtg tctgatgtct tgctgaatgc tgtgactcat | 4057 |
| agtttacttt tgttcaaaat agtttgcact ttttgttaat aaaatcaact tgag | 4111 |

<210> SEQ ID NO 6
<211> LENGTH: 979
<212> TYPE: PRT
<213> ORGANISM: Homo sapiens

<400> SEQUENCE: 6

Ala Glu Pro Ala Gly Arg Gln Arg Pro Arg Arg Glu Pro Glu Ala Met
1               5                     10                   15

-continued

```
Asp Glu Gln Ser Val Glu Ser Ile Ala Glu Val Phe Arg Cys Phe Ile
             20                  25                  30
Cys Met Glu Lys Leu Arg Asp Ala Arg Leu Cys Pro His Cys Ser Lys
             35                  40                  45
Leu Cys Cys Phe Ser Cys Ile Arg Arg Trp Leu Thr Glu Gln Arg Ala
 50                  55                  60
Gln Cys Pro His Cys Arg Ala Pro Leu Gln Leu Arg Glu Leu Val Asn
 65                  70                  75                  80
Cys Arg Trp Ala Glu Glu Val Thr Gln Gln Leu Asp Thr Leu Gln Leu
                 85                  90                  95
Cys Ser Leu Thr Lys His Glu Asn Glu Lys Asp Lys Cys Glu Asn
                 100                 105                 110
His His Glu Lys Leu Ser Val Phe Cys Trp Thr Cys Lys Lys Cys Ile
             115                 120                 125
Cys His Gln Cys Ala Leu Trp Gly Gly Met His Gly Gly His Thr Phe
 130                 135                 140
Lys Pro Leu Ala Glu Ile Tyr Glu Gln His Val Thr Lys Val Asn Glu
145                 150                 155                 160
Glu Val Ala Lys Leu Arg Arg Arg Leu Met Glu Leu Ile Ser Leu Val
                 165                 170                 175
Gln Glu Val Glu Arg Asn Val Glu Ala Val Arg Asn Ala Lys Asp Glu
             180                 185                 190
Arg Val Arg Glu Ile Arg Asn Ala Val Glu Met Met Ile Ala Arg Leu
             195                 200                 205
Asp Thr Gln Leu Lys Asn Lys Leu Ile Thr Leu Met Gly Gln Lys Thr
 210                 215                 220
Ser Leu Thr Gln Glu Thr Glu Leu Leu Glu Ser Leu Leu Gln Glu Val
225                 230                 235                 240
Glu His Gln Leu Arg Ser Cys Ser Lys Ser Glu Leu Ile Ser Lys Ser
                 245                 250                 255
Ser Glu Ile Leu Met Met Phe Gln Gln Val His Arg Lys Pro Met Ala
             260                 265                 270
Ser Phe Val Thr Thr Pro Val Pro Pro Asp Phe Thr Ser Glu Leu Val
             275                 280                 285
Pro Ser Tyr Asp Ser Ala Thr Phe Val Leu Glu Asn Phe Ser Thr Leu
             290                 295                 300
Arg Gln Arg Ala Asp Pro Val Tyr Ser Pro Pro Leu Gln Val Ser Gly
305                 310                 315                 320
Leu Cys Trp Arg Leu Lys Val Tyr Pro Asp Gly Asn Gly Val Val Arg
                 325                 330                 335
Gly Tyr Tyr Leu Ser Val Phe Leu Glu Leu Ser Ala Gly Leu Pro Glu
             340                 345                 350
Thr Ser Lys Tyr Glu Tyr Arg Val Glu Met Val His Gln Ser Cys Asn
             355                 360                 365
Asp Pro Thr Lys Asn Ile Ile Arg Glu Phe Ala Ser Asp Phe Glu Val
 370                 375                 380
Gly Glu Cys Trp Gly Tyr Asn Arg Phe Phe Arg Leu Asp Leu Leu Ala
385                 390                 395                 400
Asn Glu Gly Tyr Leu Asn Pro Gln Asn Asp Thr Val Ile Leu Arg Phe
                 405                 410                 415
Gln Val Arg Ser Pro Thr Phe Phe Gln Lys Ser Arg Asp Gln His Trp
             420                 425                 430
```

-continued

```
Tyr Ile Thr Gln Leu Glu Ala Ala Gln Thr Ser Tyr Ile Gln Gln Ile
            435                 440                 445

Asn Asn Leu Lys Glu Arg Leu Thr Ile Glu Leu Ser Arg Thr Gln Lys
        450                 455                 460

Ser Arg Asp Leu Ser Pro Pro Asp Asn His Leu Ser Pro Gln Asn Asp
465                 470                 475                 480

Asp Ala Leu Glu Thr Arg Ala Lys Lys Ser Ala Cys Ser Asp Met Leu
                485                 490                 495

Leu Glu Gly Gly Pro Thr Thr Ala Ser Val Arg Glu Ala Lys Glu Asp
            500                 505                 510

Glu Glu Asp Glu Glu Lys Ile Gln Asn Glu Asp Tyr His His Glu Leu
        515                 520                 525

Ser Asp Gly Asp Leu Asp Leu Asp Leu Val Tyr Glu Asp Glu Val Asn
    530                 535                 540

Gln Leu Asp Gly Ser Ser Ser Ala Ser Ser Thr Ala Thr Ser Asn
545                 550                 555                 560

Thr Glu Glu Asn Asp Ile Asp Glu Glu Thr Met Ser Gly Glu Asn Asp
                565                 570                 575

Val Glu Tyr Asn Asn Met Glu Leu Glu Glu Gly Glu Leu Met Glu Asp
            580                 585                 590

Ala Ala Ala Gly Pro Ala Gly Ser Ser His Gly Tyr Val Gly Ser
        595                 600                 605

Ser Ser Arg Ile Ser Arg Arg Thr His Leu Cys Ser Ala Ala Thr Ser
    610                 615                 620

Ser Leu Leu Asp Ile Asp Pro Leu Ile Leu Ile His Leu Leu Asp Leu
625                 630                 635                 640

Lys Asp Arg Ser Ser Ile Glu Asn Leu Trp Gly Leu Gln Pro Arg Pro
                645                 650                 655

Pro Ala Ser Leu Leu Gln Pro Thr Ala Ser Tyr Ser Arg Lys Asp Lys
            660                 665                 670

Asp Gln Arg Lys Gln Gln Ala Met Trp Arg Val Pro Ser Asp Leu Lys
        675                 680                 685

Met Leu Lys Arg Leu Lys Thr Gln Met Ala Glu Val Arg Cys Met Lys
    690                 695                 700

Thr Asp Val Lys Asn Thr Leu Ser Glu Ile Lys Ser Ser Ser Ala Ala
705                 710                 715                 720

Ser Gly Asp Met Gln Thr Ser Leu Phe Ser Ala Asp Gln Ala Ala Leu
                725                 730                 735

Ala Ala Cys Gly Thr Glu Asn Ser Gly Arg Leu Gln Asp Leu Gly Met
            740                 745                 750

Glu Leu Leu Ala Lys Ser Ser Val Ala Asn Cys Tyr Ile Arg Asn Ser
        755                 760                 765

Thr Asn Lys Lys Ser Asn Ser Pro Lys Pro Ala Arg Ser Ser Val Ala
    770                 775                 780

Gly Ser Leu Ser Leu Arg Arg Ala Val Asp Pro Gly Glu Asn Ser Arg
785                 790                 795                 800

Ser Lys Gly Asp Cys Gln Thr Leu Ser Glu Gly Ser Pro Gly Ser Ser
                805                 810                 815

Gln Ser Gly Ser Arg His Ser Ser Pro Arg Ala Leu Ile His Gly Ser
            820                 825                 830

Ile Gly Asp Ile Leu Pro Lys Thr Glu Asp Arg Gln Cys Lys Ala Leu
        835                 840                 845

Asp Ser Asp Ala Val Val Val Ala Val Phe Ser Gly Leu Pro Ala Val
```

|                     |                     |                     |
|---------------------|---------------------|---------------------|
|         850         |         855         |         860         |

Glu Lys Arg Arg Lys Met Val Thr Leu Gly Ala Asn Ala Lys Gly Gly
865                 870                 875                 880

His Leu Glu Gly Leu Gln Met Thr Asp Leu Glu Asn Asn Ser Glu Thr
                885                 890                 895

Gly Glu Leu Gln Pro Val Leu Pro Glu Gly Ala Ser Ala Ala Pro Glu
            900                 905                 910

Glu Gly Met Ser Ser Asp Ser Asp Ile Glu Cys Asp Thr Glu Asn Glu
                915                 920                 925

Glu Gln Glu Glu His Thr Ser Val Gly Gly Phe His Asp Ser Phe Met
    930                 935                 940

Val Met Thr Gln Pro Pro Asp Glu Asp Thr His Ser Ser Phe Pro Asp
945                 950                 955                 960

Gly Glu Gln Ile Gly Pro Glu Asp Leu Ser Phe Asn Thr Asp Glu Asn
                965                 970                 975

Ser Gly Arg

<210> SEQ ID NO 7
<211> LENGTH: 639
<212> TYPE: DNA
<213> ORGANISM: Homo sapiens
<220> FEATURE:
<221> NAME/KEY: CDS
<222> LOCATION: (1)..(639)

<400> SEQUENCE: 7

```
atg aac cac cag cag cag cag cag cag aaa gcg ggc gag cag cag       48
Met Asn His Gln Gln Gln Gln Gln Gln Lys Ala Gly Glu Gln Gln
 1               5                  10                  15 ttg agc gag ccc gag gac atg gag atg gaa gcg gga gat aca gat gac   96
Leu Ser Glu Pro Glu Asp Met Glu Met Glu Ala Gly Asp Thr Asp Asp
             20                  25                  30 cca cca aga att act cag aac cct gtg atc aat ggg aat gtg gcc ctg  144
Pro Pro Arg Ile Thr Gln Asn Pro Val Ile Asn Gly Asn Val Ala Leu
         35                  40                  45 agt gat gga cac aac acc gcg gag gag gac atg gag gat gac acc agt  192
Ser Asp Gly His Asn Thr Ala Glu Glu Asp Met Glu Asp Asp Thr Ser
     50                  55                  60 tgg cgc tcc gag gca acc ttt cag ttc act gtg gag cgc ttc agc aga  240
Trp Arg Ser Glu Ala Thr Phe Gln Phe Thr Val Glu Arg Phe Ser Arg
 65                  70                  75                  80 ctg agt gag tcg gtc ctt agc cct ccg tgt ttt gtg cga aat ctg cca  288
Leu Ser Glu Ser Val Leu Ser Pro Pro Cys Phe Val Arg Asn Leu Pro
                 85                  90                  95 tgg aag att atg gtg atg cca cgc ttt tat cca gac aga cca cac caa  336
Trp Lys Ile Met Val Met Pro Arg Phe Tyr Pro Asp Arg Pro His Gln
            100                 105                 110 aaa agc gta gga ttc ttt ctc cag tgc aat gct gaa tct gat tcc acg  384
Lys Ser Val Gly Phe Phe Leu Gln Cys Asn Ala Glu Ser Asp Ser Thr
        115                 120                 125 tca tgg tct tgc cat gca caa gca gtg ctg aag ata ata aat tac aga  432
Ser Trp Ser Cys His Ala Gln Ala Val Leu Lys Ile Ile Asn Tyr Arg
    130                 135                 140 gat gat gaa aag tcg ttc agt cgt cgt att agt cat ttg ttc ttc cat  480
Asp Asp Glu Lys Ser Phe Ser Arg Arg Ile Ser His Leu Phe Phe His
145                 150                 155                 160 aaa gaa aat gat tgg gga ttt tcc aat ttt atg gcc tgg agt gaa gtg  528
Lys Glu Asn Asp Trp Gly Phe Ser Asn Phe Met Ala Trp Ser Glu Val
                165                 170                 175
```

```
acc gat cct gag aaa gga ttt ata gat gat gac aaa gtt acc ttt gaa    576
Thr Asp Pro Glu Lys Gly Phe Ile Asp Asp Asp Lys Val Thr Phe Glu
        180                 185                 190 gtc ttt gta cag gcg gat gct ccc cat gga gtt gcg tgg gat tca aag    624
Val Phe Val Gln Ala Asp Ala Pro His Gly Val Ala Trp Asp Ser Lys
            195                 200                 205 aag cac aca ggc tac                                                639
Lys His Thr Gly Tyr
        210

<210> SEQ ID NO 8
<211> LENGTH: 213
<212> TYPE: PRT
<213> ORGANISM: Homo sapiens

<400> SEQUENCE: 8

Met Asn His Gln Gln Gln Gln Gln Gln Lys Ala Gly Glu Gln Gln
 1               5                  10                  15

Leu Ser Glu Pro Glu Asp Met Glu Met Glu Ala Gly Asp Thr Asp Asp
            20                  25                  30

Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
 50                  55                  60

Trp Arg Ser Glu Ala Thr Phe Gln Phe Thr Val Glu Arg Phe Ser Arg
 65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr
        210

<210> SEQ ID NO 9
<211> LENGTH: 540
<212> TYPE: DNA
<213> ORGANISM: Homo sapiens
<220> FEATURE:
<221> NAME/KEY: CDS
<222> LOCATION: (1)..(540)

<400> SEQUENCE: 9 atg tca agg gtt cca agt cct cca cct ccg gca gaa atg tcg agt ggc     48
Met Ser Arg Val Pro Ser Pro Pro Pro Ala Glu Met Ser Ser Gly
 1               5                  10                  15 ccc gta gct gag agt tgg tgc tac aca cag atc aag gta gtg aaa ttc     96
Pro Val Ala Glu Ser Trp Cys Tyr Thr Gln Ile Lys Val Val Lys Phe
```

```
                Pro Val Ala Glu Ser Trp Cys Tyr Thr Gln Ile Lys Val Val Lys Phe
                             20                  25                  30 tcc tac atg tgg acc atc aat aac ttt agc ttt tgc cgg gag gaa atg        144
Ser Tyr Met Trp Thr Ile Asn Asn Phe Ser Phe Cys Arg Glu Glu Met
         35                  40                  45 ggt gaa gtc att aaa agt tct aca ttt tca tca gga gca aat gat aaa        192
Gly Glu Val Ile Lys Ser Ser Thr Phe Ser Ser Gly Ala Asn Asp Lys
 50                  55                  60 ctg aaa tgg tgt ttg cga gta aac ccc aaa ggg tta gat gaa gaa agc        240
Leu Lys Trp Cys Leu Arg Val Asn Pro Lys Gly Leu Asp Glu Glu Ser
 65                  70                  75                  80 aaa gat tac ctg tca ctt tac ctg tta ctg gtc agc tgt cca aag agt        288
Lys Asp Tyr Leu Ser Leu Tyr Leu Leu Leu Val Ser Cys Pro Lys Ser
                 85                  90                  95 gaa gtt cgg gca aaa ttc aaa ttc tcc atc ctg aat gcc aag gga gaa        336
Glu Val Arg Ala Lys Phe Lys Phe Ser Ile Leu Asn Ala Lys Gly Glu
            100                 105                 110 gaa acc aaa gct atg gag agt caa cgg gca tat agg ttt gtg caa ggc        384
Glu Thr Lys Ala Met Glu Ser Gln Arg Ala Tyr Arg Phe Val Gln Gly
        115                 120                 125 aaa gac tgg gga ttc aag aaa ttc atc cgt aga gat ttt ctt ttg gat        432
Lys Asp Trp Gly Phe Lys Lys Phe Ile Arg Arg Asp Phe Leu Leu Asp
130                 135                 140 gag gcc aac ggg ctt ctc cct gat gac aag ctt acc ctc ttc tgc gag        480
Glu Ala Asn Gly Leu Leu Pro Asp Asp Lys Leu Thr Leu Phe Cys Glu
145                 150                 155                 160 gtg agt gtt gtg caa gat tct gtc aac att tct ggc cag aat acc atg        528
Val Ser Val Val Gln Asp Ser Val Asn Ile Ser Gly Gln Asn Thr Met
                165                 170                 175 aac atg gta aag                                                         540
Asn Met Val Lys
            180

<210> SEQ ID NO 10
<211> LENGTH: 180
<212> TYPE: PRT
<213> ORGANISM: Homo sapiens

<400> SEQUENCE: 10

Met Ser Arg Val Pro Ser Pro Pro Pro Ala Glu Met Ser Ser Gly
 1               5                  10                  15

Pro Val Ala Glu Ser Trp Cys Tyr Thr Gln Ile Lys Val Val Lys Phe
             20                  25                  30

Ser Tyr Met Trp Thr Ile Asn Asn Phe Ser Phe Cys Arg Glu Glu Met
         35                  40                  45

Gly Glu Val Ile Lys Ser Ser Thr Phe Ser Ser Gly Ala Asn Asp Lys
 50                  55                  60

Leu Lys Trp Cys Leu Arg Val Asn Pro Lys Gly Leu Asp Glu Glu Ser
 65                  70                  75                  80

Lys Asp Tyr Leu Ser Leu Tyr Leu Leu Leu Val Ser Cys Pro Lys Ser
                 85                  90                  95

Glu Val Arg Ala Lys Phe Lys Phe Ser Ile Leu Asn Ala Lys Gly Glu
            100                 105                 110

Glu Thr Lys Ala Met Glu Ser Gln Arg Ala Tyr Arg Phe Val Gln Gly
        115                 120                 125

Lys Asp Trp Gly Phe Lys Lys Phe Ile Arg Arg Asp Phe Leu Leu Asp
130                 135                 140

Glu Ala Asn Gly Leu Leu Pro Asp Asp Lys Leu Thr Leu Phe Cys Glu
```

```
                    145                 150                 155                 160
                Val Ser Val Val Gln Asp Ser Val Asn Ile Ser Gly Gln Asn Thr Met
                                165                 170                 175

Asn Met Val Lys
                            180

<210> SEQ ID NO 11
<211> LENGTH: 459
<212> TYPE: DNA
<213> ORGANISM: Homo sapiens
<220> FEATURE:
<221> NAME/KEY: CDS
<222> LOCATION: (1)..(459)

<400> SEQUENCE: 11 ttt acc agt gaa tta gtg cca tct tac gat tca gct act ttt gtt tta        48
Phe Thr Ser Glu Leu Val Pro Ser Tyr Asp Ser Ala Thr Phe Val Leu
  1               5                  10                  15 gag aat ttc agc act ttg cgt cag aga gca gat cct gtt tac agt cca        96
Glu Asn Phe Ser Thr Leu Arg Gln Arg Ala Asp Pro Val Tyr Ser Pro
                 20                  25                  30 cct ctt caa gtt tca gga ctt tgc tgg agg tta aaa gtt tac cca gat       144
Pro Leu Gln Val Ser Gly Leu Cys Trp Arg Leu Lys Val Tyr Pro Asp
             35                  40                  45 gga aat gga gtt gtg cga ggt tac tac tta tct gtg ttt ctg gag ctc       192
Gly Asn Gly Val Val Arg Gly Tyr Tyr Leu Ser Val Phe Leu Glu Leu
         50                  55                  60 tca gct ggc ttg cct gaa act tct aaa tat gaa tat cgt gta gag atg       240
Ser Ala Gly Leu Pro Glu Thr Ser Lys Tyr Glu Tyr Arg Val Glu Met
 65                  70                  75                  80 gtt cac cag tcc tgt aat gat cct aca aaa aat atc att cga gaa ttt       288
Val His Gln Ser Cys Asn Asp Pro Thr Lys Asn Ile Ile Arg Glu Phe
                 85                  90                  95 gca tct gac ttt gaa gtt gga gaa tgc tgg ggc tat aat aga ttt ttc       336
Ala Ser Asp Phe Glu Val Gly Glu Cys Trp Gly Tyr Asn Arg Phe Phe
            100                 105                 110 cgt ttg gac tta ctc gca aat gaa gga tac ttg aat cca caa aat gat       384
Arg Leu Asp Leu Leu Ala Asn Glu Gly Tyr Leu Asn Pro Gln Asn Asp
        115                 120                 125 aca gtg att tta agg ttt cag gta cgt tca cca act ttc ttt caa aaa       432
Thr Val Ile Leu Arg Phe Gln Val Arg Ser Pro Thr Phe Phe Gln Lys
    130                 135                 140 tcc cgg gac cag cat tgg tac att act                                   459
Ser Arg Asp Gln His Trp Tyr Ile Thr
145                 150

<210> SEQ ID NO 12
<211> LENGTH: 153
<212> TYPE: PRT
<213> ORGANISM: Homo sapiens

<400> SEQUENCE: 12

Phe Thr Ser Glu Leu Val Pro Ser Tyr Asp Ser Ala Thr Phe Val Leu
  1               5                  10                  15

Glu Asn Phe Ser Thr Leu Arg Gln Arg Ala Asp Pro Val Tyr Ser Pro
                 20                  25                  30

Pro Leu Gln Val Ser Gly Leu Cys Trp Arg Leu Lys Val Tyr Pro Asp
             35                  40                  45

Gly Asn Gly Val Val Arg Gly Tyr Tyr Leu Ser Val Phe Leu Glu Leu
         50                  55                  60
```

```
Ser Ala Gly Leu Pro Glu Thr Ser Lys Tyr Glu Tyr Arg Val Glu Met
 65                  70                  75                  80

Val His Gln Ser Cys Asn Asp Pro Thr Lys Asn Ile Ile Arg Glu Phe
                 85                  90                  95

Ala Ser Asp Phe Glu Val Gly Glu Cys Trp Gly Tyr Asn Arg Phe Phe
            100                 105                 110

Arg Leu Asp Leu Leu Ala Asn Glu Gly Tyr Leu Asn Pro Gln Asn Asp
        115                 120                 125

Thr Val Ile Leu Arg Phe Gln Val Arg Ser Pro Thr Phe Phe Gln Lys
    130                 135                 140

Ser Arg Asp Gln His Trp Tyr Ile Thr
145                 150
```

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 13
gcgaattcca ggccgcg                                                17

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
ttcctcgagc cgacttagcc tgtgtgc                                     27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
cttcgaattc gcgatgtcaa gggttcc                                     27

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 16
ccatgctcga ggtattctag ccagaaatg                                   29

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
ccagaattca ccagtgaatt agtgcc                                      26

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
ccactcgagt aatgtaccaa tgctagtcc                                  29

<210> SEQ ID NO 19
<211> LENGTH: 94
<212> TYPE: PRT
<213> ORGANISM: Artificial Sequence
<220> FEATURE:
<223> OTHER INFORMATION: Description of Artificial Sequence: Consensus
      Sequence
<221> NAME/KEY: SITE
<222> LOCATION: (2)..(22)
<223> OTHER INFORMATION: Xaa = any amino acid
<221> NAME/KEY: UNSURE
<222> LOCATION: (19)..(22)
<223> OTHER INFORMATION: Xaa may or may not be present
<221> NAME/KEY: SITE
<222> LOCATION: (24)
<223> OTHER INFORMATION: Xaa=any amino acid
<221> NAME/KEY: SITE
<222> LOCATION: (26)..(28)
<223> OTHER INFORMATION: Xaa=any amino acid
<221> NAME/KEY: SITE
<222> LOCATION: (30)
<223> OTHER INFORMATION: Xaa=any amino acid
<221> NAME/KEY: SITE
<222> LOCATION: (32)..(47)
<223> OTHER INFORMATION: Xaa=any amino acid
<221> NAME/KEY: UNSURE
<222> LOCATION: (47)
<223> OTHER INFORMATION: Xaa may or may not be present
<221> NAME/KEY: SITE
<222> LOCATION: (49)..(76)
<223> OTHER INFORMATION: Xaa=any amino acid
<221> NAME/KEY: UNSURE
<222> LOCATION: (73)..(76)
<223> OTHER INFORMATION: Xaa may or may not be present
<221> NAME/KEY: SITE
<222> LOCATION: (78)..(93)
<223> OTHER INFORMATION: Xaa=any amino acid
<221> NAME/KEY: UNSURE
<222> LOCATION: (93)
<223> OTHER INFORMATION: Xaa may or may not be present

<400> SEQUENCE: 19

Glu Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Leu Xaa Trp Xaa Xaa Xaa Val Xaa Pro Xaa
             20                  25                  30

Xaa Xaa Xaa Xaa Xaa Xaa Xaa Xaa Xaa Xaa Xaa Xaa Xaa Xaa Xaa Leu
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Lys Xaa Xaa Xaa
 65                  70                  75                  80

Xaa Xaa Xaa Xaa Xaa Xaa Xaa Xaa Xaa Xaa Xaa Xaa Xaa Trp
                 85                  90

<210> SEQ ID NO 20
<211> LENGTH: 9
<212> TYPE: PRT
<213> ORGANISM: Artificial Sequence
<220> FEATURE:

```
<221> NAME/KEY: SITE
<222> LOCATION: (2)
<223> OTHER INFORMATION: Xaa =any amino acid
<221> NAME/KEY: SITE
<222> LOCATION: (4)
<223> OTHER INFORMATION: Xaa=any amino acid
<221> NAME/KEY: SITE
<222> LOCATION: (5)
<223> OTHER INFORMATION: Xaa =Leu or Ile
<221> NAME/KEY: SITE
<222> LOCATION: (6)
<223> OTHER INFORMATION: Xaa =any amino acid
<221> NAME/KEY: SITE
<222> LOCATION: (8)
<223> OTHER INFORMATION: Xaa = any amino acid
<223> OTHER INFORMATION: Description of Artificial Sequence: Consensus
      Sequence

<400> SEQUENCE: 20

Leu Xaa Trp Xaa Xaa Xaa Val Xaa Pro
  1               5

<210> SEQ ID NO 21
<211> LENGTH: 124
<212> TYPE: PRT
<213> ORGANISM: Artificial Sequence
<220> FEATURE:
<221> NAME/KEY: SITE
<222> LOCATION: (2)..(14)
<223> OTHER INFORMATION: Xaa=any amino acid
<221> NAME/KEY: UNSURE
<222> LOCATION: (12)..(14)
<223> OTHER INFORMATION: Xaa may or may not be present
<221> NAME/KEY: SITE
<222> LOCATION: (16)..(22)
<223> OTHER INFORMATION: Xaa=any amino acid
<221> NAME/KEY: SITE
<222> LOCATION: (26)..(28)
<223> OTHER INFORMATION: Xaa=any amino acid
<221> NAME/KEY: SITE
<222> LOCATION: (32)..(42)
<223> OTHER INFORMATION: Xaa = any amino acid
<221> NAME/KEY: UNSURE
<222> LOCATION: (42)
<223> OTHER INFORMATION: Xaa may or may not be present
<221> NAME/KEY: SITE
<222> LOCATION: (44)..(47)
<223> OTHER INFORMATION: Xaa  = any  amino acid
<221> NAME/KEY: UNSURE
<222> LOCATION: (73)..(76)
<223> OTHER INFORMATION: Xaa may or may not be present
<221> NAME/KEY: SITE
<222> LOCATION: (78)..(87)
<223> OTHER INFORMATION: Xaa = any amino acid
<221> NAME/KEY: UNSURE
<222> LOCATION: (87)
<223> OTHER INFORMATION: Xaa may or may not be present
<221> NAME/KEY: SITE
<222> LOCATION: (89)..(93)
<223> OTHER INFORMATION: Xaa=any amino acid
<221> NAME/KEY: SITE
<222> LOCATION: (96)..(98)
<223> OTHER INFORMATION: Xaa=any amino acid
<221> NAME/KEY: SITE
<222> LOCATION: (100)..(115)
<223> OTHER INFORMATION: Xaa=any amino acid
<221> NAME/KEY: SITE
<222> LOCATION: (117)..(123)
<223> OTHER INFORMATION: Xaa=any amino acid
<221> NAME/KEY: UNSURE
<222> LOCATION: (122)..(123)
<223> OTHER INFORMATION: Xaa may or may not be present
<223> OTHER INFORMATION: Description of Artificial Sequence: Consensus
      Sequence
<221> NAME/KEY: UNSURE
<222> LOCATION: (22)
<223> OTHER INFORMATION: Xaa may or may not be present
```

```
<221> NAME/KEY: SITE
<222> LOCATION: (24)
<223> OTHER INFORMATION: Xaa=any amino acid
<221> NAME/KEY: SITE
<222> LOCATION: (30)
<223> OTHER INFORMATION: Xaa=any amino acid
<221> NAME/KEY: SITE
<222> LOCATION: (49)..(76)
<223> OTHER INFORMATION: Xaa = any amino acid

<400> SEQUENCE: 21

Glu Xaa Xaa Xaa Xaa Xaa Xaa Xaa Xaa Xaa Xaa Xaa Xaa Xaa Ser Xaa
 1               5                  10                  15

Xaa Xaa Xaa Xaa Xaa Xaa Leu Xaa Trp Xaa Xaa Xaa Val Xaa Pro Xaa
            20                  25                  30

Xaa Xaa Xaa Xaa Xaa Xaa Xaa Xaa Xaa Ser Xaa Xaa Xaa Xaa Xaa Leu
        35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Lys Xaa Xaa Xaa
65                  70                  75                  80

Xaa Xaa Xaa Xaa Xaa Xaa Xaa Phe Xaa Xaa Xaa Xaa Xaa Trp Gly Xaa
                85                  90                  95

Xaa Xaa Phe Xaa Xaa Xaa Xaa Xaa Xaa Xaa Xaa Xaa Xaa Xaa Xaa Xaa
            100                 105                 110

Xaa Xaa Xaa Asp Xaa Xaa Xaa Xaa Xaa Xaa Xaa Val
        115                 120

<210> SEQ ID NO 22
<211> LENGTH: 124
<212> TYPE: PRT
<213> ORGANISM: Artificial Sequence
<220> FEATURE:
<221> NAME/KEY: SITE
<222> LOCATION: (2)..(5)
<223> OTHER INFORMATION: Xaa =any amino acid
<221> NAME/KEY: SITE
<222> LOCATION: (6)
<223> OTHER INFORMATION: Xaa =  Val, Leu, or Ile
<221> NAME/KEY: SITE
<222> LOCATION: (7)..(14)
<223> OTHER INFORMATION: Xaa =any amino acid
<221> NAME/KEY: SITE
<222> LOCATION: (16)
<223> OTHER INFORMATION: Xaa=any amino acid
<221> NAME/KEY: SITE
<222> LOCATION: (17)
<223> OTHER INFORMATION: Xaa = Pro or Gly
<221> NAME/KEY: SITE
<222> LOCATION: (18)..(22)
<223> OTHER INFORMATION: Xaa =any amino acid
<221> NAME/KEY: UNSURE
<222> LOCATION: (22)..(22)
<223> OTHER INFORMATION: Xaa may or may not be present
<221> NAME/KEY: SITE
<222> LOCATION: (24)
<223> OTHER INFORMATION: Xaa =any amino acid
<221> NAME/KEY: SITE
<222> LOCATION: (26)
<223> OTHER INFORMATION: Xaa =any amino acid
<221> NAME/KEY: SITE
<222> LOCATION: (27)
<223> OTHER INFORMATION: Xaa =Val, Leu or Ile
<221> NAME/KEY: SITE
<222> LOCATION: (28)
<223> OTHER INFORMATION: Xaa = any amino acid
<221> NAME/KEY: SITE
<222> LOCATION: (30)
<223> OTHER INFORMATION: Xaa = any amino acid
<221> NAME/KEY: SITE
```

```
<222> LOCATION: (32)..(42)
<223> OTHER INFORMATION: Xaa = any amino acid
<221> NAME/KEY: UNSURE
<222> LOCATION: (42)..(42)
<223> OTHER INFORMATION: Xaa may or may not be present
<221> NAME/KEY: SITE
<222> LOCATION: (44)
<223> OTHER INFORMATION: Xaa =Val, Leu or Ile
<221> NAME/KEY: SITE
<222> LOCATION: (45)..(47)
<223> OTHER INFORMATION: Xaa=any amino acid
<221> NAME/KEY: SITE
<222> LOCATION: (49)..(66)
<223> OTHER INFORMATION: Xaa=any amino acid
<221> NAME/KEY: UNSURE
<222> LOCATION: (65)..(66)
<223> OTHER INFORMATION: Xaa may or may not be present
<221> NAME/KEY: SITE
<222> LOCATION: (67)
<223> OTHER INFORMATION: Xaa=Val, Leu or Ile
<221> NAME/KEY: SITE
<222> LOCATION: (68)..(73)
<223> OTHER INFORMATION: Xaa = any amino acid
<221> NAME/KEY: SITE
<222> LOCATION: (74)
<223> OTHER INFORMATION: Xaa=Asp, Glu, Asn or Gln
<221> NAME/KEY: SITE
<222> LOCATION: (75)..(76)
<223> OTHER INFORMATION: Xaa = any amino acid
<223> OTHER INFORMATION: Description of Artificial Sequence: Consensus
      Sequence
<221> NAME/KEY: UNSURE
<222> LOCATION: (13)..(14)
<223> OTHER INFORMATION: Xaa may or may not be present
<221> NAME/KEY: UNSURE
<222> LOCATION: (72)..(73)
<223> OTHER INFORMATION: Xaa may or may not be present
<221> NAME/KEY: SITE
<222> LOCATION: (78)..(87)
<223> OTHER INFORMATION: Xaa = any amino acid
<221> NAME/KEY: UNSURE
<222> LOCATION: (87)
<223> OTHER INFORMATION: Xaa may or may not be present
<221> NAME/KEY: SITE
<222> LOCATION: (89)..(93)
<223> OTHER INFORMATION: Xaa=any amino acid
<221> NAME/KEY: SITE
<222> LOCATION: (96)
<223> OTHER INFORMATION: Xaa=Trp or Phe
<221> NAME/KEY: SITE
<222> LOCATION: (97)..(98)
<223> OTHER INFORMATION: Xaa=any amino acid
<221> NAME/KEY: SITE
<222> LOCATION: (100)..(104)
<223> OTHER INFORMATION: Xaa = any amino acid
<221> NAME/KEY: SITE
<222> LOCATION: (105)
<223> OTHER INFORMATION: Xaa=Val, Leu or Ile
<221> NAME/KEY: SITE
<222> LOCATION: (106)
<223> OTHER INFORMATION: Xaa=any amino acid
<221> NAME/KEY: SITE
<222> LOCATION: (107)
<223> OTHER INFORMATION: Xaa=Asp, Glu, Asn or Gln
<221> NAME/KEY: SITE
<222> LOCATION: (108)..(114)
<223> OTHER INFORMATION: Xaa=any amino acid
<221> NAME/KEY: SITE
<222> LOCATION: (115)
<223> OTHER INFORMATION: Xaa=Asp, Glu, Asn or Gln
<221> NAME/KEY: SITE
<222> LOCATION: (117)
<223> OTHER INFORMATION: Xaa=any amino acid
<221> NAME/KEY: SITE
<222> LOCATION: (118)
<223> OTHER INFORMATION: Xaa=Val, Leu or Ile
<221> NAME/KEY: SITE
<222> LOCATION: (119)..(122)
<223> OTHER INFORMATION: Xaa=any amino acid
```

```
<221> NAME/KEY: UNSURE
<222> LOCATION: (121)..(122)
<223> OTHER INFORMATION: Xaa may or may not be present
<221> NAME/KEY: SITE
<222> LOCATION: (123)
<223> OTHER INFORMATION: Xaa=Asp, Glu, Asn or Gln

<400> SEQUENCE: 22

Glu Xaa Xaa Xaa Xaa Xaa Xaa Xaa Xaa Xaa Xaa Xaa Xaa Ser Xaa
 1               5                   10                  15

Xaa Xaa Xaa Xaa Xaa Xaa Leu Xaa Trp Xaa Xaa Xaa Val Xaa Pro Xaa
                20                  25                  30

Xaa Xaa Xaa Xaa Xaa Xaa Xaa Xaa Xaa Ser Xaa Xaa Xaa Xaa Leu
            35                  40                  45

Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Lys Xaa Xaa Xaa
    65                  70                  75              80

Xaa Xaa Xaa Xaa Xaa Xaa Xaa Phe Xaa Xaa Xaa Xaa Trp Gly Xaa
                    85                  90                  95

Xaa Xaa Phe Xaa Xaa Xaa Xaa Xaa Xaa Xaa Xaa Xaa Xaa
            100                 105                 110

Xaa Xaa Xaa Asp Xaa Xaa Xaa Xaa Xaa Xaa Val
        115                 120

<210> SEQ ID NO 23
<211> LENGTH: 139
<212> TYPE: PRT
<213> ORGANISM: Homo sapiens

<400> SEQUENCE: 23

Asp Met Glu Asp Asp Thr Ser Trp Arg Ser Glu Ala Thr Phe Gln Phe
 1               5                   10                  15

Thr Val Glu Arg Phe Ser Arg Leu Ser Glu Ser Val Leu Ser Pro Pro
                20                  25                  30

Cys Phe Val Arg Asn Leu Pro Trp Lys Ile Met Val Met Pro Arg Phe
            35                  40                  45

Tyr Pro Asp Arg Pro His Gln Lys Ser Val Gly Phe Phe Leu Gln Cys
        50                  55                  60

Asn Ala Glu Ser Asp Ser Thr Ser Trp Ser Cys His Ala Gln Ala Val
    65                  70                  75              80

Leu Lys Ile Ile Asn Tyr Arg Asp Asp Glu Lys Ser Phe Ser Arg Arg
                    85                  90                  95

Ile Ser His Leu Phe Phe His Lys Glu Asn Asp Trp Gly Phe Ser Asn
                100                 105                 110

Phe Met Ala Trp Ser Glu Val Thr Asp Pro Glu Lys Gly Phe Ile Asp
            115                 120                 125

Asp Asp Lys Val Thr Phe Glu Val Phe Val Gln
        130                 135

<210> SEQ ID NO 24
<211> LENGTH: 132
<212> TYPE: PRT
<213> ORGANISM: Homo sapiens

<400> SEQUENCE: 24

Ser Tyr Met Trp Thr Ile Asn Asn Phe Ser Phe Cys Arg Glu Glu Met
 1               5                   10                  15
```

```
Gly Glu Val Ile Lys Ser Ser Thr Phe Ser Ser Gly Ala Asn Asp Lys
                20                  25                  30

Leu Lys Trp Cys Leu Arg Val Asn Pro Lys Gly Leu Asp Glu Ser
        35                  40                  45

Lys Asp Tyr Leu Ser Leu Tyr Leu Leu Val Ser Cys Pro Lys Ser
 50                  55                  60

Glu Val Arg Ala Lys Phe Lys Phe Ser Ile Leu Asn Ala Lys Gly Glu
 65                  70                  75                  80

Glu Thr Lys Ala Met Glu Ser Gln Arg Ala Tyr Arg Phe Val Gln Gly
                85                  90                  95

Lys Asp Trp Gly Phe Lys Lys Phe Ile Arg Arg Asp Phe Leu Leu Asp
               100                 105                 110

Glu Ala Asn Gly Leu Leu Pro Asp Asp Lys Leu Thr Leu Phe Cys Glu
               115                 120                 125

Val Ser Val Val
        130

<210> SEQ ID NO 25
<211> LENGTH: 135
<212> TYPE: PRT
<213> ORGANISM: Homo sapiens

<400> SEQUENCE: 25

Glu Leu Val Pro Ser Tyr Asp Ser Ala Thr Phe Val Leu Glu Asn Phe
 1               5                  10                  15

Ser Thr Leu Arg Gln Arg Ala Asp Pro Val Tyr Ser Pro Pro Leu Gln
                20                  25                  30

Val Ser Gly Leu Cys Trp Arg Leu Lys Val Tyr Pro Asp Gly Asn Gly
        35                  40                  45

Val Val Arg Gly Tyr Tyr Leu Ser Val Phe Leu Glu Leu Ser Ala Gly
 50                  55                  60

Leu Pro Glu Thr Ser Lys Tyr Glu Tyr Arg Val Glu Met Val His Gln
 65                  70                  75                  80

Ser Cys Asn Asp Pro Thr Lys Asn Ile Ile Arg Glu Phe Ala Ser Asp
                85                  90                  95

Phe Glu Val Gly Glu Cys Trp Gly Tyr Asn Arg Phe Phe Arg Leu Asp
               100                 105                 110

Leu Leu Ala Asn Glu Gly Tyr Leu Asn Pro Gln Asn Asp Thr Val Ile
               115                 120                 125

Leu Arg Phe Gln Val Arg Ser
        130                 135

<210> SEQ ID NO 26
<211> LENGTH: 150
<212> TYPE: PRT
<213> ORGANISM: Homo sapiens

<400> SEQUENCE: 26

Gly Thr Phe Leu Trp Lys Ile Thr Asn Val Thr Arg Arg Cys His Glu
 1               5                  10                  15

Ser Ala Cys Gly Arg Thr Val Ser Leu Phe Ser Pro Ala Phe Tyr Thr
                20                  25                  30

Ala Lys Tyr Gly Tyr Lys Leu Cys Leu Arg Leu Tyr Leu Asn Gly Asp
        35                  40                  45

Gly Thr Gly Lys Arg Thr His Leu Ser Leu Phe Ile Val Ile Met Arg
 50                  55                  60
```

Gly Glu Tyr Asp Ala Leu Leu Pro Trp Pro Phe Arg Asn Lys Val Thr
65                  70                  75                  80

Phe Met Leu Leu Asp Gln Asn Asn Arg Glu His Ala Ile Asp Ala Phe
                85                  90                  95

Arg Pro Asp Leu Ser Ser Ala Ser Phe Gln Arg Pro Gln Ser Glu Thr
            100                 105                 110

Asn Val Ala Ser Gly Cys Pro Leu Phe Phe Pro Leu Ser Lys Leu Gln
        115                 120                 125

Ser Pro Lys His Ala Tyr Val Lys Asp Asp Thr Met Phe Leu Lys Cys
    130                 135                 140

Ile Val Glu Thr Ser Thr
145                 150

<210> SEQ ID NO 27
<211> LENGTH: 150
<212> TYPE: PRT
<213> ORGANISM: Homo sapiens

<400> SEQUENCE: 27

Gly Val Phe Ile Trp Lys Ile Ser Asp Phe Ala Arg Lys Arg Gln Glu
1               5                   10                  15

Ala Val Ala Gly Arg Ile Pro Ala Ile Phe Ser Pro Ala Phe Tyr Thr
            20                  25                  30

Ser Arg Tyr Gly Tyr Lys Met Cys Leu Arg Ile Tyr Leu Asn Gly Asp
        35                  40                  45

Gly Thr Gly Arg Gly Thr His Leu Ser Leu Phe Val Val Met Lys
    50                  55                  60

Gly Pro Asn Asp Ala Leu Leu Arg Trp Pro Phe Asn Gln Lys Val Thr
65                  70                  75                  80

Leu Met Leu Leu Asp Gln Asn Asn Arg Glu His Val Ile Asp Ala Phe
                85                  90                  95

Arg Pro Asp Val Thr Ser Ser Phe Gln Arg Pro Val Asn Asp Met
            100                 105                 110

Asn Ile Ala Ser Gly Cys Pro Leu Phe Cys Pro Val Ser Lys Met Glu
        115                 120                 125

Ala Lys Asn Ser Tyr Val Arg Asp Asp Ala Ile Phe Ile Lys Ala Ile
    130                 135                 140

Val Asp Leu Thr Gly Leu
145                 150

<210> SEQ ID NO 28
<211> LENGTH: 153
<212> TYPE: PRT
<213> ORGANISM: Homo sapiens

<400> SEQUENCE: 28

Gly Val Leu Ile Trp Lys Ile Arg Asp Tyr Lys Arg Arg Lys Gln Glu
1               5                   10                  15

Ala Val Met Gly Lys Thr Leu Ser Leu Tyr Ser Gln Pro Phe Tyr Thr
            20                  25                  30

Gly Tyr Phe Gly Tyr Lys Met Cys Ala Arg Val Tyr Leu Asn Gly Asp
        35                  40                  45

Gly Met Gly Lys Gly Thr His Leu Ser Leu Phe Val Ile Met Arg
    50                  55                  60

Gly Glu Tyr Asp Ala Leu Leu Pro Trp Pro Phe Lys Gln Lys Val Thr
65                  70                  75                  80

```
Leu Met Leu Met Asp Gln Gly Ser Ser Arg Arg His Leu Gly Asp Ala
                85                  90                  95

Phe Lys Pro Asp Pro Asn Ser Ser Phe Lys Lys Pro Ile Gly Glu
            100                 105                 110

Met Asn Ile Ala Ser Gly Cys Pro Val Phe Val Ala Gln Thr Val Leu
            115                 120                 125

Glu Asn Gly Thr Tyr Ile Lys Asp Asp Thr Ile Phe Ile Lys Val Ile
130                 135                 140

Val Asp Thr Ser Asp Leu Pro Asp Pro
145                 150
```

<210> SEQ ID NO 29
<211> LENGTH: 163
<212> TYPE: PRT
<213> ORGANISM: Homo sapiens

<400> SEQUENCE: 29

```
Gly Val Leu Ile Trp Lys Ile Gly Ser Tyr Gly Arg Arg Leu Gln Glu
1               5                   10                  15

Ala Lys Ala Lys Pro Asn Leu Glu Cys Phe Ser Pro Ala Phe Tyr Thr
            20                  25                  30

His Lys Tyr Gly Tyr Lys Leu Gln Val Ser Ala Phe Leu Asn Gly Asn
        35                  40                  45

Gly Ser Gly Glu Gly Thr His Leu Ser Leu Tyr Ile Arg Val Leu Pro
    50                  55                  60

Gly Ala Phe Asp Asn Leu Leu Glu Trp Pro Phe Ala Arg Arg Val Thr
65                  70                  75                  80

Phe Ser Leu Leu Asp Gln Ser Asp Pro Gly Leu Ala Lys Pro Gln His
                85                  90                  95

Val Thr Glu Thr Phe His Pro Asp Pro Asn Trp Lys Asn Phe Gln Lys
            100                 105                 110

Pro Gly Thr Trp Arg Gly Ser Leu Asp Glu Ser Ser Leu Gly Phe Gly
            115                 120                 125

Tyr Pro Lys Phe Ile Ser His Gln Asp Ile Arg Lys Arg Asn Tyr Val
130                 135                 140

Arg Asp Asp Ala Val Phe Ile Arg Ala Val Glu Leu Pro Arg Lys
145                 150                 155                 160

Ile Leu Ser
```

<210> SEQ ID NO 30
<211> LENGTH: 154
<212> TYPE: PRT
<213> ORGANISM: Homo sapiens

<400> SEQUENCE: 30

```
Gly Lys Leu Ile Trp Lys Val Thr Asp Tyr Lys Met Lys Lys Arg Glu
1               5                   10                  15

Ala Val Asp Gly His Thr Val Ser Ile Phe Ser Gln Ser Phe Tyr Thr
            20                  25                  30

Ser Arg Cys Gly Tyr Arg Leu Cys Ala Arg Ala Tyr Leu Asn Gly Asp
        35                  40                  45

Gly Ser Gly Arg Gly Ser His Leu Ser Leu Tyr Phe Val Val Met Arg
    50                  55                  60

Gly Glu Phe Asp Ser Leu Leu Gln Trp Pro Phe Arg Gln Arg Val Thr
65                  70                  75                  80

Leu Met Leu Leu Asp Gln Ser Gly Lys Lys Asn Ile Met Glu Thr Phe
```

-continued

```
                    85                  90                  95
Lys Pro Asp Pro Asn Ser Ser Phe Lys Arg Pro Asp Gly Glu Met
                100                 105                 110
Asn Ile Ala Ser Gly Cys Pro Arg Phe Val Ala His Ser Val Leu Glu
            115                 120                 125
Asn Ala Lys Asn Ala Tyr Ile Lys Asp Asp Thr Leu Phe Leu Lys Val
        130                 135                 140
Ala Val Asp Leu Thr Asp Leu Glu Asp Leu
145                 150
```

<210> SEQ ID NO 31
<211> LENGTH: 157
<212> TYPE: PRT
<213> ORGANISM: Homo sapiens

<400> SEQUENCE: 31

```
Gly Ile Tyr Ile Trp Lys Ile Gly Asn Phe Gly Met His Leu Lys Cys
1               5                   10                  15
Gln Glu Glu Glu Lys Pro Val Val Ile His Ser Pro Gly Phe Tyr Thr
                20                  25                  30
Gly Lys Pro Gly Tyr Lys Leu Cys Met Arg Leu His Leu Gln Leu Pro
            35                  40                  45
Thr Ala Gln Arg Cys Ala Asn Tyr Ile Ser Leu Phe Val His Thr Met
        50                  55                  60
Gln Gly Glu Tyr Asp Ser His Leu Pro Trp Pro Phe Gln Gly Thr Ile
65                  70                  75                  80
Arg Leu Thr Ile Leu Asp Gln Ser Glu Ala Pro Val Arg Gln Asn His
                85                  90                  95
Glu Glu Ile Met Asp Ala Lys Pro Glu Leu Leu Ala Phe Gln Arg Pro
                100                 105                 110
Thr Ile Pro Arg Asn Pro Lys Gly Phe Gly Tyr Val Thr Phe Met His
            115                 120                 125
Leu Glu Ala Leu Arg Gln Arg Thr Phe Ile Lys Asp Asp Thr Leu Leu
        130                 135                 140
Val Arg Cys Glu Val Ser Thr Arg Phe Asp Met Gly Ser
145                 150                 155
```

<210> SEQ ID NO 32
<211> LENGTH: 964
<212> TYPE: PRT
<213> ORGANISM: Homo sapiens

<400> SEQUENCE: 32

```
Met Asp Glu Gln Ser Val Glu Ser Ile Ala Glu Val Phe Arg Cys Phe
1               5                   10                  15
Ile Cys Met Glu Lys Leu Arg Asp Ala Arg Leu Cys Pro His Cys Ser
                20                  25                  30
Lys Leu Cys Cys Phe Ser Cys Ile Arg Arg Trp Leu Thr Glu Gln Arg
            35                  40                  45
Ala Gln Cys Pro His Cys Arg Ala Pro Leu Gln Leu Arg Glu Leu Val
        50                  55                  60
Asn Cys Arg Trp Ala Glu Glu Val Thr Gln Gln Leu Asp Thr Leu Gln
65                  70                  75                  80
Leu Cys Ser Leu Thr Lys His Glu Glu Asn Glu Lys Asp Lys Cys Glu
                85                  90                  95
Asn His His Glu Lys Leu Ser Val Phe Cys Trp Thr Cys Lys Lys Cys
```

-continued

```
                100                 105                 110
Ile Cys His Gln Cys Ala Leu Trp Gly Gly Met His Gly Gly His Thr
            115                 120                 125
Phe Lys Pro Leu Ala Glu Ile Tyr Glu Gln His Val Thr Lys Val Asn
        130                 135                 140
Glu Glu Val Ala Lys Leu Arg Arg Arg Leu Met Glu Leu Ile Ser Leu
145                 150                 155                 160
Val Gln Glu Val Glu Arg Asn Val Glu Ala Val Arg Asn Ala Lys Asp
                165                 170                 175
Glu Arg Val Arg Glu Ile Arg Asn Ala Val Glu Met Met Ile Ala Arg
            180                 185                 190
Leu Asp Thr Gln Leu Lys Asn Lys Leu Ile Thr Leu Met Gly Gln Lys
        195                 200                 205
Thr Ser Leu Thr Gln Glu Thr Glu Leu Leu Glu Ser Leu Leu Gln Glu
210                 215                 220
Val Glu His Gln Leu Arg Ser Cys Ser Lys Ser Glu Leu Ile Ser Lys
225                 230                 235                 240
Ser Ser Glu Ile Leu Met Met Phe Gln Gln Val His Arg Lys Pro Met
                245                 250                 255
Ala Ser Phe Val Thr Thr Pro Val Pro Pro Asp Phe Thr Ser Glu Leu
            260                 265                 270
Val Pro Ser Tyr Asp Ser Ala Thr Phe Val Leu Glu Asn Phe Ser Thr
        275                 280                 285
Leu Arg Gln Arg Ala Asp Pro Val Tyr Ser Pro Leu Gln Val Ser
290                 295                 300
Gly Leu Cys Trp Arg Leu Lys Val Tyr Pro Asp Gly Asn Gly Val Val
305                 310                 315                 320
Arg Gly Tyr Tyr Leu Ser Val Phe Leu Glu Leu Ser Ala Gly Leu Pro
                325                 330                 335
Glu Thr Ser Lys Tyr Glu Tyr Arg Val Glu Met Val His Gln Ser Cys
            340                 345                 350
Asn Asp Pro Thr Lys Asn Ile Ile Arg Cys Phe Ala Ser Asp Phe Glu
        355                 360                 365
Val Gly Glu Cys Trp Gly Tyr Asn Arg Phe Phe Arg Leu Asp Leu Leu
370                 375                 380
Ala Asn Glu Gly Tyr Leu Asn Pro Gln Asn Asp Thr Val Ile Leu Arg
385                 390                 395                 400
Phe Gln Val Arg Ser Pro Thr Phe Phe Gln Lys Ser Arg Asp Gln His
                405                 410                 415
Trp Tyr Thr Ile Gln Leu Glu Ala Ala Gln Thr Ser Tyr Ile Gln Gln
            420                 425                 430
Ile Asn Asn Leu Lys Glu Arg Leu Thr Ile Glu Leu Ser Arg Thr Gln
        435                 440                 445
Lys Ser Arg Asp Leu Ser Pro Pro Asp Asn His Leu Ser Pro Gln Asn
    450                 455                 460
Asp Asp Ala Leu Glu Thr Arg Ala Lys Lys Ser Ala Cys Ser Asp Met
465                 470                 475                 480
Leu Leu Glu Gly Gly Pro Thr Thr Ala Ser Val Arg Glu Ala Lys Glu
                485                 490                 495
Asp Glu Glu Asp Glu Glu Lys Ile Gln Asn Glu Asp Tyr His His Glu
            500                 505                 510
Leu Ser Asp Gly Asp Leu Asp Leu Asp Leu Val Tyr Glu Asp Glu Val
        515                 520                 525
```

```
Asn Gln Leu Asp Gly Ser Ser Ser Ala Ser Ser Thr Ala Thr Ser
    530                 535                 540
Asn Thr Glu Glu Asn Asp Ile Asp Glu Glu Thr Met Ser Gly Glu Asn
545                 550                 555                 560
Asp Val Glu Tyr Asn Asn Met Glu Leu Glu Glu Gly Glu Leu Met Glu
                565                 570                 575
Asp Ala Ala Ala Gly Pro Ala Gly Ser Ser His Gly Tyr Val Gly
            580                 585                 590
Ser Ser Ser Arg Ile Ser Arg Arg Thr His Leu Cys Ser Ala Ala Thr
        595                 600                 605
Ser Ser Leu Leu Asp Ile Asp Pro Leu Ile Leu Ile His Leu Leu Asp
    610                 615                 620
Leu Lys Asp Arg Ser Ser Ile Glu Asn Leu Trp Gly Leu Gln Pro Arg
625                 630                 635                 640
Pro Pro Ala Ser Leu Leu Gln Pro Thr Ala Ser Tyr Ser Arg Lys Asp
                645                 650                 655
Lys Asp Gln Arg Lys Gln Gln Ala Met Trp Arg Val Pro Ser Asp Leu
                660                 665                 670
Lys Met Leu Lys Arg Leu Lys Thr Gln Met Ala Glu Val Arg Cys Met
            675                 680                 685
Lys Thr Asp Val Lys Asn Thr Leu Ser Glu Ile Lys Ser Ser Ser Ala
    690                 695                 700
Ala Ser Gly Asp Met Gln Thr Ser Leu Phe Ser Ala Asp Gln Ala Ala
705                 710                 715                 720
Leu Ala Ala Cys Gly Thr Glu Asn Ser Gly Arg Leu Gln Asp Leu Gly
                725                 730                 735
Met Glu Leu Leu Ala Lys Ser Ser Val Ala Asn Cys Tyr Ile Arg Asn
                740                 745                 750
Ser Thr Asn Lys Lys Ser Asn Ser Pro Lys Pro Ala Arg Ser Ser Val
    755                 760                 765
Ala Gly Ser Leu Ser Leu Arg Arg Ala Val Asp Pro Gly Glu Asn Ser
770                 775                 780
Arg Ser Lys Gly Asp Cys Gln Thr Leu Ser Glu Gly Ser Pro Gly Ser
785                 790                 795                 800
Ser Gln Ser Gly Ser Arg His Ser Ser Pro Arg Ala Leu Ile His Gly
                805                 810                 815
Ser Ile Gly Asp Ile Leu Pro Lys Thr Glu Asp Arg Gln Cys Lys Ala
                820                 825                 830
Leu Asp Ser Asp Ala Val Val Ala Val Phe Ser Gly Leu Pro Ala
    835                 840                 845
Val Glu Lys Arg Arg Lys Met Val Thr Leu Gly Ala Asn Ala Lys Gly
    850                 855                 860
Gly His Leu Phe Gly Leu Gln Met Thr Asp Leu Glu Asn Asn Ser Glu
865                 870                 875                 880
Thr Gly Phe Leu Gln Pro Val Leu Pro Glu Gly Ala Ser Ala Pro
                885                 890                 895
Glu Glu Gly Met Ser Ser Asp Ser Asp Ile Glu Gly Asp Thr Glu Asn
                900                 905                 910
Glu Glu Gln Glu Glu His Thr Ser Val Gly Gly Phe His Asp Ser Phe
            915                 920                 925
Met Val Met Thr Gln Pro Pro Asp Glu Asp Thr His Ser Ser Glu Pro
930                 935                 940
```

```
                                    -continued
Asp Gly Phe Gln Ile Gly Pro Glu Asp Leu Ser Phe Asn Thr Asp Glu
945                 950                 955                 960
Asn Ser Gly Arg
```